(12) United States Patent
Sen et al.

(10) Patent No.: US 7,833,785 B2
(45) Date of Patent: Nov. 16, 2010

(54) METHOD FOR CHEMICAL DISSOCIATION OF CELLS FROM PHYSICAL SURFACES

(76) Inventors: Arindom Sen, 2311 Tuscarora Manor NW., Calgary, AB (CA) T3L 2J9; Michael S. Kallos, 319-20 Sierra Morena Mews S.W., Calgary, AB (CA) T3H 3K6; Leo A. Behie, 2532 Chicoutimi Drive N.W., Calgary, AB (CA) T2L 0W5

( * ) Notice: Subject to any disclaimer, the term of this patent is extended or adjusted under 35 U.S.C. 154(b) by 0 days.

(21) Appl. No.: 11/970,562

(22) Filed: Jan. 8, 2008

(65) Prior Publication Data

US 2008/0187519 A1     Aug. 7, 2008

Related U.S. Application Data

(62) Division of application No. 11/083,071, filed on Mar. 18, 2005, now abandoned.

(60) Provisional application No. 60/553,947, filed on Mar. 18, 2004.

(51) Int. Cl.
    *A61K 48/00*      (2006.01)
    *C12N 5/00*      (2006.01)
    *C12N 5/02*      (2006.01)
    *C12Q 1/20*      (2006.01)

(52) U.S. Cl. .................. 435/325; 435/358; 435/29; 435/378; 435/404; 424/93.7

(58) Field of Classification Search ................ None
See application file for complete search history.

(56) References Cited

U.S. PATENT DOCUMENTS

2002/0198928 A1* 12/2002 Bukshpan et al. ........... 709/200
2003/0040104 A1* 2/2003 Barbera-Guillem ...... 435/286.2

FOREIGN PATENT DOCUMENTS

WO    WO 2004/013315      2/2004

OTHER PUBLICATIONS

Reynolds, B.A., and Weiss, S. 1996. Clonal and Population Analyses Demonstrate That an EGF-Responsive Mammalian Embryonic CNS Precursor Is a Stem Cell. Developmental Biology 175:1-13.
Allen, C.N., Brady, R., Swann, J., Hori, N., and Carpenter, D.O. 1988. N-Methyl-D-aspartate (NMDA) receptors are inactivated by trypsin. Brain Research 458:147-150.
Lee, S.H., Lumelsky, N., Studer, L., Auerbach, J.M., and McKay, R.D. 2000. Efficient generation of midbrain and hindbrain neurons from mouse embryonic stem cells. Nature Biotechnology 18:675-679.
Murayama, A., Matsuzaki, Y., Kawaguchi, A., Shimazaki, T., and Okano, H. 2002. Flow Cytometric Analysis of Neural Stem Cells in the Developing and Adult Mouse Brain. Journal of Neuroscience Research 69:837-847.
Martin, F.C., and Wiley, C.A. 1994. An alternative method for obtaining high viability cell suspensions from neonatal mouse brain. Journal of Neuroscience Methods 55:99-104.
Reynolds, B.A., and Weiss, S. 1992. Generation of Neurons and Astrocytes from Isolated Cells of the Adult Mammalian Central Nervous System. Science 255:1707-1710.
Stingl, J., Emerman, J.T., and Eaves, C.J. 2005. Enzymatic Dissociation and Culture of Normal Human Mammary Tissue to Detect Progenitor Activity *from* Methods in Molecular Biology 290:249-263.
Caldwell, M.A., He, X., Wilkie, N., Pollack, S., Marshall, G., Wafford, K.A., and Svendson, C.N. 2001. Growth factors regulate the survival and fate of cells derived from human neurospheres. Nature Biotechnology 19:475-479.
Avellana-Adalid, V., Nait-Oumesmar, B., Lachapelle, F., and Baron-Van Evercooren, A. 1996. Expansion of Rat Oligodendrocyte Progenitors Into Proliferative "Oligospheres" That Retain Differentiation Potential. Journal of Neuroscience Research 45:558-570.
Torres, F.X., Mackowiak, P.G., Brown, R.D., Linden, M.D., and Zarbo, R.J. 1995. Comparison of two methods of mechanical disaggregation of scirrhous breast adenocarcinomas for DNA flow cytometric analysis of whole cells. American Journal of Clinical Pathology 103(1):8-13.
Sen, A., Kallos, M.S., Behie, L.A. 2004. New Tissue Dissociation Protocol for Scaled-up Production of Neural Stem Cells in Suspension Bioreactors. Tissue Engineering 10(5/6):904-913.
Youn, B.S., Sen, A., Kallos, M.S., Behie, L.A., Girgis-Gabardo, A., Kurpios, N., Barcelon, M., Hassell, J.A. 2005. Large-Scale Expansion of Mammary Epithelial Stem Cell Aggregates in Suspension Bioreactors. Biotechnology Program 21(3):984-993.
Sen, A., Kallos, M.S., Behie, L.A., Experimental Techniques for the Dissociation of Cellular Aggregates in the Large-Scale Production of Mammalian Neural Stem Cells in Suspension Bioreactors, Abstract, 50th Canadian Chemical Engineering Conference, Oct. 15-18, 2000, Montreal, QC.
Sen, A., Kallos, M.S., Behie, L.A., A New Protocol for the Dissociation of Mammalian Neural Stem Cell Aggregates, Abstract, Keystone Symposia (From Stem Cells to Therapy), Steamboat Springs, Colorado, Mar. 29-Apr. 3, 2003.
Kallos et al., Extended Serial Passaging of Mammalian Neural Stem Cells in Suspension Bioreactors, 1999, Biotechnology and Bioengineering, vol. 65, No. 5, p. 589-599.

* cited by examiner

*Primary Examiner*—Lisa J Hobbs
(74) *Attorney, Agent, or Firm*—Micheline Gravelle; Bereskin & Parr LLP/S.E.N.C.R.L., s.r.l.

(57) ABSTRACT

The invention provides a novel method of dissociating anchorage independent and dependent cell aggregates. The invention also includes the cells resulting from the methods of the invention and the use of the cells in various applications requiring the generation of a single cell suspension.

30 Claims, 47 Drawing Sheets

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Passage | Before dissociation | After dissociation |
|---|---|---|
| 1 |  |  |
| 2 |  |  |
| 3 |  |  |
| 4 |  |  |

| Base used in Dissociation Solution | Before dissociation | After dissociation |
|---|---|---|
| Trypsin/EDTA |  |  |
| Sodium Hydroxide |  |  |
| Sodium Carbonate |  |  |

| Base used in Dissociation Solution | Before dissociation | After dissociation |
|---|---|---|
| Sodium Phosphate |  |  |
| Ammonium Hydroxide |  |  |
| Potassium Hydroxide |  |  |

| Time (min) | Passage 1 | Passage 2 | Passage 3 | Passage 4 |
|---|---|---|---|---|
| 0 | | | | |
| 2 | | | | |
| 4 | | |  |  |
| 6 |  |  | | |
| 10 | | |  |  |
| After | |  |  |  |

| Time (min) | Passage 1 | Passage 2 | Passage 3 |
|---|---|---|---|
| 0 | |  |  |
| 2 |  |  |  |
| 5 |  |  |  |
| 15 |  | |  |
| 20 |  |  | |
| After | |  |  |

| Time (min) | Passage 1 | Passage 2 | Passage 3 |
|---|---|---|---|
| 0 | |  |  |
| 2 |  |  |  |
| 5 |  |  |  |
| 15 |  | |  |
| 20 |  |  | |
| After | |  | |

| Time (min) | Passage 1 | Passage 2 | Passage 3 | Passage 4 |
|---|---|---|---|---|
| 0 | | | | |
| 2 | | | | |
| 4 | | | | |
| 6 | | | | |
| 10 | | | | |
| After | | | | |

FIGURE 45

| Time (min) | Passage 1 | Passage 2 | Passage 3 | Passage 4 |
|---|---|---|---|---|
| 0 | | | | |
| 2 | | | | |
| 4 | | | | |
| 6 | | | | |
| 10 | | | | |
| After | | | | |

FIGURE 46

| Time (min) | Passage 1 | Passage 2 | Passage 3 | Passage 4 |
|---|---|---|---|---|
| 0 |  |  |  |  |
| 2 |  |  |  |  |
| 4 |  | |  |  |
| 6 |  |  | | |
| 10 | | |  |  |
| After | |  |  | |

METHOD FOR CHEMICAL DISSOCIATION OF CELLS FROM PHYSICAL SURFACES

This application is a divisional of U.S. Ser. No. 11/083,071 that was filed on Mar. 18, 2005 (now pending), which claims the benefit of priority under 35 USC §119(e) from United States Provisional application No. 60/553,947 filed Mar. 18, 2004 which is incorporated herein by reference.

FIELD OF THE INVENTION

The present invention relates to a method for the chemical dissociation of cell aggregates producing minimal cell damage, maximizing cell viability and retaining the biological properties of the cells post dissociation.

BACKGROUND OF THE INVENTION

When cells are extracted from mammalian tissues and placed in culture, they tend to behave as either anchorage dependent or anchorage independent. Anchorage dependent mammalian cells grow by first attaching to a surface. These cells often divide until the surface on which they are attached is fully covered i.e. they divide and aggregate to form a confluent monolayer. Examples of anchorage dependent cells that are commonly used in industrial and research settings include Chinese Hamster Ovary cells (CHO cells) and L-929 Murine Lung Fibroblast Cells. Anchorage independent cells, however, do not require a surface on which to attach prior to dividing. Rather, after being placed in culture, they grow in suspension either as single cells, or as clusters of cells which are often referred as suspended spheres or suspended aggregates of cells. Examples of this include neural stem cells and mammary stem cells.

A substantial proportion of the volume within a suspended aggregate in culture is comprised of space between the cells (similar to tissues). Most of this extracellular space is filled with an intricate network of proteins and polysaccharides collectively termed an extracellular matrix (ECM). The molecules which make up the matrix can be divided into two categories: extracellular matrix molecules (ECM molecules) and cell adhesion molecules (CAMs). ECM molecules (comprised of collagen, proteoglycans and non-collagen glycoproteins) are secreted into the extracellular space where they are assembled into a complex mesh that remains closely associated with the cell that produced them. Since they are produced locally, the amount and composition of the ECM can vary considerably throughout an aggregate or a tissue. Due to the massive quantities of ECM in connective tissues such as bone, tendon, cartilage, and dermis, it was originally believed that the function of the ECM was simply to provide inert physical support. However, recent evidence shows that the ECM is a complex and dynamic entity that can regulate the survival, development, migration, proliferation, shape and function of the cells in contact with it (Alberts et al., 2002).

In addition to ECM molecules, CAMs are also known to exist between both anchorage dependent cells and anchorage independent cells. The term 'cell adhesion' implies that these molecules are a form of intercellular glue. Whereas they do bind cells in close proximity to one another, they have very important roles in tissue development and inter- and intracellular signaling. CAMs can be subdivided into four different families based on structural homology. They are the immunoglobulin superfamily of CAMs (IgCAMs), cadherins, selecting, and integrins.

CAMs can interact with one another, and with ECM molecules. Many ECM molecules and CAMs have important secondary and tertiary structures, and their conformation in the extracellular matrix allows them to interact through the formation of weak noncovalent bonds such as hydrogen bonds, and stronger bonds such as ionic bonds mediated by divalent cations, or covalent disulfide bridges between amino acid residues. These intercellular interactions cause cells in a confluent monolayer or a suspended aggregate to bind very strongly to one another.

Most tissues such as the pancreas and the brain are made up of billions of cells that are held together by ECM molecules and CAMs. In order to isolate cells from these primary tissues for cell culture, it is necessary to dissociate the tissues into a single cell suspension prior to being placed into culture. Once in culture, most cells tend to divide and/or reassociate with each other to form monolayers or suspended clusters. Even hematopoietic cells (which are typically present as a single cell suspension in vivo) tend to aggregate when manipulated in culture. If it is desired to maintain actively proliferating cells in culture beyond a few days, it is necessary to subculture the cells (i.e. remove them from one culture vessel, and place them at a lower cell concentration into a new culture vessel containing fresh medium). In order to do this in anchorage dependent cultures, monolayers of cells have to first be detached from the surface on which they are attached, and then the detached monolayers have to be dissociated into a single cell suspension. In anchorage independent cultures, the suspended clusters of cells have to be dissociated into a single cell suspension. The single cell suspension can then be used to inoculate a new culture vessel.

In addition to isolating cells from primary tissues, and subculturing cells in existing cultures, the generation of single cell suspensions is extremely important for a variety of applications. For example, during cell therapy, single cells are delivered to certain sites in order to treat specific conditions. Transplanting aggregates is undesirable because (i) aggregates can plug the delivery device (ii) it is difficult to estimate the number of actual cells that are delivered (iii) cells in aggregates are more susceptible to cell death due to the nutrient and oxygen mass transfer limitations that they suffer and (iv) aggregates are less likely to migrate to areas of damage, respond to local cues, and integrate into the host cellular architecture. Single cells are also necessary for basic biological research. For example, cell sorting methods are used to determine the composition of heterogeneous cell populations, and to isolate specific subpopulations of cells with desirable characteristics which can then be used to conduct further research, or used therapeutically in a clinical setting. Cell sorting methods can only be used effectively on single cells. The generation of a single cell suspension also has applications in other areas such as the production of biomolecules and clinical diagnostics.

Several methods have been developed to generate single cell suspensions from primary tissues, attached cells in culture, and aggregates in culture reviewed in (Freshney, 2000). These methods involve the use of physical forces (mechanical dissociation), enzymes (enzymatic dissociation), or a combination of both. Mechanical means of detaching cells that are attached to a surface include the use of cell scrapers. Mechanical means of separating cells which are attached to one another include trituration through a narrow bore pipette (Reynolds and Weiss, 1992; Sen et al., 2001), fine needle aspiration (Ottesen et al., 1996), vortex disaggregation (Vos et al., 2003), and forced filtration through a fine nylon or stainless steel mesh. Whereas all of these methods are effective in creating single cell suspensions, the excessive physical forces involved often result in a significant amount of cell death and cell damage. In situations where the generation of a suspension of viable single cells is the ultimate goal, cell death and cell damage are extremely undesirable.

Mechanical dissociation can also result in the death of specific groups of important cells within a heterogeneous population. For example, larger cells are known to be more sensitive to shear than smaller cells. Continually killing specific cell types during serial passaging could be detrimental to a cell line during long term culture. In addition, the death of specific cell types could adversely impact results derived from procedures that rely on the generation of a single cell suspension such as flow activated cell sorting, and clonal and population analyses in the promising area of stem cell biology. Moreover the manual nature of certain mechanical dissociation protocols (e.g. trituration, which is done by hand) often make it difficult compare measured values (such as cell viability) from different sources since dissociation efficiency varies between individuals. In fact, the manual nature of this procedure may contribute to differences in the physical attributes (e.g. cell concentration, cell viability, cell size distribution etc.) between two otherwise identical samples.

In an attempt to avoid the negative consequences of mechanical dissociation, researchers have used enzymes (either alone or in combination) which are directed towards one or more components in the ECM. Certain enzymes are known to target and cleave specific molecules present within the ECM. For example, the enzyme trypsin (which cleaves polypeptide chains on the carboxyl side of arginine and lysine residues) is commonly used to detach and dissociate monolayer cultures, whereas collagenase is often used to dissociate primary tissues and aggregates. However, not all cell types can be easily dissociated using enzymes. For those cell types that are susceptible to enzymatic dissociation, it has been shown that enzymes can be detrimental to the cells and negatively impact the ability of the generated single cells to subsequently survive and/or divide. For example, when neural stem cell (NSC) aggregates were dissociated using trypsin, the growth rate of the single cells in subsequent culture was found to have been adversely affected relative to single cells generated using mechanical dissociation (Sen, 2003). This result may be attributable to the fact that trypsin is known to cleave certain classes of cell surface transmitter receptors (Allen et al., 1988). In the extreme, enzymes can completely destroy cells. For example, collagenase has been shown to reduce viable cells to debris when used to dissociate neural stem cell aggregates (Kallos et al., 1999).

Human embryonic neural stem cells inoculated into serum free medium can be induced to divide and form aggregates over time. Visually, the aggregates contain a significantly greater amount of extracellular matrix compared to embryonic neural stem cell aggregates derived from mice. Currently, the state-of-the-art method of generating a single cell suspension from these aggregates involves mechanical dissociation. However, due to the large quantities of extracellular matrix, mechanical dissociation of human neurosphere aggregates results in a much greater cell death relative to that caused during the mechanical dissociation of murine neural stem cell aggregates. Even in the hands of an experienced researcher, it is not unusual to obtain measured cell viabilities of 50% or less.

Pancreatic stem cells are cells that are believed to give rise to all of the different endocrine tissues within the pancreas. It is anticipated that research efforts that are presently underway using these cells will eventually lead to cell therapy aimed at eliminating Type I diabetes, a currently incurable disease afflicting millions of individuals. At present, due to the prevalence of this disease, and the associated economic impact, there is an extensive amount of research being conducted in an effort to expand this stem cell population. Pancreatic stem cells are obtained from whole pancreatic tissue through a series of fractionations. The fraction containing the stem cells is isolated from the other fractions and placed into a serum free medium. Currently, there are no methods available to expand these cells in vitro. Rather, the medium simply serves to maintain the cells in culture, and delay cell death. The cells in this fraction, including the stem cells are present as large aggregates of primary tissue. Large aggregates are undesirable since cells rapidly begin to die due to nutrient and oxygen limitations. Thus, in order to ensure that the cells survive, and to isolate the stem cells from the rest of the cells, it is necessary to dissociate the tissue into a single cell suspension. At present, there are no reliable or reproducible methods to accomplish this. Until now, the best method utilized by researchers, and the current accepted practice in this field has been to mechanically dissociate the aggregates. However, this method does not result in the generation of a single cell suspension. Rather, many cell aggregates remain. Significantly increasing the intensity and duration of the mechanical dissociation process does not remove these aggregates, but rather, results in the death of large numbers of otherwise viable cells. Thus, despite being the most commonly used procedure in this field, mechanical dissociation is not ideal.

It has recently been hypothesized that mutations to cells within the relatively quiescent stem cell compartment of mammary tissue results in the generation of breast cancer when rapid mitotic activity ensues. Thus, there has been a significant increase in research activity related to these cells. One difficulty in conducting research with these cells is that they tend to aggregate when placed into serum-free culture. These aggregates (referred to as mammospheres) are comprised of tightly arranged cells which are very difficult to mechanically dissociate into a single cell suspension.

Chinese hamster ovary cells are very well characterized, and are used extensively in many commercial applications. These cells can be induced to grow as both suspended aggregates, or as a monolayer culture in which the cells are attached to a substrate. In both cases there are issues related to generating a single cell suspension. If the cells are attached as a monolayer, then mechanical dissociation is not effective, and enzymatic means (such as trypsin with EDTA) are routinely used to detach the cells, and subsequently break them into single cells. However, enzymatic approaches are known to cause cell damage, or even death.

Embryonic stem cells (ES) are primitive, undifferentiated cells derived from the inner cell mass of a blastocyst. These cells are termed pluripotent as they have the capacity to differentiate and give rise to the multitude of different cell types which comprise an organism. It has been shown that these cells require attachment to a substrate in order to remain undifferentiated in vitro. If not allowed to attach, the cells form aggregates in suspension called embryoid bodies, and start to differentiate within these aggregates. The current state-of-the-art in this field with respect to detaching the cells from the surface of a flask is to use enzymes such as trypsin. However, as described earlier, enzymes can be harmful to the cells.

In view of the aforementioned deficiencies attendant with prior art methods of dissociating cells in both anchorage dependent and anchorage independent cultures, a need exists for a new approach that reduces the negative consequences of mechanical dissociation and enzymatic dissociation.

SUMMARY OF THE INVENTION

The present invention provides a reproducible procedure for (i) the chemical dissociation of cell aggregates resulting in minimal damage to the cells, and (ii) the chemical dissociation of cells attached to surfaces resulting in minimal damage to the cells. The present invention, hereafter also referred to as chemical dissociation, is a significant advancement over currently used dissociation methods, allowing for increased viability, reduced cell damage, a significant increase in total number of cells generated and the maintenance of the functional properties of the cells upon subsequent sub-culture.

Accordingly, the present invention provides a method for chemically dissociating cell aggregates in a medium comprising the steps of:
 a) increasing the pH of the medium;
 b) generating a single cell suspension; and
 c) decreasing the pH of the medium.

In one embodiment, the cell aggregates are attached to a physical surface. Accordingly, the present invention provides a method for chemically detaching cells from a physical surface comprising the steps of:
 a) increasing the pH of the medium in the presence of an chelating agent;
 b) generating a single cell suspension; and
 c) decreasing the pH of the medium.

The present invention also provides for the chemically dissociated or detached cells resulting from the methods of the invention.

In a further embodiment, the invention provides for the use of the chemically dissociated or detached cells of the invention for various applications. Examples of such applications include cells for in vitro cell culture, both short and long term, FACS analysis, cellular therapy, production of bio-molecules and clonal analysis.

In another embodiment, the invention provides for a kit for generating chemically dissociated cells comprising alkaline medium, acidic medium, and instructions for use.

In another embodiment, the invention provides a kit for chemically detaching cells from a physical surface comprising alkaline medium, a chelating agent, acidic medium, and instructions for use.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The invention will now be described in relation to the drawings in which:

FIG. 45. Photomicrographs showing the effect of serially subculturing (4 passages) L-929 cells after these cells were dissociated using an NaOH-EDTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.

FIG. 46. Photomicrographs showing the effect of serially subculturing (4 passages) L-929 cells after dissociation using an NaOH-EGTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.

BRIEF DESCRIPTION OF THE TABLES

Figure 1:
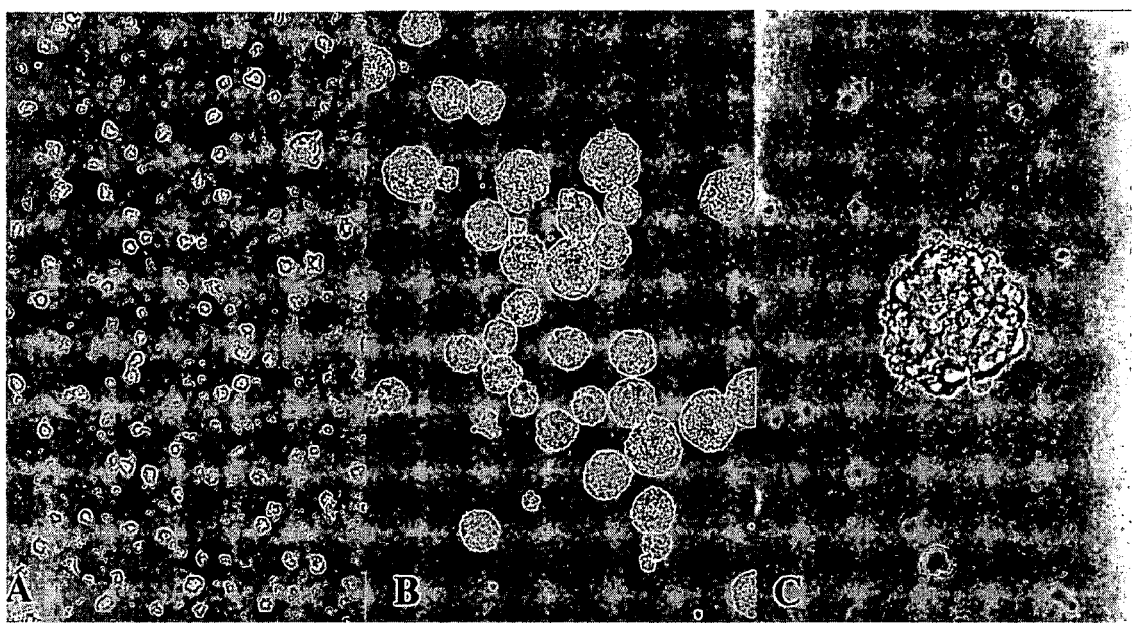
FIG. 1 shows first and second Passage Neurospheres. Embryonic day 14 mouse cortex was dissociated into a single cell suspension and plated in a defined serum-free medium containing EGF at a density of 500,000 cells per ml. Three days after plating, small clusters of cells attached to the substrate can be identified (A). Four days later, clonally derived neurospheres are seen floating in suspension (B). Neurospheres were collected, mechanically dissociated into a single cell suspension and replated. A second passage 7 day old neurosphere (C).
Figure 2:
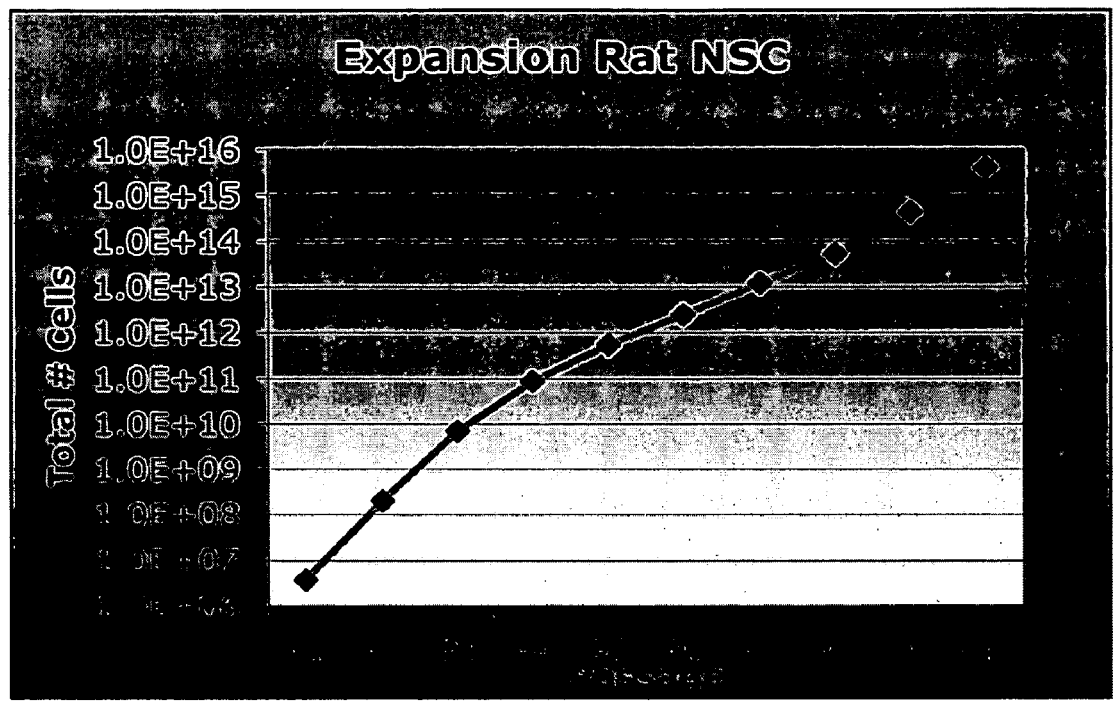
FIG. 2 shows a theoretical growth curve of passaged Rat NSC. Theoretical number of total viable cells generated after 10 passages. Data represent the potential total number of cells generated, based on aliquots counted at each passage, following 10 successive passages. Starting with $1\times10^6$ cells and had all the cells been saved at each passage, by passage 10, $4.03\times10^{15}$ cells would have been generated. This represents a $10^9$-fold increase over $10^{15}$ weeks.

Table 1: A synopsis of the number of analyzed particles within a given forward scatter (FS) range. A total of 10,000 particles (debris and intact neural mouse cells) were analyzed for both mechanically and chemically dissociated samples. The data are presented in two formats—percentage of total particles analyzed, and percentage of intact cells. Debris is generated from destroyed cells, and when these particles are analyzed by the FACScan, have FS values smaller than 200 and side scatter (SS) values smaller that 120 (Alam, 2003). Thus, to determine the percentage of intact cells within a given range of FS values, all of the data points in the region FS<200 and SS<120 were excluded.

Table 2. The viable cell concentration, viabilities, and fold increase in viable cells for mouse neurospheres dissociated into single cell suspension using different bases (listed in the table). Following dissociation, the pH was reduced by using neutralizing solution generated using HCl. Cell counts and viabilities were determined by trypan blue exclusion. Cells were serially subcultured for 4 passages in 25 $cm^2$ tissue culture flasks containing 5 mL of PPRF-m4 medium. The flasks were maintained in a humidified 37° C. incubator containing 5% $CO_2$ (Average values, n=3).

Table 3. The viable cell concentration, viabilities, and fold increase in number of viable cells for mouse neurospheres exposed to different acidic neutralizing solutions following chemical dissociation. The aggregates were dissociated into a single cell suspension using an NaOH based dissociation solution. Acidic neutralizing solutions generated using a variety of acids (listed in table) were then added to counteract the high pH of the dissociation medium. Cell counts and viabilities were determined by trypan blue exclusion. Cells were serially subcultured for 4 passages in 25 cm² tissue culture flasks containing 5 mL of PPRF-m4 medium. The flasks were maintained in a humidified 37° C. incubator containing 5% $CO_2$ (Average values, n=3).

Table 4 The viable cell concentration, viabilities, and fold increase in number of viable cells for mouse embryonic stem cells detached from a surface and dissociated into a single cell suspension using different bases (listed in the table). Cell counts and viabilities were determined by trypan blue exclusion. Cells were serially subcultured for 4 passages in 25 cm² tissue culture flasks which were maintained in a humidified 37° C. incubator containing 5% $CO_2$ (Average values, n=3).

Table 5. The viable cell concentration and cell viabilities for L929 cells that were detached and dissociated into a single cell suspension using dissociation solutions containing different chelating agents (listed in the table). Following dissociation, the pH was reduced by using neutralizing solutions generated using HCl. Cell counts and viabilities were determined by trypan blue exclusion. Cells were serially subcultured for 4 passages in 25 cm² tissue culture flasks containing 5 mL of adherent cell medium. The flasks were maintained in a humidified 37° C. incubator containing 5% $CO_2$ (Average values, n=3).

Table 6. The viable cell concentration and cell viabilities for CHO cells that were detached and dissociated into a single cell suspension using dissociation solutions containing different chelating agents (listed in the table). Following dissociation, the pH was reduced by using neutralizing solutions generated using HCl. Cell counts and viabilities were determined by trypan blue exclusion. Cells were serially subcultured for 3 passages in 25 cm² tissue culture flasks containing 5 mL of adherent cell medium. The flasks were maintained in a humidified 37° C. incubator containing 5% $CO_2$ (Average values, n=3).

DETAILED DESCRIPTION OF THE INVENTION

The present invention involves the manipulation of pH levels to generate single cell suspensions. The present invention provides methods for the dissociation of cellular aggregates of both anchorage independent cells and for anchorage dependent cells. This method resulted in significantly higher cell concentrations and viabilities than dissociating similar samples mechanically or enzymatically. Lactate dehydrogenase release kinetics which is used to measure the level of dead and dying cells, revealed that this method was less harmful to cells than mechanical dissociation, and FACScan analysis revealed much less debris production. Cells generated using chemical dissociation displayed shorter lag times in subsequent cultures. Moreover, this method was found to be superior for the simultaneous dissociation of large quantities of aggregates, making it ideal for handling cells from scaled-up cultures. Chemical dissociation was found to have no adverse effects on the long-term proliferation and differentiation of the cells.

This demonstrates that pH dependent dissociation is a general phenomenon with applications that include an extremely broad variety of cells. In summary, this novel approach to creating a single cell suspension has the following advantages:

(i) minimizes the destruction of cells during detachment and dissociation, thereby significantly increasing the efficiency of cell expansion in culture for applications including cell therapy and the production of bio-molecules;
(ii) allows the cells to retain their ability to proliferate during subsequent subculture over both short and extended culture periods;
(iii) does not affect the defining characteristics of the cells;
(iv) is efficient and does not extend beyond a few minutes in length;
(v) can be scaled-up to handle large quantities of cells in an efficient manner; and
(vi) is reproducible and allows for a standard approach to be used by different clinicians and researchers.

Chemical Dissociation of Anchorage Independent Cell Aggregates:

The present invention provides a method for chemically dissociating cell aggregates in a medium comprising the steps of:
a) increasing the pH of the medium;
b) generating a single cell suspension; and
c) decreasing the pH of the medium.

"Increasing the pH" generally means increasing the pH of the medium to a more alkaline pH. The increase in pH may be provided by addition of alkaline medium. The alkaline medium optionally comprises medium and a base. Examples of suitable bases include sodium hydroxide, potassium hydroxide, calcium hydroxide, ammonium hydroxide, zinc hydroxide, sodium phosphate tribasic dodecahydrate and sodium carbonate. The pH is preferably increased to a pH ranging from 9 to 11.5. The pH is most preferably about 10.

The generation of the single cell suspension may be achieved by pipetting the cells. Pipetting is done gently using a pipette to break up the aggregates. Aggregates are not triturated. Rather, they are drawn into the pipette tip and then expelled without the tip being placed against the side of the vessel. This mild shear is enough to encourage the separation of the partially dissociated aggregates.

"Decreasing the pH" means lowering the pH to a less alkaline pH than in step (a). The decrease in pH may be provided by addition of acidic medium. The acidic medium optionally comprises medium and an acid. Examples of suitable acids include hydrochloric acid, sulphuric acid, acetic acid, citric acid, phosphoric acid, and carbonic acid. The pH is preferably decreased to a pH ranging from pH 7.0 to pH 8.5. The pH is most preferably about 8.1.

"Medium" means any cell culture medium in which the cells are capable of normal proliferation and is generally at a neutral pH. A person skilled in the art would be aware of the appropriate medium that would allow for proliferation of a specific cell type. Examples of medium for neural stem cells, mammary epithelial cells, porcine pancreatic stem cells include PPRF-m4; and any medium comprised of a basal medium (for example MEM, DMEM/F12, Iscove's, McKoy's, RPMI), supplemented with glucose, HEPES and sodium bicarbonate; and a proliferation supplement consisting of components such as Insulin, Apotransferin, Progesterone, Putrescine, Sodium Selenite, Pituitary Extracts (O'Connor et al., 1996).

The step of generating the single cell suspension is optionally for a finite period of time. In one embodiment, the finite period of time is between 7 and 10 minutes. This step may further comprise pipetting the medium after about 2 minutes and about 5 minutes have elapsed. After decreasing the pH, it is also useful to pipette the medium. Pipetting of the medium may be repeated numerous times, preferably 5 to 10 times per pipetting step.

Cell aggregates may have a variety of sources. In one embodiment, cell aggregates are selected from the group consisting of two cells, primary tissue, spheres of cells, aggregates of cells and clusters of cells. The cell aggregates may be pieces of animal tissue or cells in in vitro cell culture. The cells are optionally mammalian. Mammalian cell aggregates are optionally selected from the group consisting of neurospheres, embryonic neural stem cells, hematopoietic cells, mammary epithelial cells, pancreatic cells and cell lines such as CHO and BHK cells.

Chemical Detachment of Anchorage Dependent Cell Aggregates:

Cultured cells often form monolayers on a physical surface. Accordingly, the present invention provides a method for chemically detaching cells from a physical surface comprising the steps of:

a) increasing the pH of the medium in the presence of an chelating agent;

b) generating a single cell suspension; and c) decreasing the pH of the medium.

"Chemically detaching cells from a physical surface" includes both detachment of cells from the surface and dissociation between cells. The other terms are as defined previously.

The chelating agent can be any chelating agent that can assist in dissociating cells from the surface. Examples of chelating agents include, but are not limited to, ethylenediaminetetraacetic acid (EDTA), diethylenetriaminepentaacetic acid (DTPA); nitrilotriacetic acid (NTA); Dimercaprol; Metallothionein; and ethylene glycol bis($\beta$-aminoethyl ether)-N,N,N',N'-tetracetate (EGTA). The chelating agent is preferably EDTA.

The increase in pH may be provided by addition of alkaline medium. The alkaline medium optionally comprises proliferation medium and a base. Alternatively, the alkaline medium comprises phosphate buffered solution and a base. Examples of suitable bases include sodium hydroxide, potassium hydroxide, calcium hydroxide, ammonium hydroxide, zinc hydroxide, sodium phosphate tribasic dodecahydrate and sodium carbonate. The pH is preferably increased to a pH ranging from 9 to 11.5. The pH is most preferably about 10.

The generation of the single cell suspension may be achieved by rocking the culture vessel after the increase in pH in order to encourage cell detachment and by optionally gently pipetting the resulting detached cells. The gentle pipetting step may be repeated 5 to 10 times. Pipetting is gently done using a pipette to break up the aggregates. Aggregates are not triturated. Rather, they are drawn into the pipette tip and then expelled without the tip being placed against the side of the vessel. This mild shear is enough to encourage the separation of the partially dissociated aggregates. The single cell suspension may then be centrifuged prior to decreasing the pH of the medium.

Decreasing the pH may be provided by placing cells in fresh medium which is at neutral pH. Alternatively, the decrease in pH may be provided by addition of acidic medium. The acidic medium optionally comprises medium or PBS, and an acid. Examples of suitable acids include hydrochloric acid, sulphuric acid, acetic acid, citric acid, phosphoric acid, and carbonic acid. The pH is preferably decreased to a pH ranging from pH 7.0 to pH 8.5. The pH is most preferably about 8.1.

A person skilled in the art would understand the appropriate medium for a specific cell type. Medium for CHO cells, L-929 Fibroblast cells and murine embryonic stem cells may be DMEM with FBS. DMEM is a commercially available basal medium that may be substituted for one or a combination of other types of basal media (e.g. F10, F12, RPMI, IMDM, MEM, McKoy's etc.) in certain cases.

The step of generating the single cell suspension is optionally for a finite period of time. In one embodiment, the finite period of time is 15 to 25 minutes. Mild pipetting up and down may aid in the dissociation of clumps of cells that have detached from a surface. The step of generating single cell suspension optionally further comprises rocking the cells gently for 2 to 5 minutes to detach the cells and then also optionally comprises pipetting the cells after 15 to 25 minutes to dissociate cells into single cell suspension.

Cell aggregates may have a variety of sources. In one embodiment, cell aggregates are selected from the group consisting of two cells and monolayers. The cell aggregates may be cells in in vitro cell culture. The cells are optionally mammalian. Mammalian cell aggregates are optionally selected from the group consisting of Chinese Hamster Ovary cells, L-929 murine lung fibroblast cells, murine mammary embryonic stem cells, MRC-5, He La, Vero, and MDCK.

Cells of the Invention:

The generation of single cell suspensions from cell aggregates and cells attached to surfaces is extremely important for a variety of applications. Since mechanical dissociation is manual in nature, dissociation efficiency varies between individuals, making it difficult to compare values from different sources. In fact, the manual nature of this procedure may contribute to differences in the measured cell density and viability between two identical samples. Enzymatic dissociation can also result in cell death or cell damage, although the damage is often not readily evident until the cells are subcultured and display significantly reduced proliferation levels.

The present invention allows for aggregates of cells, including cells embedded in ECM to be removed from this matrix with minimal damage and destruction to the cells. The invention also allows for cells attached to a surface to be removed from a surface with minimal damage and destruction to the cells. Therefore the methods of the invention produce cells that are optimal for functioning and culturing.

Accordingly, the present invention provides for chemically dissociated cells resulting from the methods of the invention.

Uses of the Cells of the Invention (i) Clonal Analysis

Stem cells are capable of both self-renewal and multilineage differentiation. Stem cells give rise to non-self-renewing progenitors that are limited in their ability to differentiate. Despite the importance of understanding stem cell proliferation, the mechanisms that control their proliferation and differentiation are still relatively unknown because of the difficulties in culturing and studying these cells. However, the present invention provides improved cells that are optimal for culture conditions.

Accordingly, the present invention includes the use of the cells of the invention for clonal analysis.

(ii) FACS Analysis

Fluorescence-activated cell sorter (FACS) is used in flow cytometry to separate and identify specific cell types. In order for surface protein on cells to be able to react with the monoclonal antibodies the cells must be dissociated from cell aggregates in cell culture. Furthermore, to obtain accurate measurements of each cell type, cell death in culture must be minimized.

Accordingly, in a further embodiment, the present invention includes the use of the cells of the invention for FACS analysis. One skilled in the art would understand the appropriate monoclonal antibodies to be used to separate and identify particular cell types.

(iii) Cell Culture

The present invention also includes the use of the cells of the invention for both short term and long term in vitro cell culture. "Short term" in vitro cell culture means that the cells are only plated once after isolation of the cells. "Long term" in vitro cell culture means that the cells have been replated and subcultured at least one time. In vitro cell culture according to the invention would be useful for the study of stem cells, including neural, pancreatic, mammary, mesenchymal and embryonic stem cells.

(iv) Cellular Therapy

There are many medical conditions arising from the loss of cell number or function where cellular therapies could be employed. Accordingly, in a further embodiment, the present invention includes the use of the cells of the invention for cellular therapy.

These therapies may involve employment of autologous, allogeneic, or xenogeneic cells. Cellular therapies involve administering cells to a mammalian host, where the cells are to remain viable and functional, usually substituting for or interdigitating with the cells of the host. Similarly, modified cells may be used in cellular therapies. For example, cells altered to reduce immunogenicity; cells altered to produce therapeutic compounds, either naturally occurring or mutated, such as cytokines, hormones, clotting factors, anti-clotting factors, growth hormones, colony stimulating factors, interferons, immunosuppressants, etc.; cells altered to be resistant to infection with microorganisms, viruses or other pathogens; and cells altered to be capable of homing to targeted sites of malignant or infectious disease processes may be used.

Cells of particular interest include, among other lineages, the islets of Langerhans, adrenal medulla cells which may secrete dopamine, osteoblasts, osteoclasts, epithelial cells, endothelial cells, T-lymphocytes, neurons, glial cells, ganglion cells, retinal cells, liver cells, bone marrow cells, mesenchymal, endothelial and myoblast (muscle) cells.

In the case of islets of Langerhans, they may be grown and introduced into capsules or otherwise for insertion into a host for the production of insulin. In the case of retinal epithelial cells, they may be injected into the subretinal space of the eye to treat visual disorders, such as macular degeneration. In the case of immune cells, they may be injected into the bloodstream or elsewhere to treat immune deficiency or to augment immunity. In the case of myoblasts, they may be injected at various sites to treat muscle wasting diseases, such as Duchenne muscular dystrophy. In the case of cells genetically modified for other purposes, for example, to produce therapeutic compounds, to target malignant or infectious disease processes, or to be resistant to pathogens, similar methods of administration will be employed.

Diseases or disease states which may be treated by the cells of the invention include skin trauma or ulcers, burns, neoplasia, infections due to viruses, particularly in an immunodeficiency setting, muscle wasting syndrome, endocrine disorders due to insulin or growth hormone deficiency, hepatic injury or infection, degenerative diseases of the eye, such as macular degeneration or retinitis pigmentosa, etc. or the nervous system, such as Parkinson's disease, Alzheimer's disease, etc.

(v) Production of Bio-molecules

The methods of the present invention were found to be superior for the simultaneous dissociation of large quantities of aggregates, making it ideal for handling cells from scaled-up cultures. Accordingly, in another embodiment, the present invention includes the use of the cells of the invention for production of bio-molecules.

Kits:

The reagents suitable for carrying out the methods of the invention may be packaged into convenient kits providing the necessary materials, packaged into suitable containers. Such kits may include all the reagents required to produce chemically dissociated cells by means of the methods described herein, and optionally suitable supports useful in performing the methods of the invention.

Accordingly, in an embodiment of the invention, the kit includes alkaline medium for increasing the pH, acidic medium for decreasing the pH and instructions for use. The kit may be designed for specific cell types. One of skill in the art could easily modify the steps and reagents in the kit, for example, the number of pipetting times, the timing of the pipetting step, the optimal dissociation pH and the degree of increase or decrease in pH, for a particular cell type.

The following non-limiting examples are illustrative of the present invention:

EXAMPLES

Materials and Methods

Chemical Dissociation of Cellular Aggregates

Figure 3:
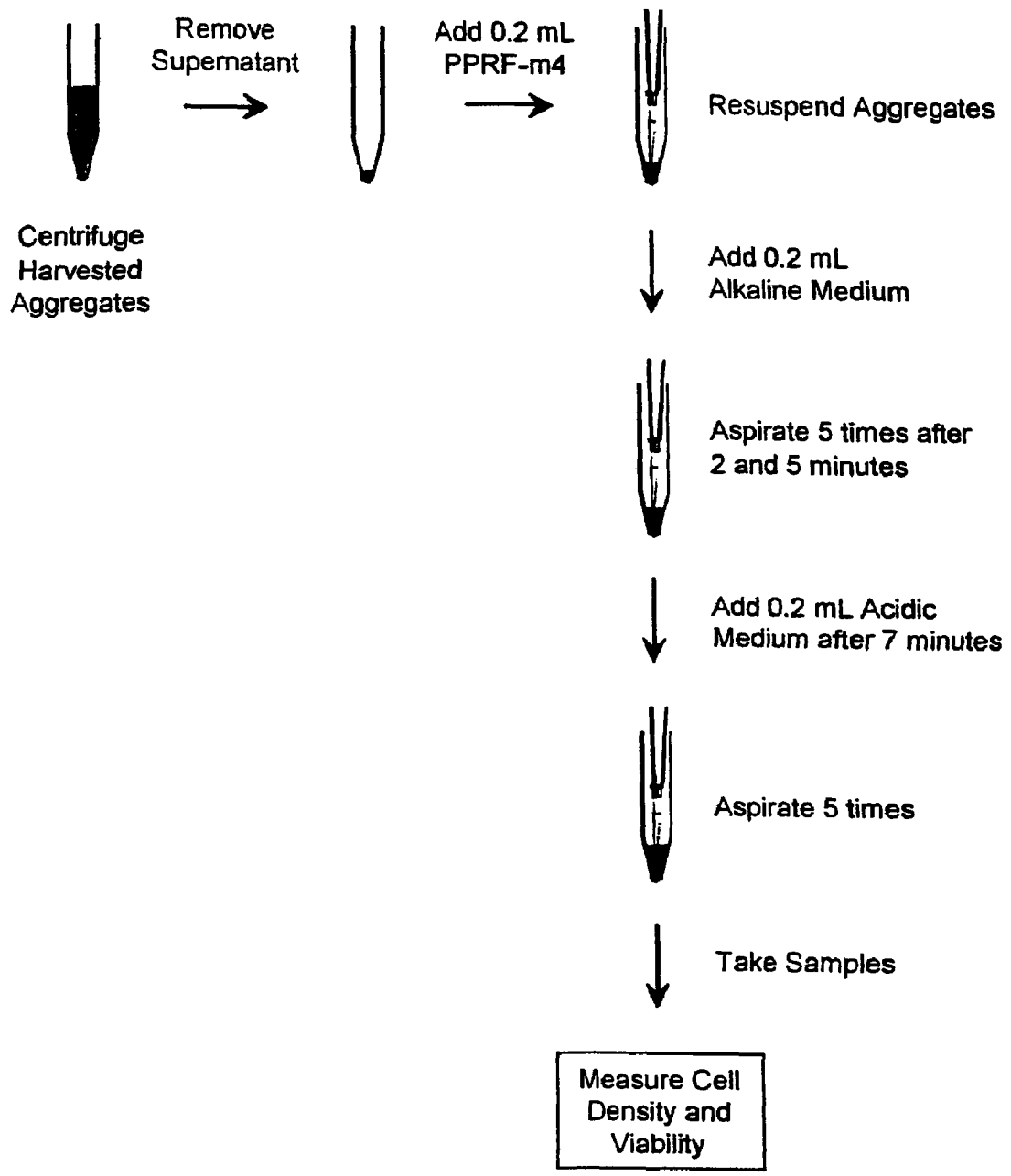
FIG. 3 shows a schematic representation of the protocol developed to dissociate mouse aggregates chemically. Harvested aggregate samples were centrifuged, and all of the supernatant was removed. The dissociation process was initiated when alkaline medium was added, and the contents of the tube were gently pipetted 5 times at 2 minutes and 5 minutes. After 7 minutes had elapsed, acidic medium was added to lower the pH, and the contents were gently pipetted 5 more times. The cell concentration and viability of the resulting single cell suspension were measured using trypan blue exclusion.

Dissociation of a population of cell aggregates into a single cell suspension involved a two-step protocol. This is schematically depicted in FIG. 3. Briefly, harvested aggregates were centrifuged (10 minutes, 140 g) to form a cell pellet in a 15 mL centrifuge tube. The supernatant was completely removed. The aggregates were then resuspended in 200 µL of fresh PPRF-m4 medium or any proliferation medium comprised of for example, a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996), at room temperature by pipetting the cell pellet 5 times. Two hundred (200) µL of an alkaline medium comprising 1 mL of 1.0 N NaOH added to 20 mL of neural proliferation medium (preferably PPRF-m4 medium) was then added to the tube, and a stopwatch was used to time the procedure for 7 minutes. After 2 minutes and 5 minutes had elapsed, the cells were gently pipetted 5 times. After 7 minutes, 200 µL of the acidic medium comprised of mixing 1 mL of 1.0 N HCl into preferably 20 mL of PPRF-m4 medium, was added to the mixture to decrease the pH, and the sample was gently pipetted 5 more times. This procedure reliably resulted in a single cell suspension. This novel chemical dissociation procedure is efficient, cost effective, and not manually intensive.

Chemical Dissociation of Cells Attached to a Surface

Anchorage dependent cells were grown in 25 cm$^2$ Nunc tissue culture flasks for two days or until confluence was reached. The tissue culture flasks were removed from the 37° C. incubator and placed into a sterile laminar flow hood. The medium was carefully removed from each tissue culture flask using a 2.0 mL pipette, and the adherent cells were carefully rinsed twice with phosphate buffered saline solution. 2 mL of a chemical dissociation solution was then added to each flask. The chemical dissociation solution was generated by adding 25 µL of 1.0 N NaOH to 2 mL of phosphate buffered saline solution containing EDTA, preferably in an amount from about 5 mM-20 mM, more preferably 10 mM. The tissue culture flasks were rocked intermittently. After 2-5 minutes (depending on the cell type), the cells were observed to detach from the surface in sheets or clumps. The detached sheets and clumps of cells were maintained in the chemical dissociation solution until gentle pipetting (10 times) using a 1 mL pipette resulted in a single cell solution. This procedure reliably resulted in a single cell suspension. This novel chemical dissociation procedure is efficient, cost effective, and not manually intensive.

The two-step dissociation protocols detailed above were applied for specific types of cell aggregates. For application of the protocol to other cell aggregate types, one of skill in the art could easily modify the steps in the protocol, for example, the number of pipetting times, the timing of the pipetting step, the optimal dissociation pH and the degree of increase or decrease in pH.

Example 1

Passaging of Embryonic Mouse Neurospheres

Neural cells can be obtained from primary embryonic, post-natal or adult CNS tissue from any region of the neuroaxis including but not limited to the striatum, septum, cortex, ventral mesencephalon, midbrain, cerebellum or spinal cord from murine, rodent and human. Neural cells can also be obtained from cultured cells such as those generated using the Neurosphere Assay or any method known to one skilled in the art of neural tissue culture. Neural cells can also be obtained from any stage of embryonic stem cell cultures according to any standard procedure for culturing ES cells.

Figure 4:
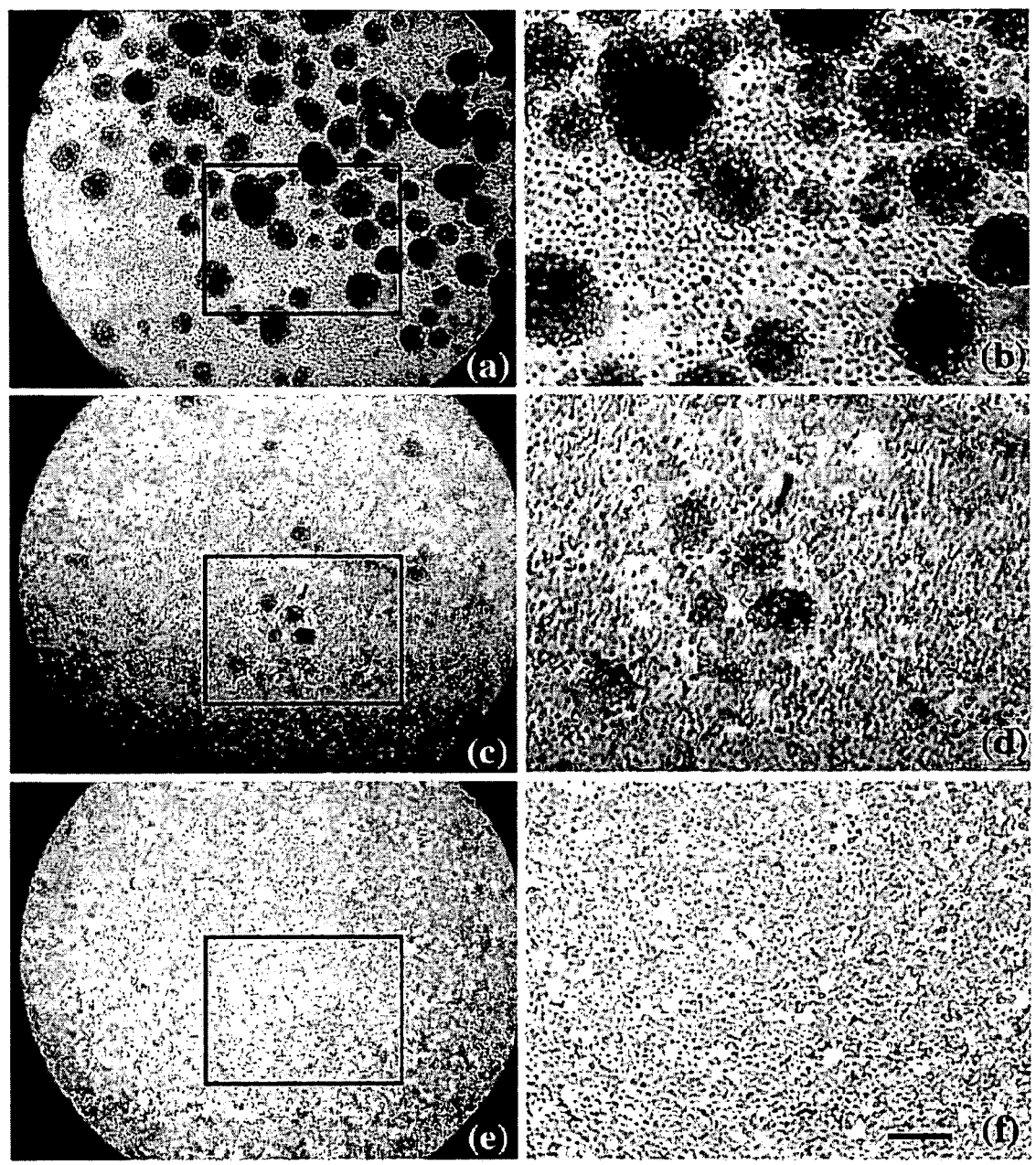
FIG. 4 are photomicrographs showing the chemical dissociation of mouse neural cell aggregates at (a) 2 minutes (c) 5 minutes, and (e) 7 minutes after the addition of the alkaline medium. FIGS. (b), (d) and (f) are enlargements of the boxed areas in FIGS. (a), (c), and (e) respectively. It is evident that alkaline treatment together with mild pipetting resulted in the dissociation of aggregates into the single cell suspension shown in (e) and (f). Scale bars represent 150 µm.

For example, striata and/or cortex were dissected from Embryonic Day 14 CD1 albino mouse embryos (Charles River) using standard microdissection techniques. Tissue was collected in phosphate-buffered saline with 2% glucose then mechanically dissociated using a fire-polished glass pipette into a single cell suspension, washed once and resuspended in complete NeuroCult™ medium (NeuroCult® Basal Medium & NeuroCult™ Proliferation Supplements; StemCell Technologies Inc.) with 20 ng/ml of EGF (20 ng/mL plus 10 ng/mL for rat cells). Mouse cells were cultured for 7 days, while rat cells were cultured for 4 days. At the end of the culture period, rat and mouse neurospheres were harvested, dissociated into single cell suspensions by mechanical dissociation or by the 2-step pH change protocol of the present invention. The 2-step protocol involves dissociating a population of neural stem cell (NSC) aggregates into a single cell suspension. This is schematically depicted in FIG. 4. Briefly, harvested aggregates were centrifuged (10 minutes, 140 g) to form a cell pellet in a 15 mL centrifuge tube. The supernatant was completely removed. The aggregates were then resuspended in 200 µL of fresh PPRF-m4 medium or any neural proliferation medium comprised of a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996), at room temperature by pipetting the cell pellet 5 times. 200 µL of an alkaline medium comprising 1 mL of 1.0 N NaOH added to 20 mL of neural proliferation medium (preferably PPRF-m4 medium) was then added to the tube, and a stopwatch was used to time the procedure for 7 minutes. After 2 minutes and 5 minutes had elapsed, the cells were gently pipetted 5 times. After 7 minutes had elapsed, 200 µL of the acidic medium comprised of mixing 1 mL of 1.0 N HCl into preferably 20 mL of PPRF-m4 medium, was added to the mixture to decrease the pH, and the sample was gently pipetted 5 more times. Total viable cells were counted based on Trypan blue exclusion. Cells can be passaged into secondary cultures after 5-7 days of culture.

Example 2

Effect of pH on Aggregate Morphology on Mouse Neurospheres

To determine if pH has an affect on the NSC aggregate morphology, several samples of aggregates from 4-day old T-flask cultures were isolated, subjected to a range of environmental pH values, and simply observed over time. Media with different pH values were generated by adding either 1.0 N HCl or 1.0 N NaOH to preferably PPRF-m4 medium or a neural stem cell proliferation medium comprised of a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996). Observations revealed that during the time course of the experiment, placing the aggregates in an acidic environment did not result in any significant degree of dissociation. Even after 30 minutes at a pH of 4, the aggregates remained intact, although the cells on the surface of the aggregate appeared rounder and more visible. This was not the case however, in the alkaline pH range. Up to a pH of 9, no obvious effects were observed upon the aggregates, even after 20 minutes. However, at a pH of 10, the cells on the surface of the aggregates became more visible over time, as though the ECM molecules surrounding them were dissolving. At a pH of 12, the aggregates were almost completely wiped out within a few minutes. Aggregates appeared as loosely clumped groups of a few cells, and most of the cells had disappeared indicating that this pH was actually destroying the cells. Beyond a pH of 12, the cells were almost instantly dissolved, leaving behind what appeared to be the remnants of aggregates.

Based on the observation that NSC aggregates appeared to lose their physical integrity when exposed to alkaline conditions, a pH based chemical dissociation method was developed. A target pH of 10 was chosen since at this pH, although the aggregates definitely appeared to be dissociating, the cells appeared to remain intact. An alkaline medium with a pH of approximately 11.6 was produced by adding 1 mL of 1.0 N NaOH to 20 mL of preferably PPRF-m4 medium or a neural stem cell proliferation medium comprised of a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996). When the alkaline medium was mixed with an equal volume of fresh PPRF-m4 medium (pH 7.5) at room temperature, the resulting dissociation medium had a pH of approximately 10 (FIG. 3). Aggregates were placed in this dissociation medium and gently pipetted with a 200 µL pipette tip to break-up the aggregates. It should be noted that the aggregates were not triturated. Rather, they were drawn into the pipette tip and then expelled without the tip being placed against the side of the vessel. This mild shear was enough to encourage the separation of the partially dissociated aggregates. Through rigorous experimentation, it was determined that a single cell suspension could be achieved at a pH of 10 by pipetting the aggregates 5 times at 2 minutes, 5 minutes, and 7 minutes after they were placed in the dissociation medium. Using this approach, the aggregates are completely dissociated into a single cell suspension within 7 minutes as shown in FIG. 4.

Maintaining mammalian cells for an extended period of time in an environment with an elevated pH is known to be detrimental (Martin and Wiley, 1994). To avoid adverse effects caused by long-term incubation at elevated pH, the pH of the medium was dropped to 7.5 using HCl. However, when this is done, the cells start to spontaneously re-associate before they could be counted or inoculated into a fresh culture. This indicated that the dissociation of the aggregates was caused by a reversible mechanism, most likely related to the electrostatic charges on the proteins in the ECM. Through extensive experimentation it was found that maintaining the cells in a medium that had a pH of 8.1 allowed the cells to re-associate at a much lower rate. From a practical standpoint, this was desirable since it allowed for enough time to measure cell concentration, viability, and to inoculate the cells as a single cell suspension into fresh medium. To lower the pH of the dissociation medium from 10 to 8.1, an acidic medium with a pH of approximately 1.7 was generated by mixing 1 mL of 1.0 N HCl into 20 mL of PPRF-m4 medium. The preferred protocol for dissociating neurospheres is hereby described in Example 3.

Example 3

Method of Dissociation of Neurospheres

Using the above solutions, a 2-step protocol was developed to dissociate a population of NSC aggregates into a single cell suspension. This is schematically depicted in FIG. 3. Briefly, harvested aggregates were centrifuged (10 minutes, 140 g) to form a cell pellet in a 15 mL centrifuge tube. The supernatant was completely removed. The aggregates were then resuspended in 200 µL of fresh PPRF-m4 medium at room temperature by pipetting the cell pellet 5 times. 200 µL of the alkaline medium was then added to the tube, and a stopwatch was used to time the procedure for 7 minutes. After 2 minutes and 5 minutes had elapsed, the cells were gently pipetted 5 times. After 7 minutes had elapsed, 200 µL of the acidic medium was added to the mixture to decrease the pH, and the sample was gently pipetted 5 more times. This procedure reliably resulted in a single cell suspension. This novel chemical dissociation procedure is efficient, cost effective, and not manually intensive.

Example 4

Comparison of Chemical Dissociation to Mechanical Dissociation for Mouse Neurospheres A. Viability & Cell Concentration The effect of chemical dissociation relative to mechanical dissociation was investigated with respect to cell viability and cell density. 48 mL of culture medium was removed from a day 4 spinner flask culture and placed in a 50 mL centrifuge tube. The contents of the tube were aliquotted into 10 centrifuge tubes, with 4.5 mL placed in each tube. The contents of the 50 mL tube were well mixed between aliquots to ensure that all samples were as similar as possible. All of the aliquots were centrifuged (10 min, 140 g), and the supernatant removed. Each cell pellet was then resuspended in 200 µL of fresh PPRF-m4 medium. Five of the samples were chosen at random and mechanically dissociated. The other five samples were chemically dissociated as per the protocol outlined in Example 3. Briefly the 2-step protocol involves dissociating a population of neurospheres into a single cell suspension. This is schematically depicted in FIG. 3. Briefly, harvested aggregates were centrifuged (10 minutes, 140 g) to form a cell pellet in a 15 mL centrifuge tube. The supernatant was completely removed. The aggregates were then resuspended in 200 µL of fresh PPRF-m4 medium or any neural proliferation medium comprised of a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996), at room temperature by pipetting the cell pellet 5 times. 200 µL of an alkaline medium comprising 1 mL of 1.0 N NaOH added to 20 mL of neural proliferation medium (preferably PPRF-m4 medium) was then added to the tube, and a stopwatch was used to time the procedure for 7 minutes. After 2 minutes and 5 minutes had elapsed, the cells were gently pipetted 5 times. After 7 minutes had elapsed, 200 µL of the acidic medium comprised of mixing 1 mL of 1.0 N HCl into preferably 20 mL of PPRF-m4 medium, was added to the mixture to decrease the pH, and the sample was gently pipetted 5 more times. The samples that were chemically dissociated ended up having a total volume of approximately 600 µL due to the additions of 200 µL of alkaline medium, and 200 µL of acidic medium. Thus, 400 µL of fresh PPRF-m4 medium was added to each of the mechanically dissociated samples to ensure that all samples had similar final volumes. The cell concentration and viability were determined.

Figure 5:
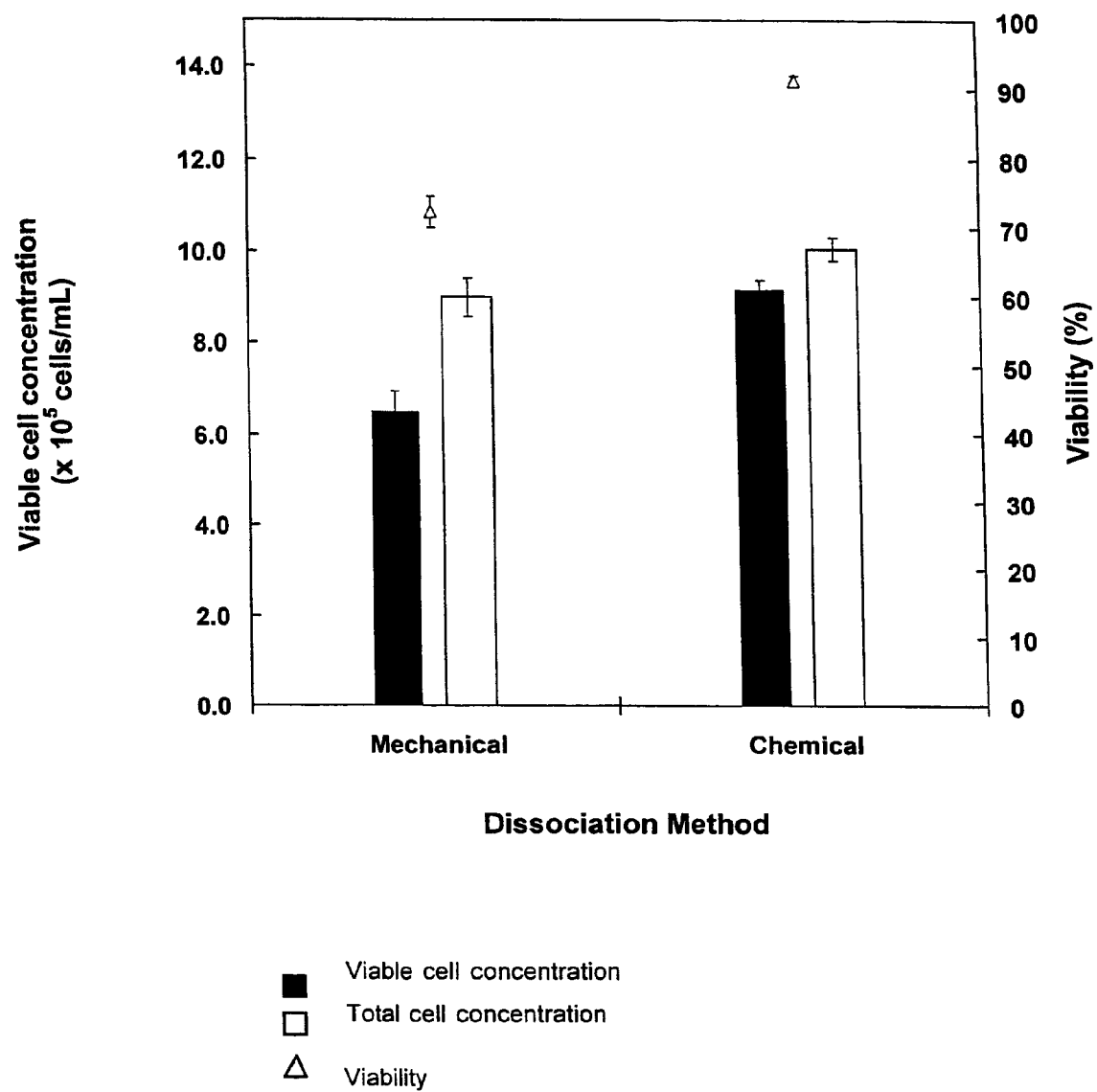
FIG. 5 shows average total and viable cell concentration, and the cell viability for five samples of mouse neural cells where aggregates (neurospheres) were dissociated mechanically (200 µL pipette tip) or chemically. The error bars are the standard deviation from the mean. The aggregate samples were isolated from a 125 mL day 4 spinner flask culture. The viable cell concentration achieved using mechanical dissociation was significantly lower than that obtained by chemical dissociation ($p<0.001$, $n=5$). Moreover, the viability obtained using mechanical dissociation was also significantly lower ($p<0.001$, $n=5$).

It is evident from FIG. 5 that the average viability of the chemically dissociated cultures (91.4±0.7%) was significantly higher than that measured in the mechanically dissociated cultures (72.4±2.4%). Furthermore, the average viable cell concentration achieved using chemical dissociation was over 40% higher than that achieved using mechanical dissociation. It is notable that the standard deviation measured for chemical dissociation ($0.21 \times 10^5$ cells/mL) was considerably smaller than that for mechanical dissociation ($0.44 \times 10^5$ cells/mL) suggesting that chemical dissociation may be a more reproducible procedure than mechanical dissociation for the determination of viable cell concentration. Also shown in FIG. 5 is the total cell concentration. The average total cell concentration for the chemically dissociated cultures was $10.1 \times 10^5 \pm 0.2 \times 10^5$ cells/mL. The 12% higher total cell concentration in the latter case suggests that mechanical dissociation not only kills a significant proportion of otherwise viable cells within neurosphere aggregates, but that a percentage of them are completely destroyed. Since these cells are no longer intact, they are not taken into account when determining viability. Overall, these results indicate that chemical dissociation is superior to mechanical dissociation for creating a single cell suspension from small populations of NSC aggregates.

B. Lactate Dehydrogenase Activity

Figure 6:
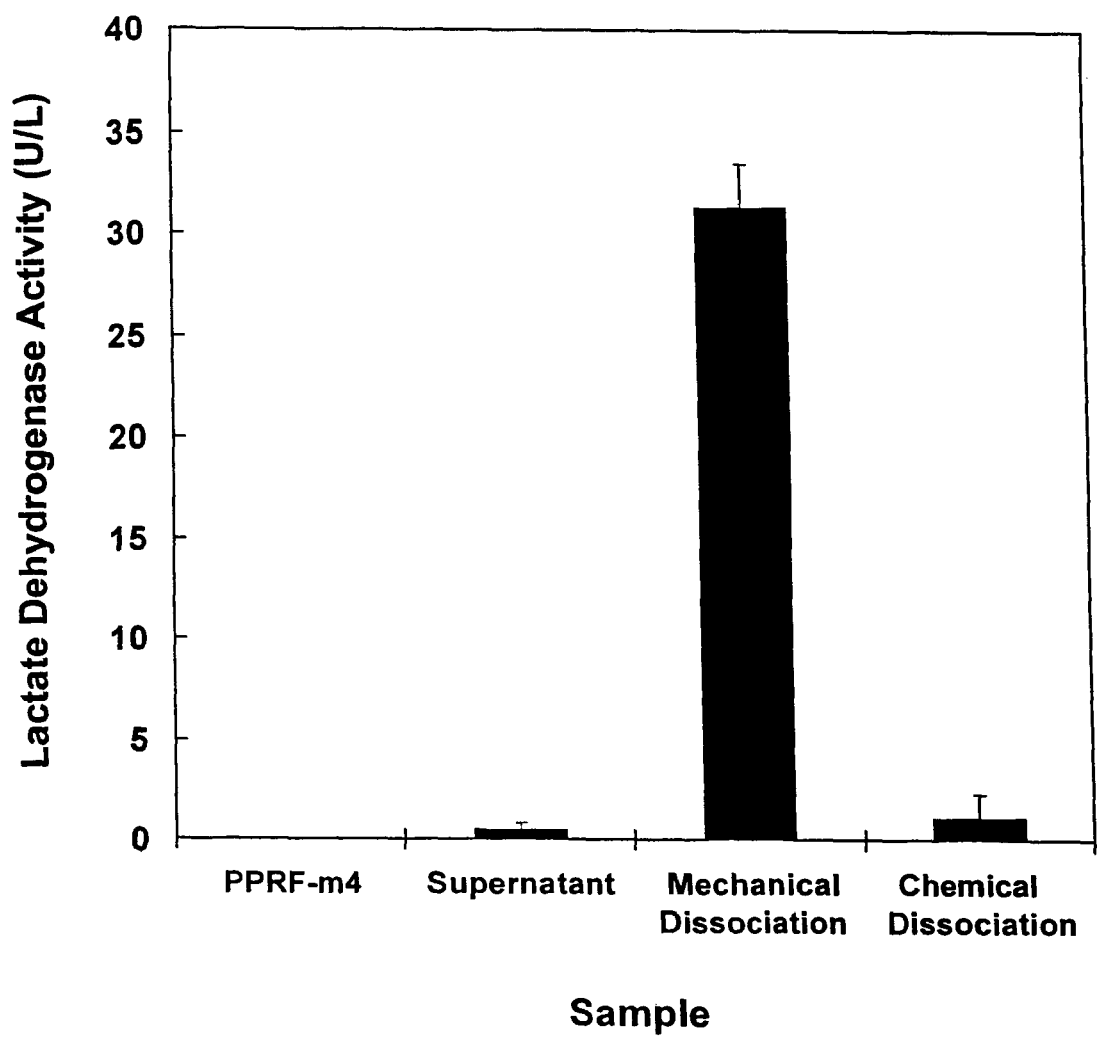
FIG. 6 shows lactate dehydrogenase (LDH) activity associated with the chemical and mechanical dissociation of mouse neural cell aggregates. Also included are LDH activity values for fresh PPRF-m4 medium and the culture supernatant prior to dissociation. The error bars are the standard deviation from the mean. The LDH released by mechanically dissociating the aggregates was significantly higher than the background levels in the supernatant ($p<0.001$, $n=5$). However, the levels of LDH released by chemical dissociation could not be distinguished from background levels ($p=0.39$, $n=5$).

To determine if alkaline treatment was destroying dead cells, increasing the proportion of viable cells but not the total number of viable cells relative to mechanical methods, Lactate Dehydrogenase Activity (LDH) activity was measured before and after dissociation. Results are summarized in FIG. 6. Aggregates harvested from T-flasks were centrifuged, and all but 200 µL of the supernatant was removed from each sample. The supernatant was analyzed for LDH activity, which was found to be very low. Also included in this experiment were measurements of LDH in fresh PPRF-m4 medium. As expected, no LDH activity was found. LDH activity was measured after dissociation using both methods. It is evident that mechanical dissociation resulted in intracellular LDH being released into the environment. The LDH released due to chemical dissociation could not be distinguished from pre-dissociation levels. To ensure that the near lack of LDH activity (IU/L) in chemically dissociated cultures was not the result of enzyme inactivation due to alkaline treatment, LDH activity in samples was measured prior to and after intentional modification of pH. It was found pH did not have a significant effect on LDH activity in the range tested (results not shown). This was not surprising as the LDH assay is normally carried out using an alkaline buffer.

C. FACScan Analysis

Figure 7:
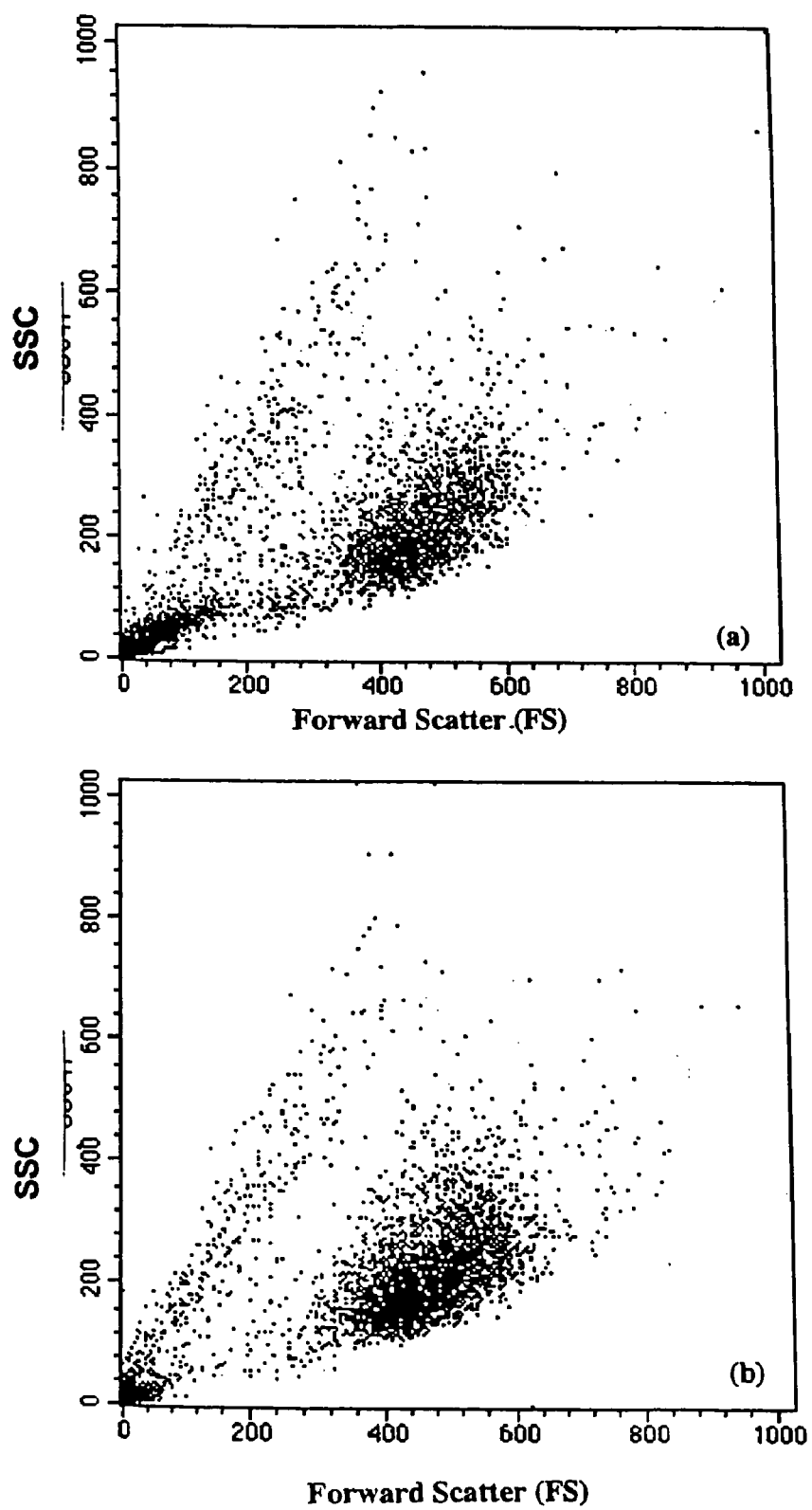
FIG. 7. Flow cytometric analysis of mouse neural cell aggregates after mechanical or chemical dissociation showing forward scatter (FS) and side scatter (SS) data. Forward scatter is a measure of cell size, and side scatter is a measure of cellular granularity. Shown are the results for (a) mechanical dissociation and (b) chemical Dissociation.
Figure 8:
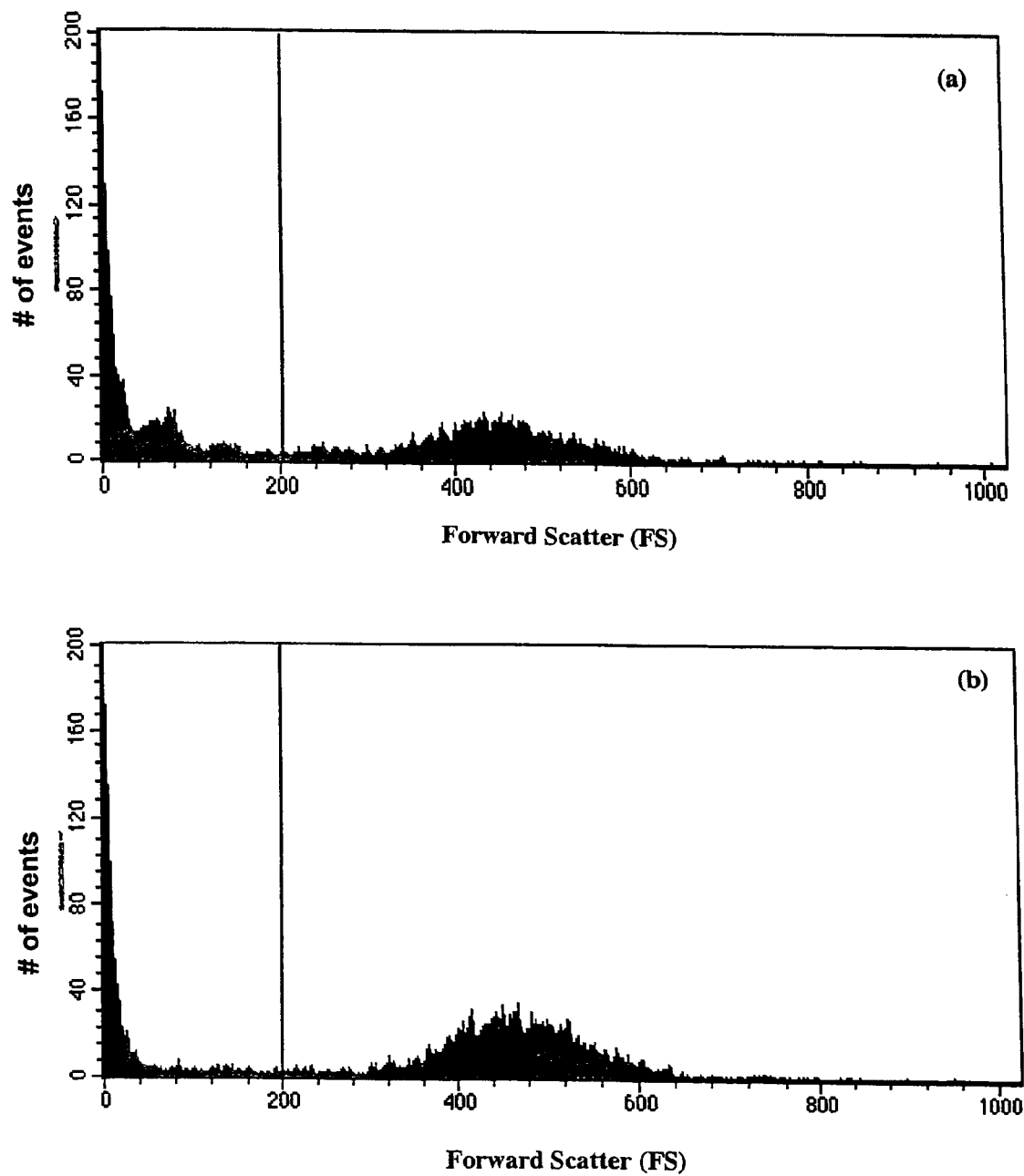
FIG. 8 Histogram presentation of the data from FIG. 7 showing the number of cells in the analyzed sample at each FS value. Shown are the values for (a) Mechanical Dissociation and (b) Chemical Dissociation. Each plot has been divided into a region containing debris (FS<200) and a region of viable cells (FS≧200).

A visual reduction in debris formation was observed when using the chemical dissociation method versus the mechanical dissociation method. As debris arises in cultures due to cell destruction, mechanically and chemically dissociated samples were analyzed using a Becton Dickinson FACScan. The results of this study are shown in FIGS. 7 and 8. FIG. 7 shows graphs with forward scatter (FS) on the x-axis, and side scatter (SS) on the y-axis. Forward scatter is correlated with cell size, whereas side scatter is an indication of cellular granularity. Each data point corresponds to an individual particle analyzed by the FACScan. Three things are evident in FIG. 7. First is the quantity of debris. Since debris is small, it appears on the graphs as data points with FS values lower than 200 (Alam, 2003). The number of data points below this value in the mechanically dissociated sample is significantly greater than the number of data points in the same range for the chemically dissociated samples (see Table 1), indicating less debris formation. This conclusion can be more easily drawn when the FS data in FIG. 7 is replotted in a histogram format as shown in FIG. 8. The number of particles with FS values below 200 is significantly greater after mechanical than chemical dissociation. The second item of note in these figures is the number of particles (cells) that lie in the area gated by 300<FS<600 and 100<SS<400. It is evident, both from the dot plots and the histograms, that there were a greater number of cells within this region after chemical dissociation, than after mechanical dissociation. The cells that were missing after mechanical dissociation were presumably destroyed, and responsible for the large amount of observed debris, and the measured LDH activity. The third item of note is the number of particles in the range FS>600. From FIG. 8, it is clear that the number of particles remaining in this range following chemical dissociation was greater than following mechanical dissociation. As previously mentioned, shear is more detrimental to large cells since they experience more torsion than small cells. It is likely that when undergoing mechanical dissociation, many of the larger cells perished. This is undesirable when growing a heterogeneous population of cells. Certain subpopulations may play key roles in maintaining and promoting NSC replication. Recently, Murayama and colleagues (2002) performed fluorescence activated cell sorting on populations of neural cells and determined that neural stem cells (those cells with the highest nestin-enhancer activity) were significantly concentrated in the fraction containing the largest cells (diameter of approximately 20 μm). Overall, these FACScan results suggest that the proposed chemical approach is greatly superior to the mechanical method of dissociating neural stem cell aggregates.

Example 5

Large Scale Dissociation of Mouse Neurospheres

The results presented so far have been for the dissociation of relatively small samples of aggregates (<5×10$^6$ cells). However, a critical problem when developing scale-up protocols for neurosphere cultures is how to handle large quantities of neurosphere aggregates. When neurosphere populations are passaged in small T-flasks, this is not a concern. However, when scaling-up a production system, it will be necessary to handle increasingly larger quantities of cells for subsequent inoculation (as a single cell suspension) into larger and larger bioreactors. Also, it may be necessary to dissociate large quantities of neurosphere aggregates for certain applications. Currently, large quantities of neurosphere aggregates from spinner flask cultures are dissociated mechanically using one of two approaches. In the first approach, a large volume of cell culture (45 mL) is placed in a 50 mL centrifuge tube and centrifuged to generate a large cell pellet. This large cell pellet is then triturated using a pipette, but always provides less than desirable results. The large quantity of aggregates cannot be broken up with 30 triturations and often the number of triturations to generate a single cell suspension. The excessive number of triturations significantly decreases culture viability, and results in the presence of large quantities of cellular debris. In the second approach, the 45 mL culture sample would be aliquotted into ten 15 mL centrifuge tubes. Following centrifugation, the contents of each tube would be mechanically dissociated, and then the single cell suspension in all of the tubes would be combined. While this approach works, it is time consuming, extremely labour intensive and prone to reliability issues. If generating inoculum for a large bioreactor, this approach could not be handled by one person, but would require the efforts of several individuals in order to be technically feasible.

Chemical dissociation was evaluated for its ability to dissociate large numbers of neural aggregates simultaneously. Samples (45 mL) from day 4 spinner flask cultures were placed in centrifuge tubes, centrifuged, and then dissociated either mechanically or chemically. Chemical dissociation was achieved by removing all of the supernatant, and resuspending the pellet in 2 mL of preferably fresh PPRF-m4 medium or a neural proliferation medium comprised of a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996). To this, 2 mL of alkaline medium was added, and a stopwatch was used to time the entire procedure (10 minutes). The contents were gently pipetted (not triturated) 10 times using a 1 mL pipette tip at 2 minutes and 5 minutes. At 7 minutes and 10 minutes, a 2 mL plastic pipette was used to pipette the contents 10 times. 2 mL of acidic medium was then added to lower the pH. It was also found that increasing the final volume of the solution to 20 mL using fresh PPRF-m4 medium decreased cell-cell interaction thereby allowing the single cell suspension to remain while the cell concentration and viability was being measured. Moreover, due to the large number of cells, this initial dilution allowed for a more accurate cell count.

Figure 9:
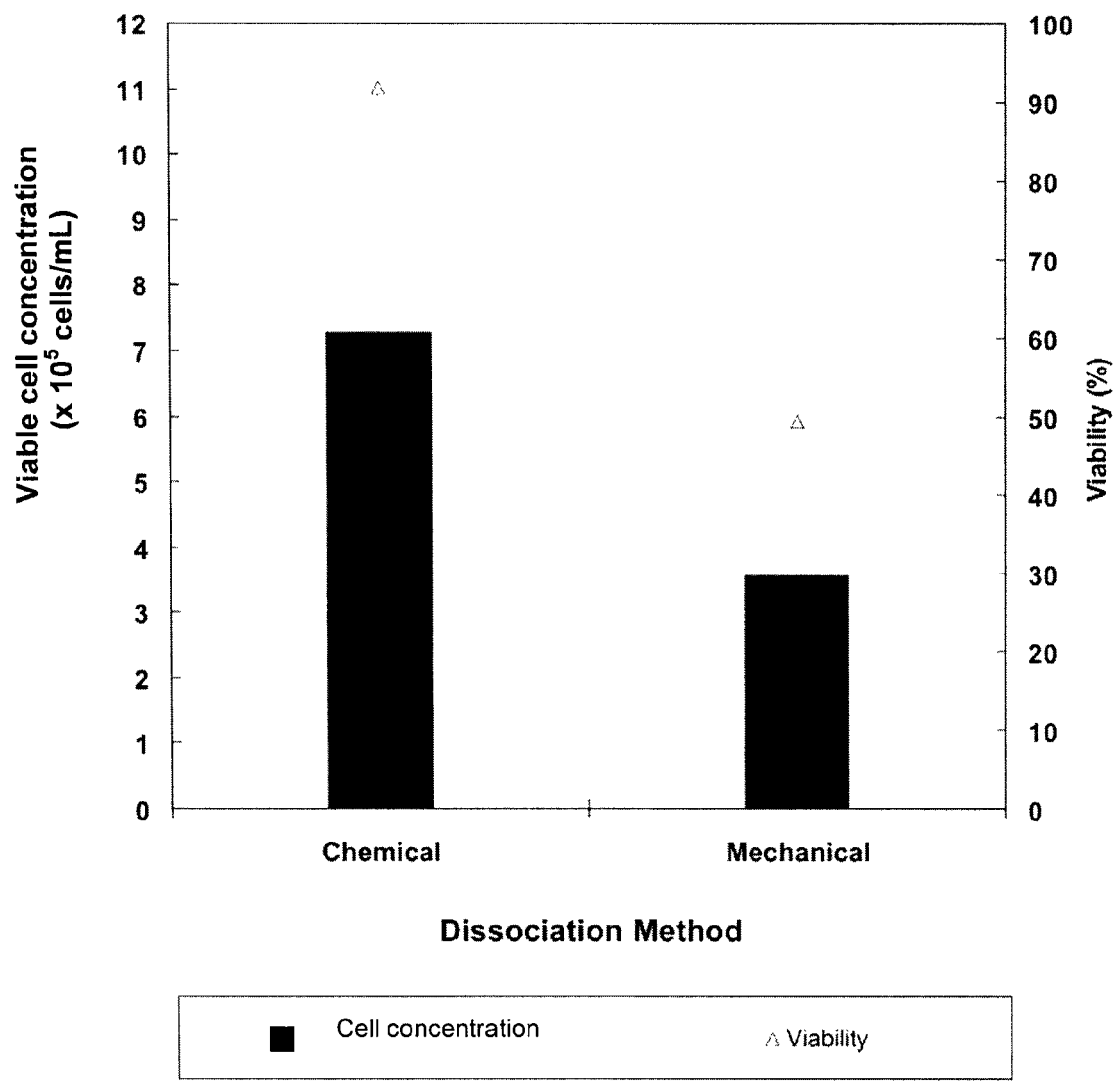
FIG. 9 shows viable cell concentration and cell viability of large quantities of neural cell aggregates from embryonic mouse CNS. Each sample of aggregates was derived from a 45 mL culture sample (day 4 in 125 mL spinner flasks). The samples were dissociated either chemically or mechanically. The error bars are the standard deviation from the mean. The chemical dissociation method resulted in significantly higher cell concentrations (p=0.0182; n=5) and viabilities (p=0.0053; n=5) over mechanical dissociation.

The results of this study are shown in FIG. 9. It is immediately evident that the chemical dissociation of the samples resulted in a viable cell concentration measurement that was more than double that obtained by mechanical dissociation. Post-dissociation cell concentration in the chemically dissociated sample was $7.3 \times 10^5 \pm 0.3 \times 10^5$ cells/mL whereas in identical samples dissociated mechanically, the viable cell concentration was $3.6 \times 10^5 \pm 0.4 \times 10^5$ cells/mL. Moreover, the average viability of 91.9±1.2% obtained chemically was significantly greater than the 49.4±2.9% obtained mechanically. When visualized under the microscope, much less debris was observed in the chemically dissociated samples. Overall, the results of these experiments suggest that chemical dissociation is a significant advancement for dissociating large quantities of NSC aggregates. The method is efficient, not manually intensive, and results in high viable cell concentration and viabilities.

Example 6

Growth Kinetics of Mouse Neurospheres in Spinner Flasks

The growth kinetics of cells that had undergone chemical dissociation were evaluated in comparison to cells that had been mechanically dissociated. Cells that had been dissociated using one of the two methods were inoculated into 125 mL spinner flasks containing 100 mL of preferably PPRF-m4 medium or a neural proliferation medium comprised of a Basal Medium containing, DMEM/F12, glucose, HEPES and sodium bicarbonate; and a proliferation supplement consisting of Insulin, Apo-transferin, Progesterone, Putrescine, Sodium Selenite (O'Connor et al., 1996). Two samples were drawn daily from each of the flasks, in order to evaluate cell concentration and viability as a function of time. One of the samples was dissociated mechanically, and one was dissociated chemically. For ease of explanation, a two letter system was used to keep track of the samples. The first letter referred to the inoculum of the flask. If the sample was drawn from a flask that had been inoculated using mechanically dissociated cells, then the first letter was "M". If the samples were from flasks that had been inoculated with chemically dissociated cells, then the first letter was 'C'. The second letter was used to indicate the method used to dissociate the drawn sample. If the sample was dissociated mechanically, the second letter was 'M'. If the sample was dissociated chemically, the second letter was 'C'. For example, the designation 'M-C' refers to a chemically dissociated sample that was drawn from a flask inoculated with mechanically dissociated cells. Similarly, 'C-M' refers to a mechanically dissociated sample taken from a flask inoculated with chemically dissociated cells.

Figure 10:
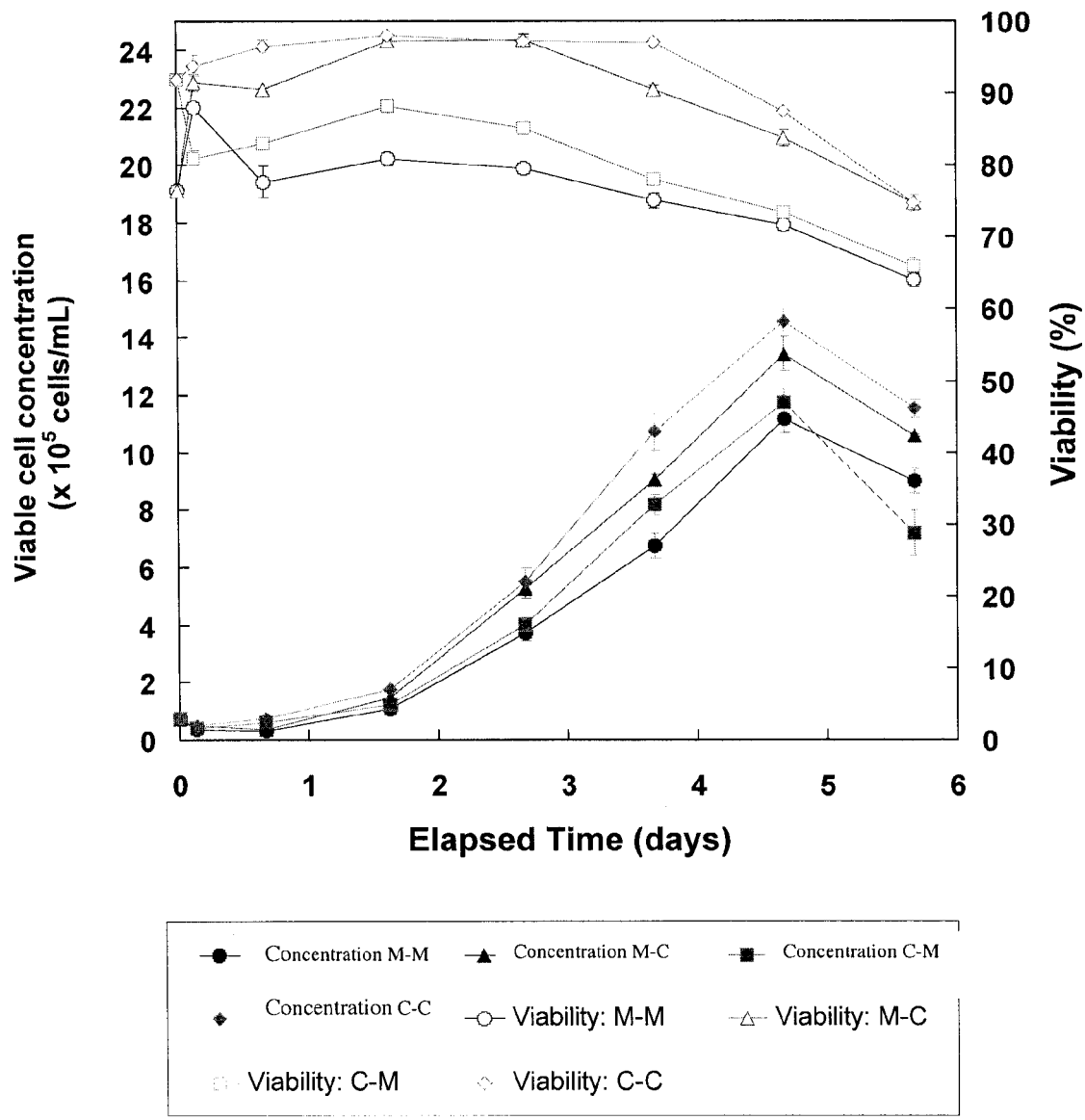
FIG. 10 shows viable cell concentration and cell viability of mouse neural cells that were serially subcultured in 2 sets of spinner flask experiments. The first set involved inoculating the spinner flasks with cells from mechanically dissociated neurospheres, and the second set involved inoculating spinner flasks with cell from chemically dissociated neurospheres. The spinner flasks were incubated at 37° C. in 5% $CO_2$ and agitated at 100 rpm. Samples were taken periodically from each set of experiments and dissociated either mechanically or chemically. The mechanically and chemically dissociated samples from set 1 were labeled M-M and M-C respectively. The mechanically and chemically dissociated samples from set 2 were labeled C-M and C-C respectively. The error bars are the standard deviation from the mean (n=3).

The results from this experiment are shown in FIG. 10. Samples were taken from the flasks every 24 hours, dissociated, and analyzed using trypan blue exclusion. Four distinct growth curves were generated, each displaying a maximum cell concentration approximately 5 days post inoculation. First, those samples drawn from the flasks inoculated with mechanically dissociated cells are discussed. It is obvious that the choice of sample dissociation method had an effect on the measured cell concentration and viability. When the samples were dissociated mechanically (M-M), the average maximum measured cell concentration was $11.2 \times 10^5 \pm 0.5 \times 10^5$ cells/mL, whereas when dissociated chemically (M-C), the average maximum cell concentration was $13.5 \times 10^5 \pm 0.6 \times 10^5$ cells/mL. Moreover, the measured viability was approximately 20% higher using chemical dissociation during the exponential phase of growth, although the gap did narrow to approximately 10% by day 6. It should be emphasized that the samples were taken from the same source, in the same manner, at the same time. The only difference was the method of dissociation used to break apart the aggregates.

The same trends were found in those samples drawn from spinner flasks inoculated with chemically dissociated cells. When the samples were dissociated mechanically (C-M), lower cell concentration and viabilities were measured throughout the run. The maximum cell concentration in the C-M samples was found to be $11.7 \times 10^5 \pm 0.5 \times 10^5$ cells/mL, whereas the chemically dissociated samples (C-C) had a maximum cell concentration of $14.6 \times 10^5 \pm 0.4 \times 10^5$ cells/mL. The C-C samples also exhibited greater than 90% cell viabilities throughout most of the run, which were substantially higher than those measured in the C-M samples. These results confirm that mechanical dissociation may underestimate true culture kinetics. It should be noted that on day 6, the aggregates appeared slightly more resistant to chemical dissociation. The problem was solved by increasing the number of pipetting times after 5 minutes and 7 minutes to 10.

Figure 11:
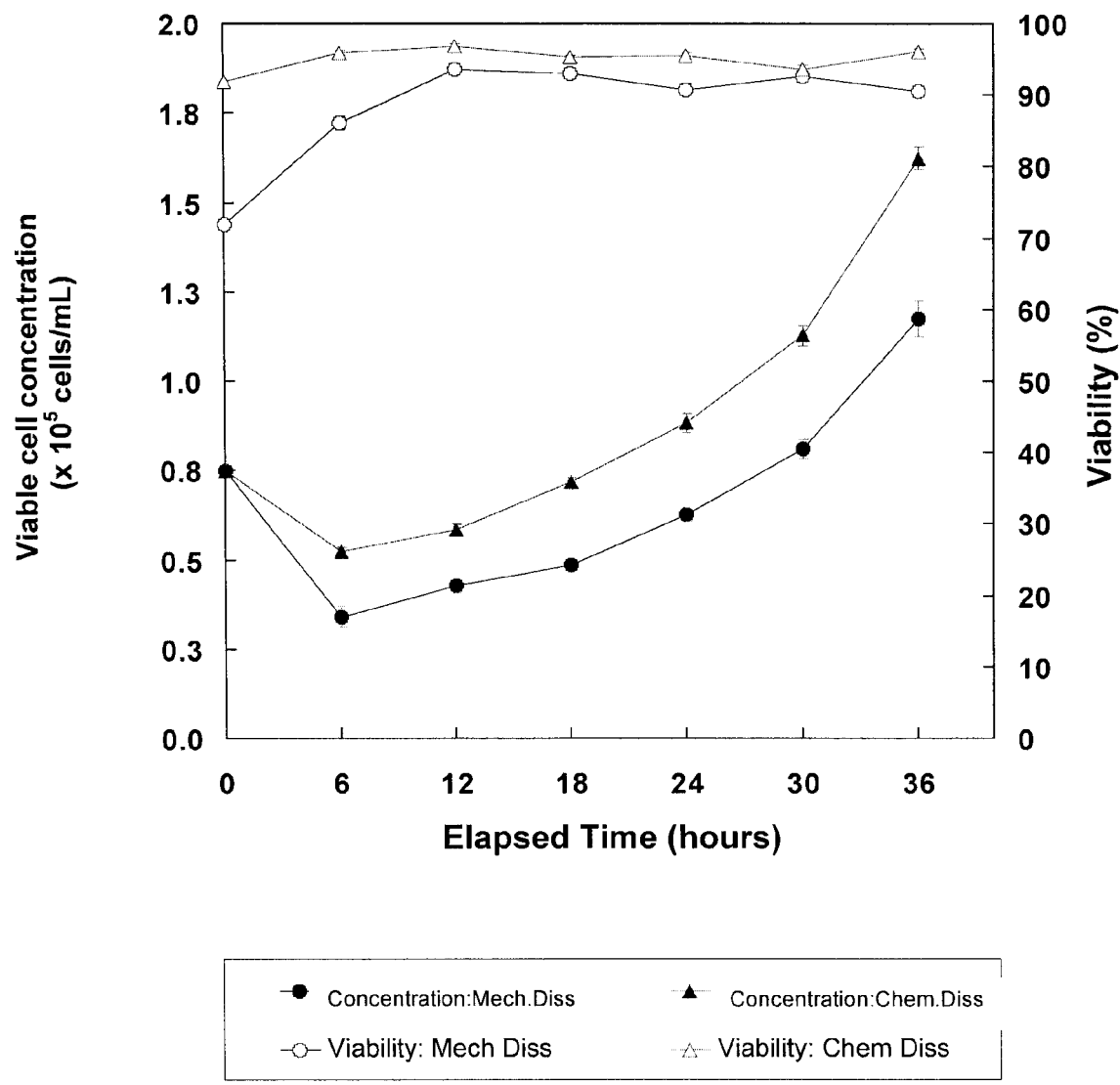
FIG. 11 shows viable cell concentration and viability of mouse neural cells in 125 mL spinner flasks during the first 36 hours following inoculation into 100 mL of PPRF-m4 medium. The spinner flasks were inoculated with either mechanically dissociated (Mech Diss) cells or chemically dissociated (Chem Diss) cells. The spinner flasks were incubated at 37° C. in a humidified atmosphere containing 5% $CO_2$, and the contents were agitated at 100 rpm. The error bars are the standard deviation from the mean (n=3). The cell concentrations and viabilities (36 hours after inoculation) in the cultures seeded with chemically dissociated inocula were significantly higher than those cultures that were seeded with mechanically dissociated inocula (p=0.0181 and p=0.0152 respectively; n=3).

When the dissociation method was held constant, the cultures inoculated with cells that had been chemically dissociated always fared better than those cultures inoculated with cells that had been mechanically dissociated. It is possible that the cells in the inoculum generated by chemical dissociation were less traumatized than their counterparts which underwent mechanical dissociation, and this subsequently resulted in higher cell concentration and viabilities. An experiment was conducted to determine if the method by which the inoculum was generated had an effect on the cell concentration and viability in spinner flasks immediately after seeding. The results of this study are shown in FIG. 11. It is evident that those cultures seeded with chemically dissociated cells fared better in the first 36 hours following inoculation than cultures inoculated with mechanically dissociated cells. At each sampling time, both the measured cell concentration and viability were higher. The viability in those cultures inoculated with mechanically dissociated cells started out low (approximately 70%), but within 12 hours were above 90% indicating that intact dead cells that were contained in the inoculum disintegrated, probably due to the shear present in the spinner flasks. The results demonstrate that chemical dissociation is far superior to mechanical dissociation.

Example 7

Long Term Effects of Chemical Dissociation on Mouse Neurospheres

Cells derived from mouse neurosphere cultures were inoculated into T-flasks containing PPRF-m4 medium, after having been dissociated either mechanically or chemically. The cells were subsequently passaged every 4 days for a total of 10 serial subcultures. During each passage, cells were harvested and the viable cell concentration and viability measured after chemical or mechanical dissociation.

Figure 12:
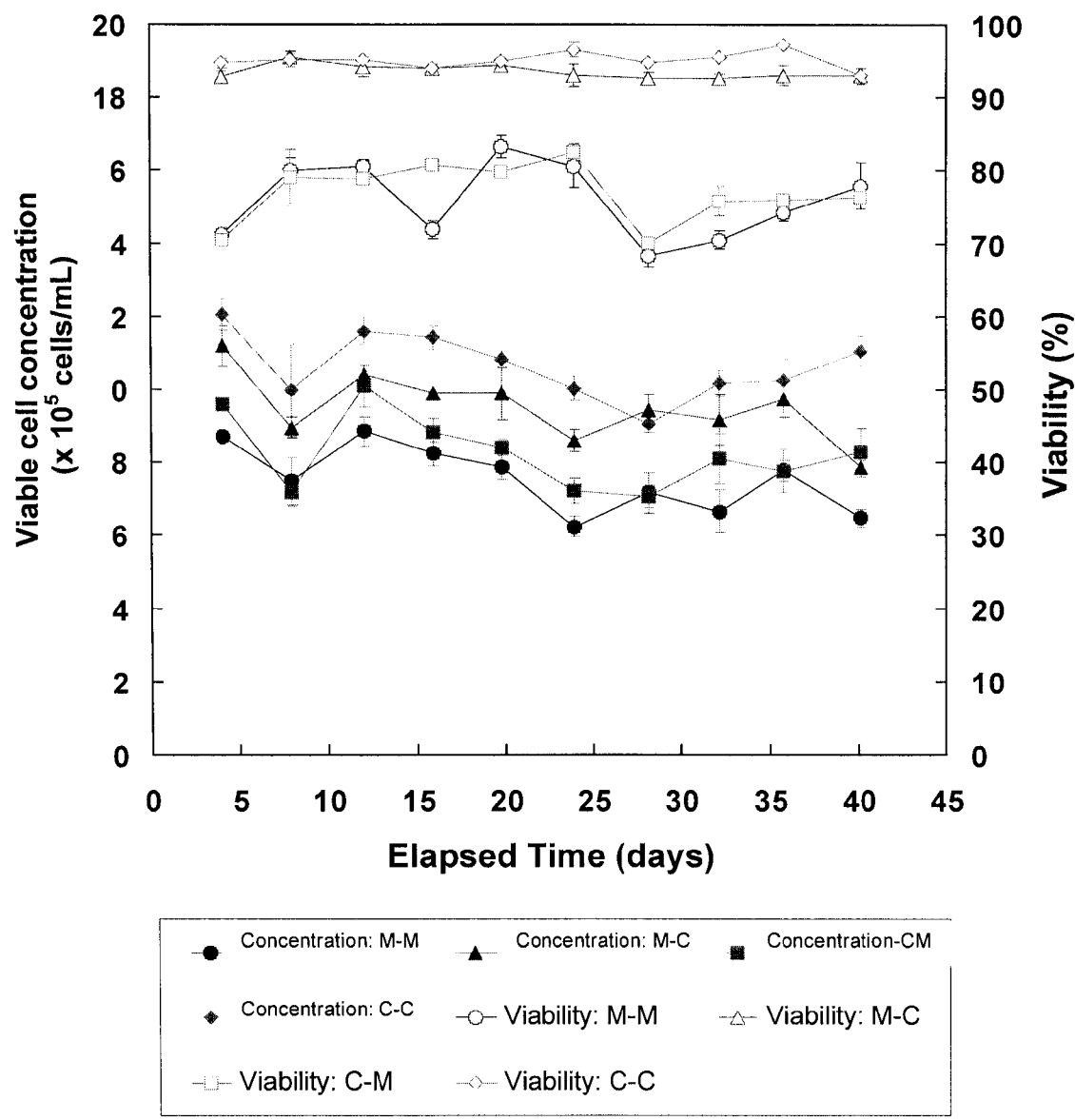
FIG. 12 shows the cell concentration and cell viability of mouse neural cells that were serially subcultured using either chemical or mechanical dissociation. Samples from mouse neurosphere cultures inoculated with mechanically dissociated cells were dissociated either mechanically (M-M) or chemically (M-C). Similarly, samples derived from those cultures that had been inoculated with chemically dissociated cells were dissociated either mechanically (C-M) or chemically (C-C). The cultures were maintained in T-25 flasks containing 5 mL of PPRF-m4 medium. The flasks were incubated at 37° C. in a humidified atmosphere containing 5% $CO_2$, and the cells were passaged every 4 days. The error bars are the standard deviation from the mean (n=3).
Figure 13:
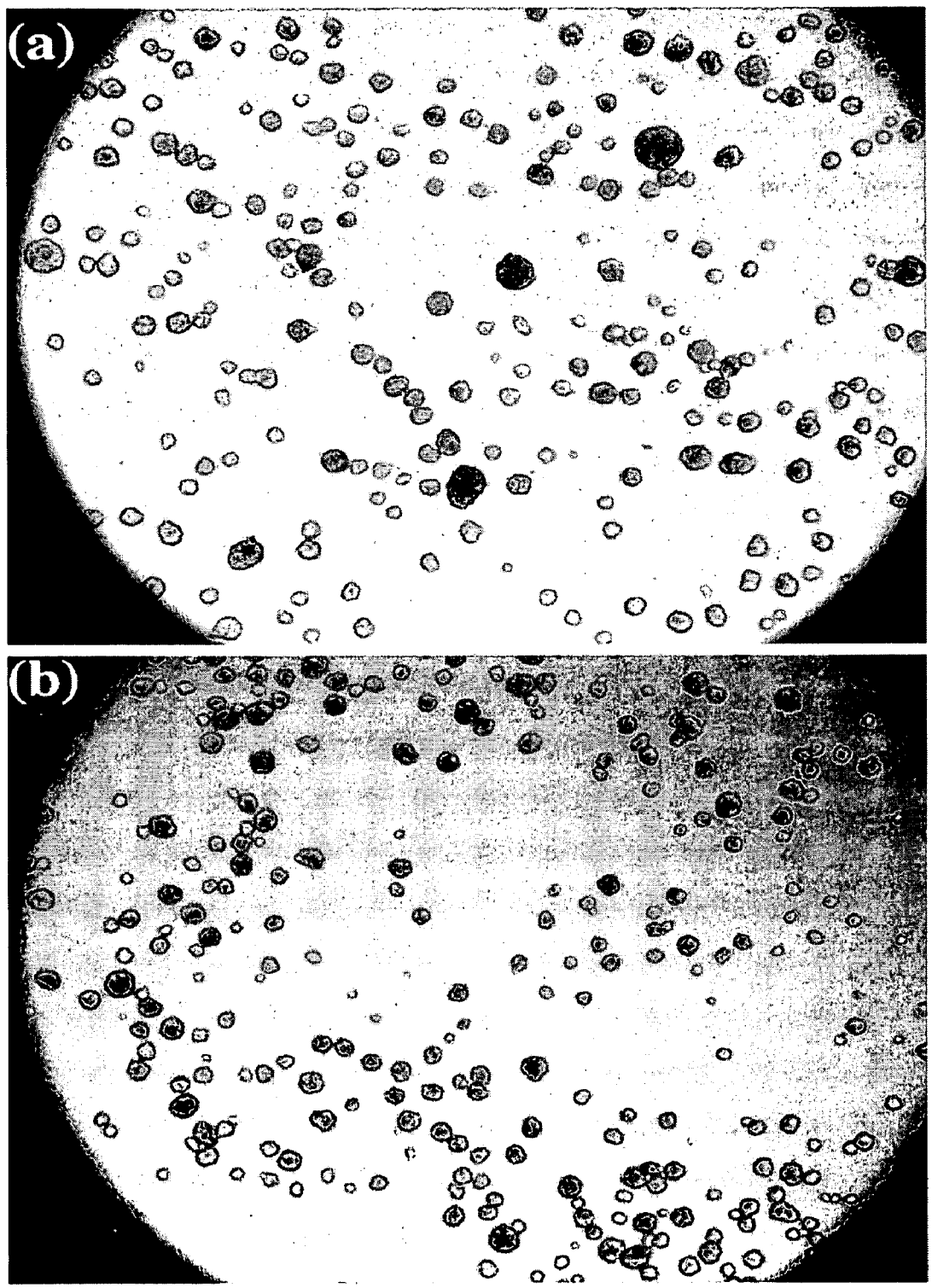
FIG. 13 shows photomicrographs showing neurosphere cultures derived from mouse neural cells after being serially subcultured in PPRF-m4 medium either using (a) Mechanical Dissociation or (b) Chemical Dissociation. The scale bar in (b) represents 400 μm.
Figure 14:
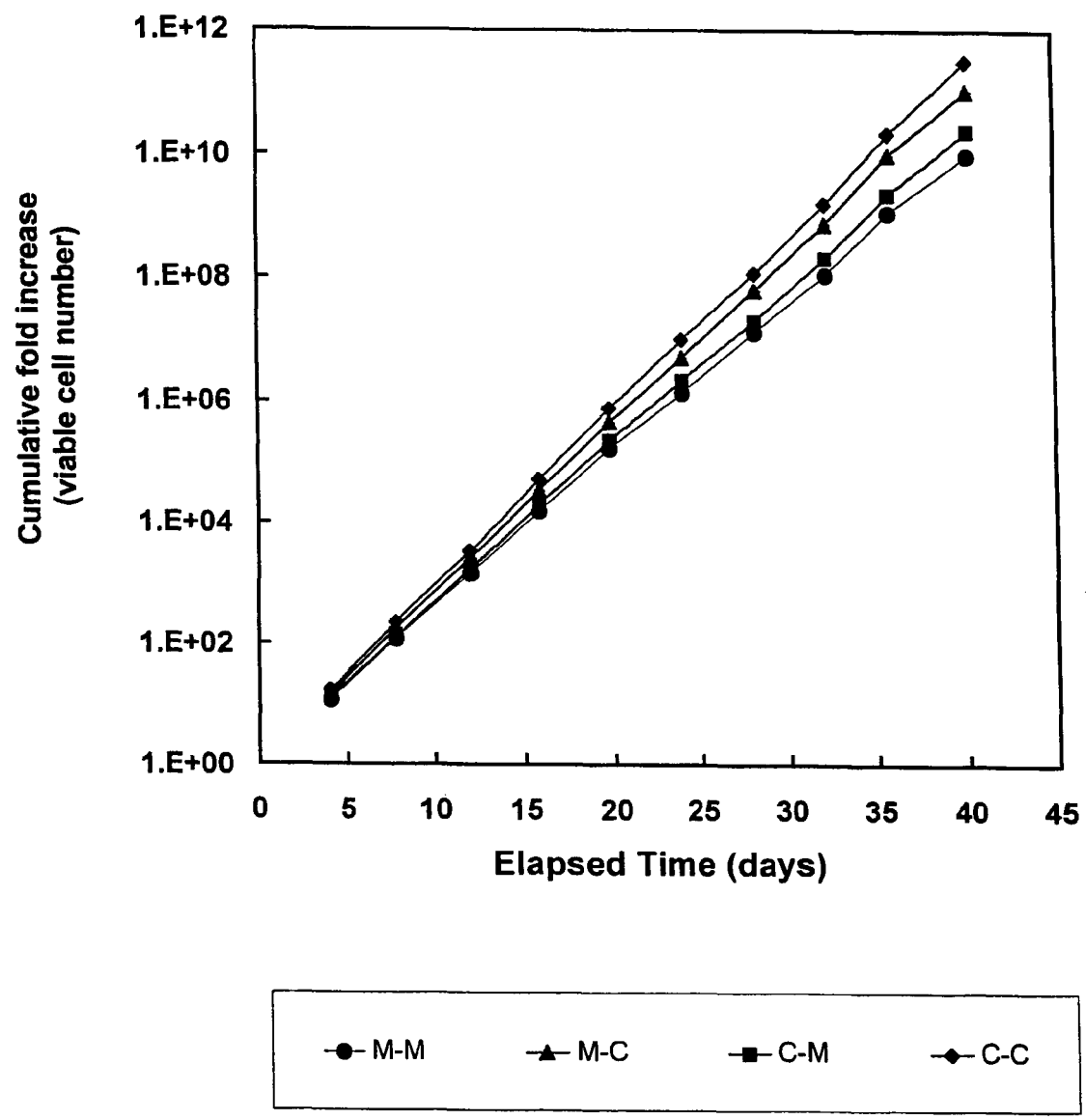
FIG. 14 shows cumulative viable cell number mouse neural cells that were serially subcultured using either chemical or mechanical dissociation. Samples from neurosphere cultures inoculated with mechanically dissociated cells were dissociated either mechanically (M-M) or chemically (M-C). Similarly, samples derived from those cultures that had been inoculated with chemically dissociated cells were dissociated either mechanically (C-M) or chemically (C-C). The cultures were maintained in T-25 flasks containing 5 mL of PPRF-m4 medium. The flasks were incubated at 37° C. in a humidified atmosphere containing 5% $CO_2$, and the cells were passaged every 4 days. The error bars are the standard deviation from the mean (n=3).

The results of the long term study are shown in FIG. 12. It should be noted that the labeling system described above was applied here also. From this graph, it is apparent that although both cell concentration and viability fluctuated with time, cell proliferation was relatively unaffected using chemical dissociation over the course of 10 passages. As expected, the viable cell concentration of a sample was always higher when dissociated chemically rather than mechanically. Overall, the highest viable cell concentration were observed in C-C samples, whereas the lowest were in M-M samples. These same trends were observed with respect to viability. Those samples that were chemically dissociated consistently had viabilities above 90%, whereas those that were mechanically dissociated had viabilities which fluctuated between 67% and 83%. Nutrient analyses revealed that overall glucose and glutamine consumption, as well as the $Y_{lac/gluc}$ and $Y_{amm/gln}$ were unaffected by the choice of dissociation method. FIG. 13 shows photomicrographs of the cells after being serially subcultured. In both cases, NSCs retained the ability to form spherical aggregates, although the aggregates in the chemically dissociated cultures appeared to be slightly more uniform in size. The impact of different dissociation methods on the cumulative multiplication ratio over the course of the experiment is shown in FIG. 14. The M-M cultures had a cumulative cell number of $1.02 \times 10^{10}$ whereas the M-C culture had a cumulative cell number of $1.06 \times 10^{11}$. This shows that choice of dissociation method could lead to a 10-fold difference in the NSC population size over 10 passages. This result was even more pronounced for the cultures inoculated with chemically dissociated cells where the cumulative cell number of C-M and C-C were $2.5 \times 10^{10}$ and $2.8 \times 10^{12}$ respectively, a difference of approximately 2 orders of magnitude in favor of chemical dissociation.

Example 8

Stem Cell Characteristics of Chemically Dissociated Mouse Neurospheres

The capacity of the cells to form spheres, and proliferate in culture for extended periods of time suggest that neural stem cells remained present in the cell population even after being serially subcultured using chemical dissociation. Their presence was further confirmed by performing a clonal study to determine the percentage of cells in culture with the capacity to generate spheres, and by differentiating cells isolated from culture and then immunohistochemically staining them to reveal the presence of the three major neural phenotypes.

Figure 15:
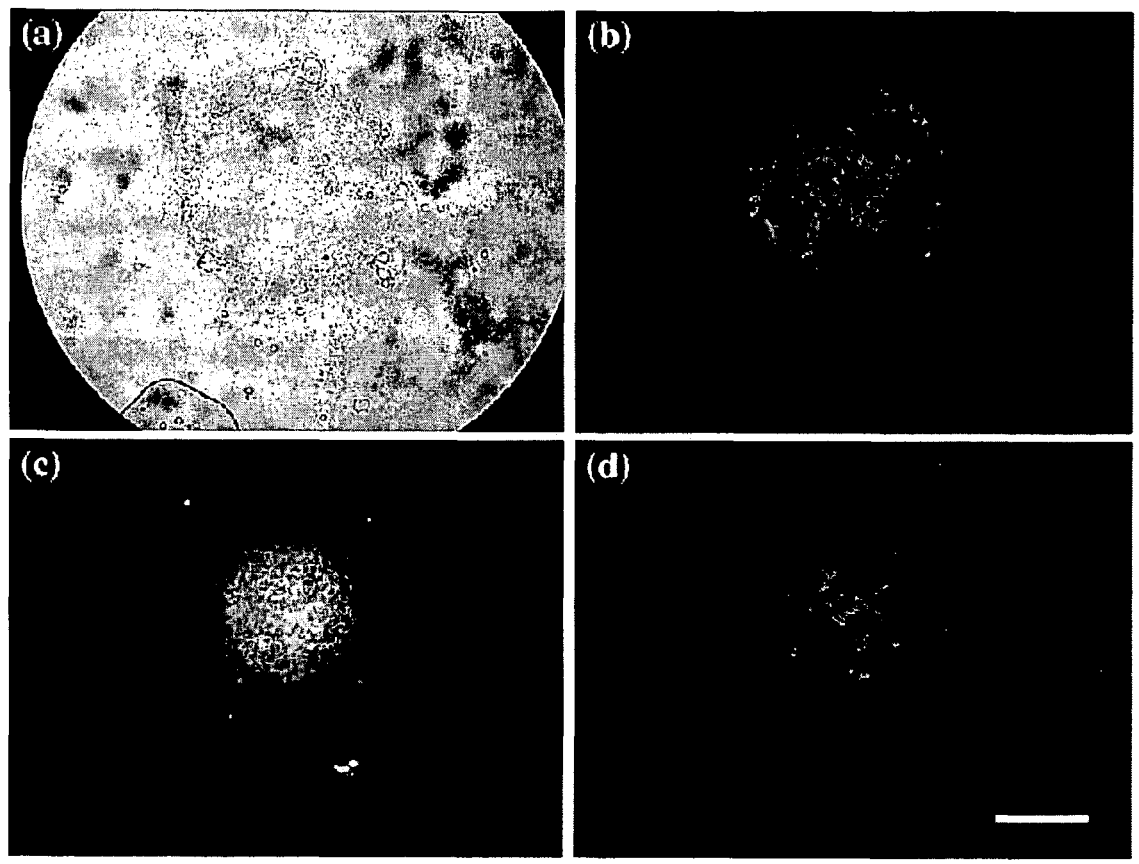
FIG. 15 shows photomicrographs showing that mouse neurospheres that have been serially subcultured using chemical dissociation retain their multipotentiality. Shown is (a) a slide mounted neurosphere aggregate that contained cells which were able to differentiate into (b) neurons, (c) oligodendrocytes, and (d) astrocytes. Scale bar in (d) represents 100 μm.

Clonal analysis revealed that 29.3±3.0% of the cells plated at clonal density retained the capacity to generate spheres after being subcultured using chemical dissociation. This is in line with the previously determined values for passage level 2 cells, but slightly lower than the values reported for passage level 15 cells (Sen, 2003). The average number of secondary spheres that could be generated from a single primary sphere were 75±10 and 84±10 for duplicate experiments. Differentiation and subsequent staining of aggregates isolated from culture after repeated passaging using chemical dissociation revealed that aggregates maintained the ability to generate neurons, astrocytes, and oligodendrocytes. This is shown in FIG. 15.

Example 9

Dissociation of Embryonic Human Neurospheres

Given that human neurospheres have very long doubling times (10-14 days in vitro), a loss of 50% of the cells as a result of mechanical dissociation is significant and extremely undesirable. As such, it was important to develop an alternative to mechanical dissociation for the disaggregation of the human neural stem cell aggregates. Thus chemical dissociation was evaluated for its ability to dissociate embryonic human neurosphere aggregates.

Figure 16:
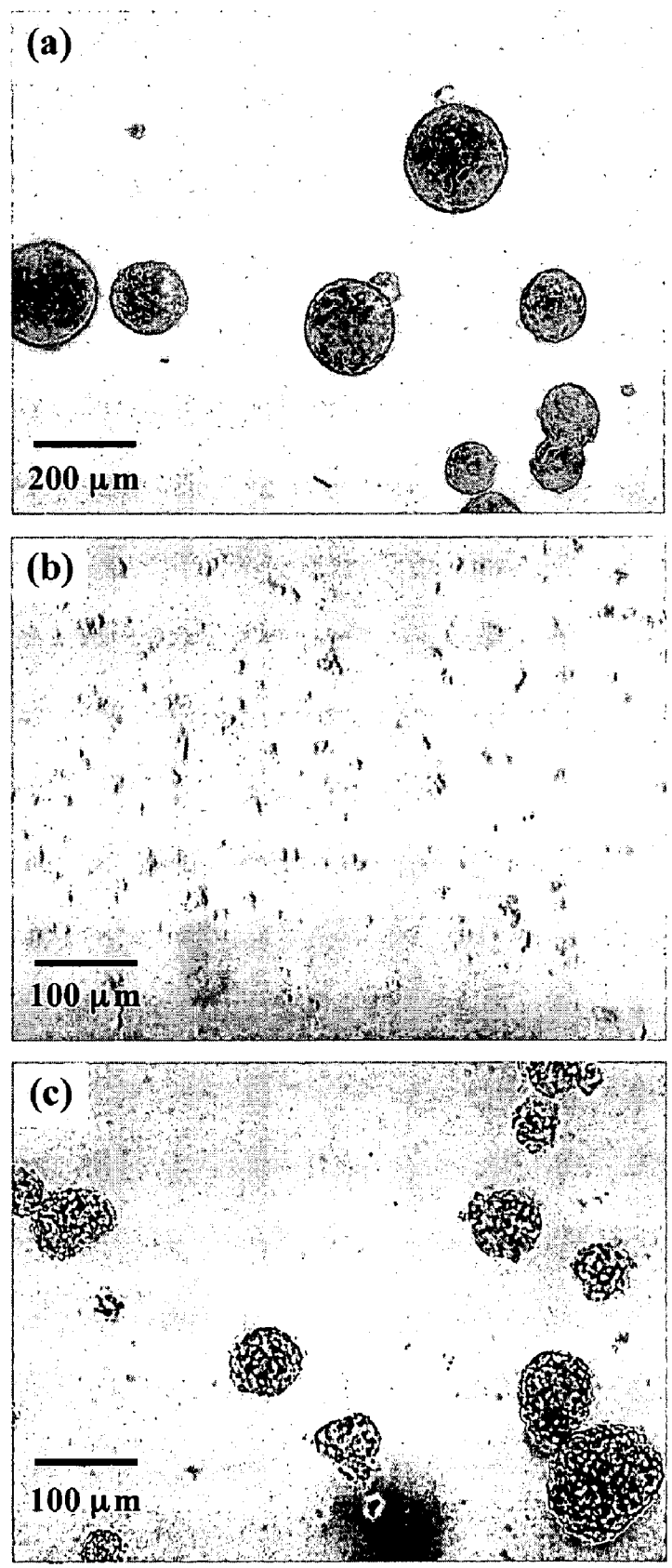
FIG. 16 shows dissociation of embryonic human neural cells. Shown in FIG. (a) are human neural cell aggregates prior to dissociation. The aggregates are comprised of cells held together in an extracellular matrix. FIG. (b) shows human neural cells following chemical dissociation. It is apparent that the cells dissociated into a single cell suspension. These cells were subsequently inoculated at 100,000 cells/mL into 25 cm² tissue culture flasks containing 5 mL of PPRF-m4 medium. The post-dissociation cultures are shown 5 days after inoculation in FIG. (c). It is evident that cells that were inoculated following chemical dissociation retain the ability to proliferate and form new aggregates.

Passage 13 embryonic neural cells originally procured from the cortex of an 8-14 week old human post-mortem fetus were subjected to chemical dissociation to determine if modifying the environmental pH for a limited period of time, together with gentle periodic pipetting could achieve dissociation while increasing the viability. The procedure described earlier in Example 4 for embryonic mouse neurospheres was slightly modified for the human neurosphere aggregates, and the modified procedure is described here. Human neurosphere aggregates were placed in a sterile 15 mL centrifuge tube and centrifuged for 10 minutes at 1000 rpm (140 g). Once the supernatant had been removed, the aggregates were gently resuspended in 200 µL of supernatant. An equal volume of a chemical dissociation solution with a pH of 12 (produced by adding 150 µL of 1.0 N NaOH to 2 mL of PPRF-m4 medium) was added to the aggregates resulting in a final pH of 11.3. The aggregates were gently pipetted 10 times at each of 0, 2, 4 and 6 minutes following the addition of the chemical dissociation solution. After 8 minutes the dissociation was stopped by adding an acidic medium with a pH of 1.2 (produced by adding 150 µL of 1.0 N HCl to 2 mL of PPRF-m4 medium) and pipetting the suspension gently 10 more times. As shown in FIG. 16, this resulted in a uniform single cell suspension. Measurements revealed that the cell viability following chemical dissociation was approximately 80%. This was significantly higher than the viability of 55% achieved following mechanical dissociation in the control culture. Moreover, subsequent culturing of the cells in 25 cm$^2$ tissue culture flasks containing 5 mL of PPRF-m4 medium revealed that they retained a healthy morphology, and had the capacity to divide and form new aggregates. These results suggest that chemical dissociation can be used to generate a single cell suspension from embryonic neural cell aggregates without adversely affecting the cells. The higher viabilities obtained, the lack of harm to the cell population, the decrease in the manual intensity, and the reproducibility of the procedure all suggest that chemical dissociation is superior to mechanical dissociation, the accepted current state-of-the-art for this application.

Example 10

Dissociation of Neonatal Porcine Pancreatic Cell Aggregates

Figure 17:
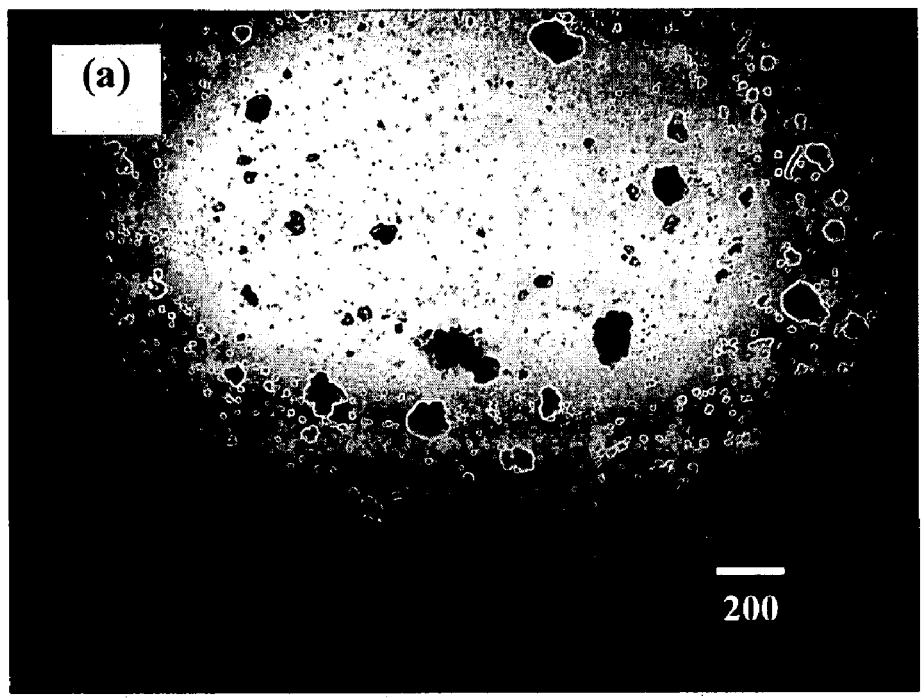
FIG. 17 shows chemical dissociation of neonatal porcine pancreatic cell aggregates derived from primary pancreatic tissue. Aggregates of porcine pancreatic tissue containing pancreatic stem cells were evaluated for their susceptibility to chemical dissociation. FIG. (a) shows the aggregated primary tissue prior to chemical dissociation. Following isolation in a centrifuge tube, a chemical dissociation solution was added to the sample, and the sample was gently gently pipetted 10 times every minute for seven minutes using a 1.0 mL pipette. FIG. (b) shows that after 7 minutes, the aggregates had dissociated to form a single cell suspension
Figure 17:
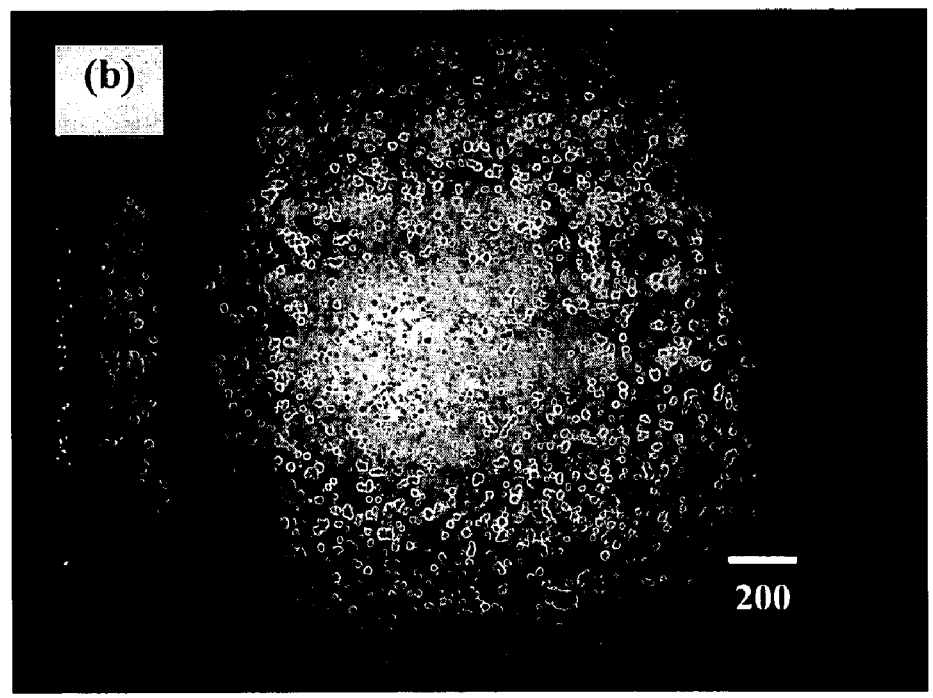

The primary tissue fraction believed to contain the pancreatic stem cells was isolated from a viable, functional porcine pancreas, placed in serum free medium for 24 hours, and then subjected to chemical dissociation. The procedure described earlier for embryonic murine neural stem cells was slightly modified for the porcine pancreatic stem cell aggregates, and the modified procedure is described here. Porcine pancreatic stem cell aggregates were placed in a sterile 15 mL centrifuge tube and centrifuged for 10 minutes at 1000 rpm (140 g). Once the supernatant had been removed, the aggregates were gently resuspended in 3 mL of PPRF-m4 medium. An equal volume of a chemical dissociation solution with a pH of 12.3 (produced by adding 300 µL of 1.0 N NaOH to 4 mL of PPRF-m4 medium) was added to the aggregates resulting in a final pH of 11.1. The aggregates were gently pipetted 10 times every minute for 7 minutes following the addition of the chemical dissociation solution. The dissociation was stopped by adding 3 mL of an acidic medium with a pH of 1.3 (produced by adding 300 µL of 1.0 N HCl to 4 mL of PPRF-m4 medium) and pipetting the suspension gently 10 more times. As shown in FIG. 17, this resulted in a uniform single cell suspension.

The average viability of the single cells obtained using chemical dissociation was approximately 73%. Several trials aimed at producing a single cell suspension through mechanical dissociation failed. Thus, it is not possible to compare the viability between mechanically and chemically dissociated cells. Whereas the viability of 73% may appear to be low relative to that for the dissociated embryonic murine neural stem cells, it should be reiterated that the tissue was primary tissue in which cell death could have occurred during isolation, or the subsequent 24 hours during which the aggregates remained in the cell culture medium prior to being dissociated. Moreover, this study demonstrates for the first time that it is possible to generate a single cell suspension from primary pancreatic tissue, and that this can be accomplished using chemical dissociation, and not mechanical dissociation.

Example 11

Dissociation of Cultured Mouse Mammary Epithelial Cell Aggregates

Figure 18:
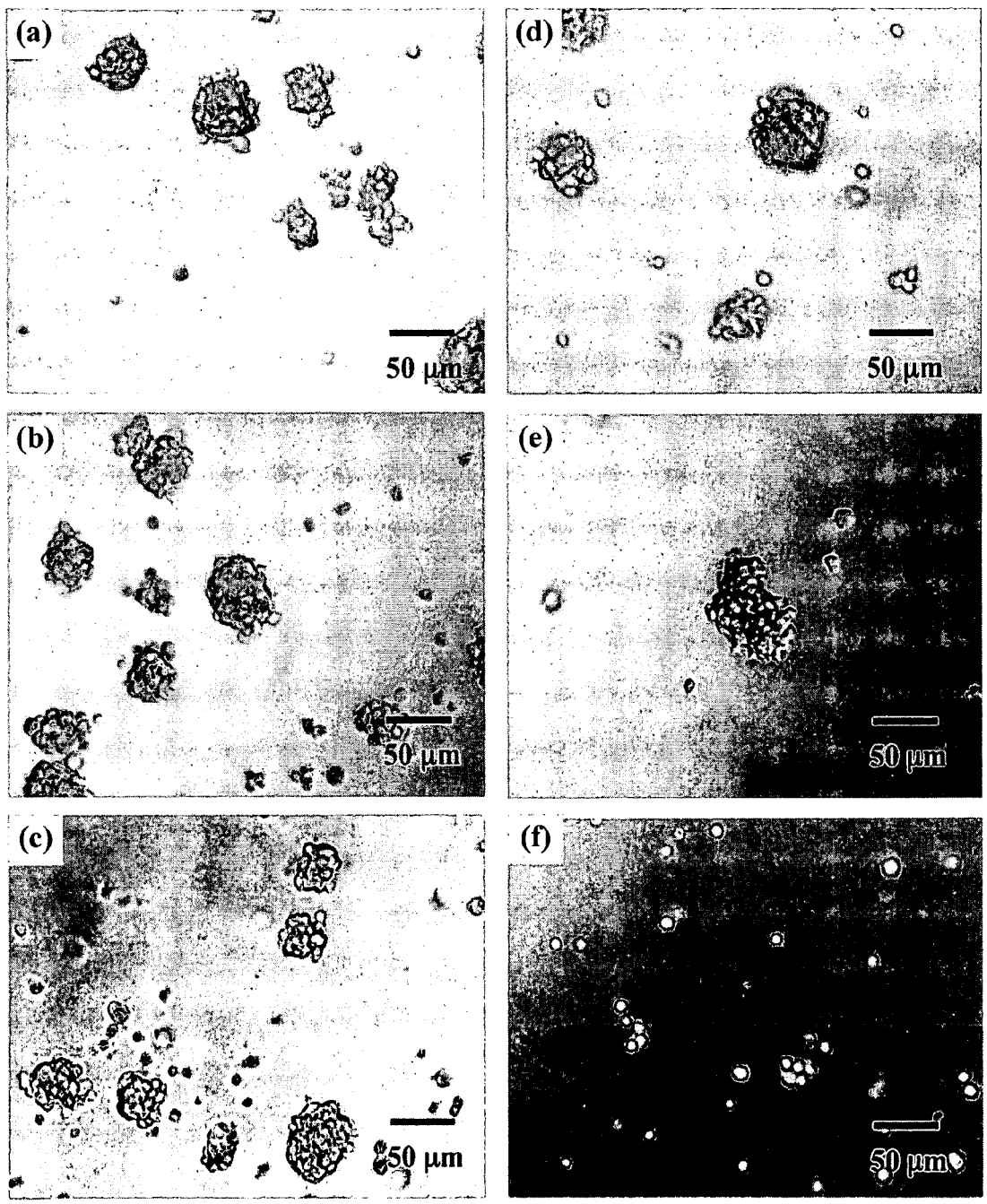
FIG. 18 shows chemical dissociation of mouse mammary cell aggregates (mammospheres). Mammary cells were isolated in 96 well plates after being cultured in 25 cm² tissue culture flasks containing PPRF-m4 medium for 7 days. Phosphate buffered saline was added to the control wells whereas chemical dissociation solution was added to the test wells. The contents of the wells were then gently pipetted 10 times every two minutes using a 200 μL pipette. FIG. (a) shows the mammospheres in a control well prior to any treatment. FIG. (b) shows a control well after 2 minutes and FIG. (c) shows a control well after 11 minutes. FIG. (d) shows a test well prior to the addition of chemical dissociation solution. FIG. (e) shows a test well after 2 minutes and FIG. (f) shows a test well after 11 minutes. It is evident that the mammospheres subjected to chemical treatment responded by dissociating into a single cell suspension.

Passage level 6 mammary epithelial cells derived from 5-7 week old mice were cultured in a serum-free medium in 25 cm$^2$ Nunc tissue culture flasks resulting in the formation of mammospheres. The chemical dissociation procedure described earlier in Example 3 for embryonic mouse neurospheres was slightly modified for the mouse mammary epithelial cell aggregates, and the modified procedure is described here. Mammospheres were isolated from the tissue culture flasks and placed in 96 well plates. Each well contained 100 µL of PPRF-m4 medium. 100 µL of chemical dissociation solution was added to each well, and the contents of each well were gently pipetted 10 times every 2 minutes for a total of 10 minutes. The progression of the dissociation in both the control wells and the chemical dissociation wells is shown in FIG. 18. After two minutes, the tightly bound aggregates remained in the control cultures, whereas the aggregates in the test cultures started to change their morphology such that there appeared to be less extracellular matrix, and individual cells within the aggregates were more visible. After 11 minutes, aggregates remained in the control culture (despite the 10 gentle pipetting every two minutes) whereas the aggregates in the chemical dissociation wells had dissociated into a single cell suspension. Subsequent culture of the single cells generated using chemical dissociation revealed that they remained both healthy and viable.

Example 12

Detachment of Chinese Hamster Ovary (CHO) Cells from a Surface

Figure 19:
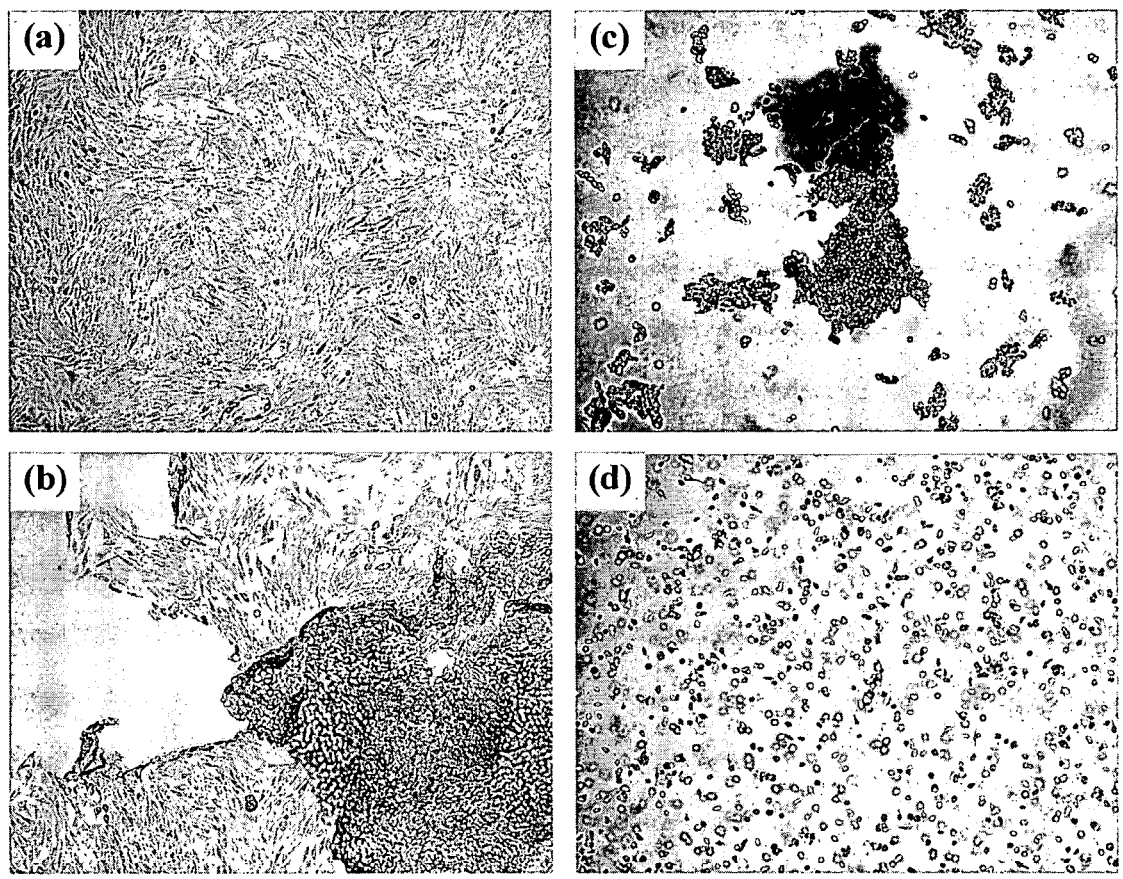
FIG. 19 shows chemical dissociation of CHO Cells. FIG. (a) shows a typical confluent monolayer culture prior to treatment. CHO cells treated chemically are shown (b) 5 minutes, (c) 20 minutes, and (d) 25 minutes after the start of the dissociation procedure. The tissue culture flasks containing the cells were rocked periodically. FIGS. (c) and (d) are shown after mild pipetting with a 1.0 mL pipette.
Figure 20:
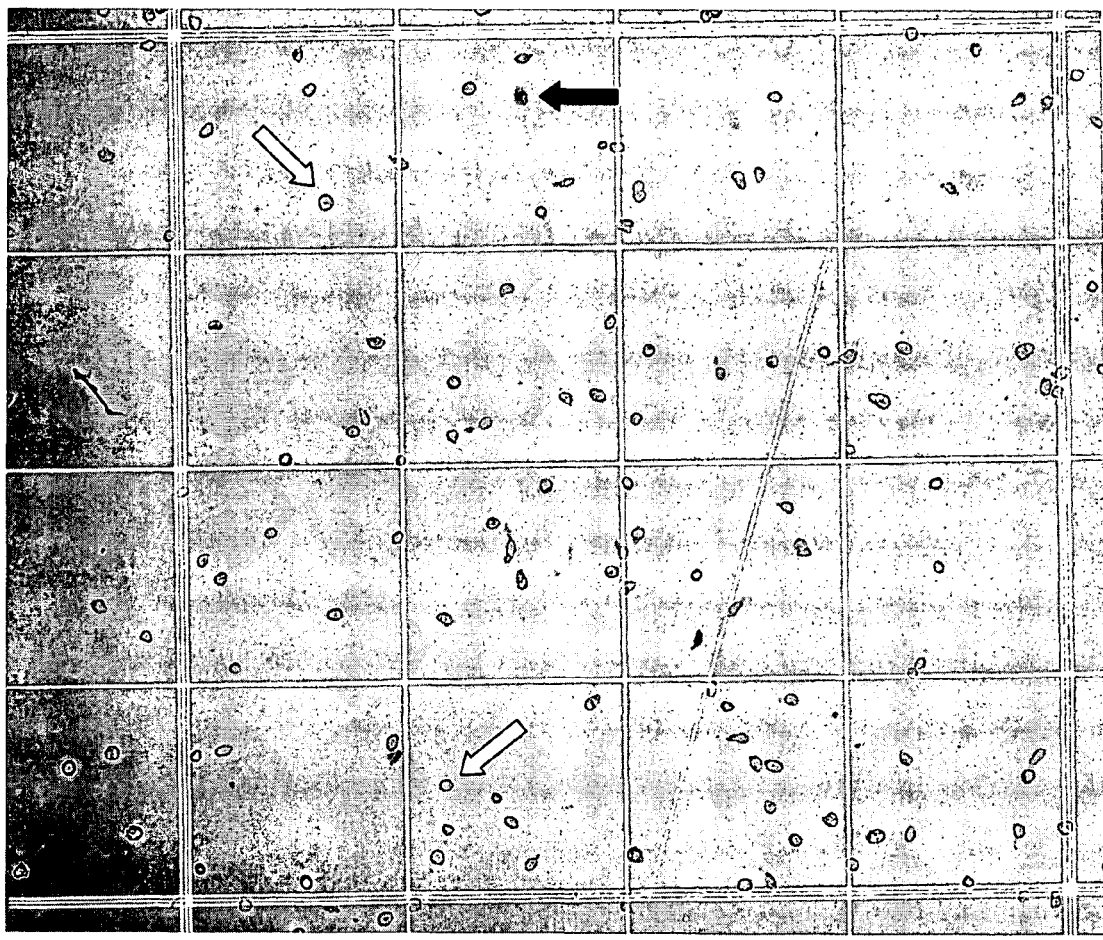
FIG. 20 shows that following chemical dissociation, the suspension of single CHO cells described in FIG. 19 was stained with 0.1% trypan blue in PBS, placed on a hemacytometer, and viewed under a microscope to determine if the cells remained viable. Typical viable cells are shown with the white arrow whereas dead cells are identified with a black arrow. It is evident that almost all of the cells on the hemacytometer are viable.
Figure 21:
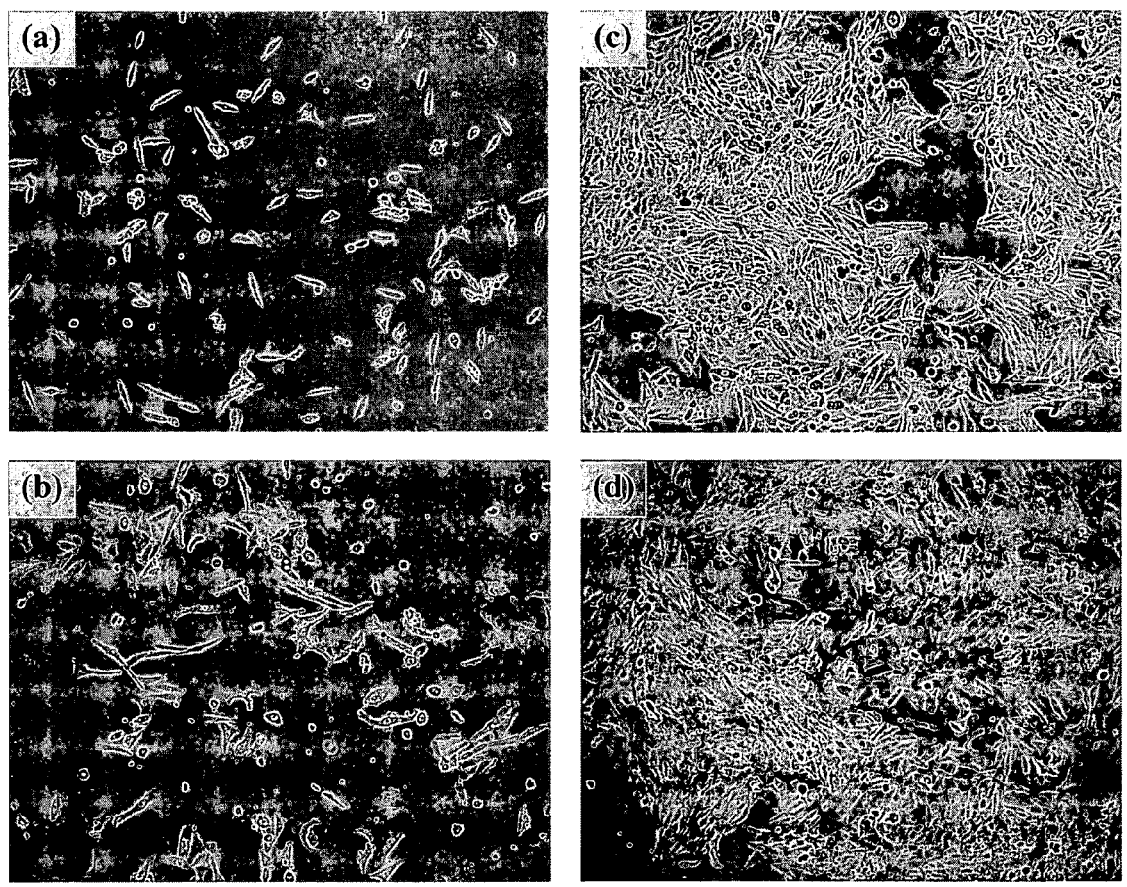
FIG. 21. CHO cells were chemically detached and dissociated and then inoculated at a density of 15,000 cells/cm² into 25 cm² tissue culture flasks containing 5 mL of fresh medium (DMEM with 10% FBS) to determine if they retained the ability to attach to a surface and divide. The cells following chemical dissociation are shown (a) 3 days, (b) 7 days, (c) 9.5 days and (d) 11 days after inoculation into fresh medium. It is very evident following chemical dissociation, the cells retained the ability to attach and proliferate to confluence.

The invention was evaluated for its ability to detach CHO cells from a monolayer culture. CHO cells were inoculated at 15,000 cells/cm$^2$ into 25 cm$^2$ Nunc tissue culture flasks containing DMEM and fetal bovine serum (FBS) and allowed to mitotically divide until a confluent monolayer was attained. The spent medium was removed, and the cells were gently rinsed twice (2.0 mL per rinse) with PBS. A volume of 2 mL (per flask) of chemical dissociation solution (described above) was added to the cells. The flasks were intermittently rocked. The progression of the experiment can be seen in FIG. 19. In the test cultures, the attached cells began to detach as a sheet within 5 minutes of the start of the procedure. After 20 minutes, the cells were all in suspension as small clumps, and by 25 minutes, these clumps could be easily dissociated into single cells using mild pipetting with a 1 mL pipette. Trypan blue staining revealed that the cell population had a very high viability (see FIG. 20). The single cells were isolated following centrifugation and subsequently inoculated at 15,000 cells/cm$^2$ into 25 cm$^2$ Nunc tissue culture flasks containing DMEM with 10% FBS (total inoculum was 375,000 cells per tissue culture flask). The cells appeared healthy, retained the ability to attach to a substrate, and were able to mitotically divide and regenerate a confluent monolayer (see FIG. 21). The average total number of cells measured at confluence was over 2×10$^6$ cells per tissue culture flask, indicating that the inoculated cells had undergone more than two doublings. This demonstrates that altering the environmental pH (the chemical dissociation approach) is a viable alternative to enzymatic methods that are currently employed to detach and dissociate anchorage dependent cells and generate a single cell suspension.

Example 13

Detachment of L-929 Murine Fibroblast Cells from a Surface

Figure 22:
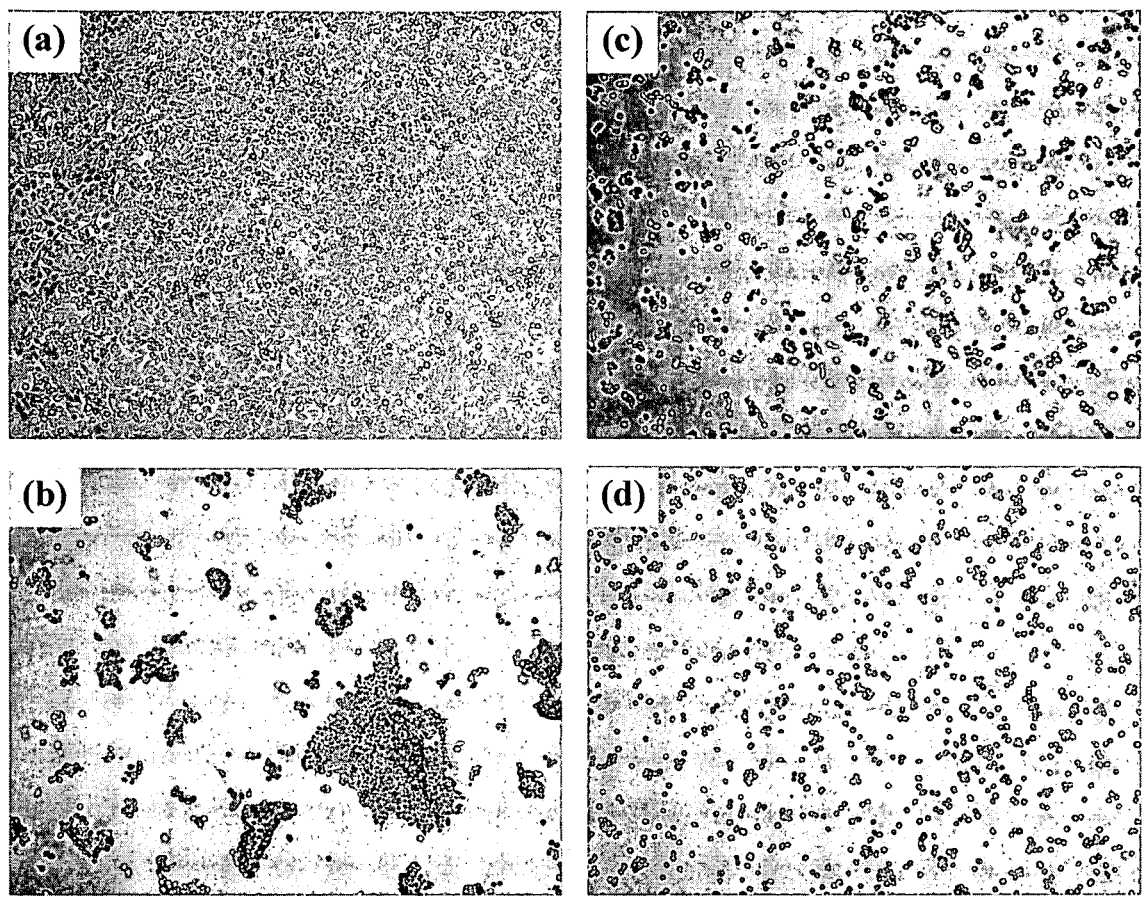
FIG. 22 shows chemical dissociation of L-929 murine lung fibroblast cells. FIG. (a) shows a typical confluent monolayer culture prior to treatment. L-929 cells that were subjected to chemical dissociation solution are shown (b) 2 minutes (c) 4 minutes and (d) 25 minutes after the start of the dissociation procedure. The tissue culture flasks containing the cells were rocked periodically. FIGS. (c) and (d) are shown after mild pipetting with a 2.0 mL pipette.
Figure 23:
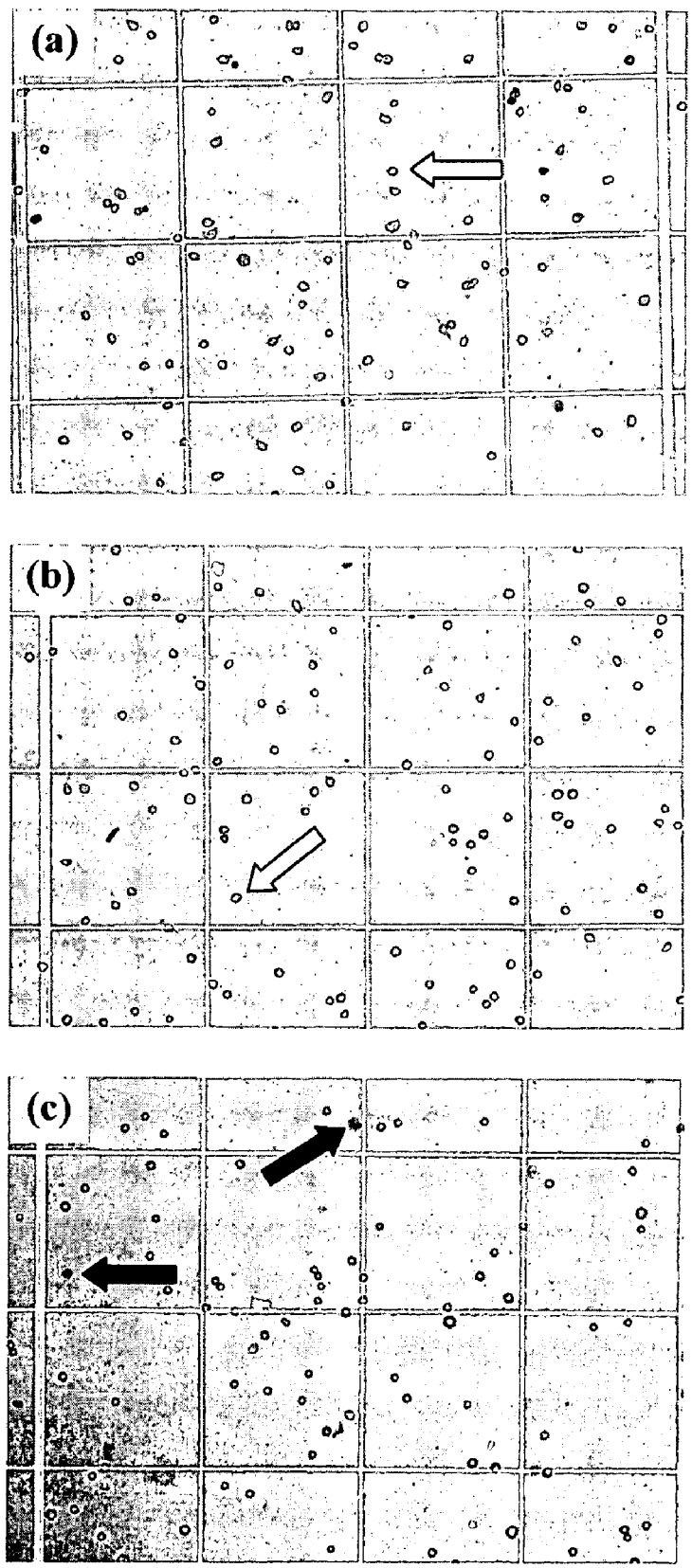
FIG. 23 shows that following chemical dissociation, the single cell suspension of L-929 cells described in FIG. 22(*d*) was stained with 0.1% trypan blue in PBS, placed on a hemacytometer, and viewed under a microscope to determine if the cells remained viable. Shown are cells which remained in the chemical dissociation solution for (a) 15 minutes (b) 35 minutes and (c) 6.5 hours. Typical viable cells are shown with the white arrow whereas typical dead cells are identified with a black arrow. It is evident that the cell population retained a high rate of viability even after remaining in the chemical dissociation solution for 6.5 hours.
Figure 24:
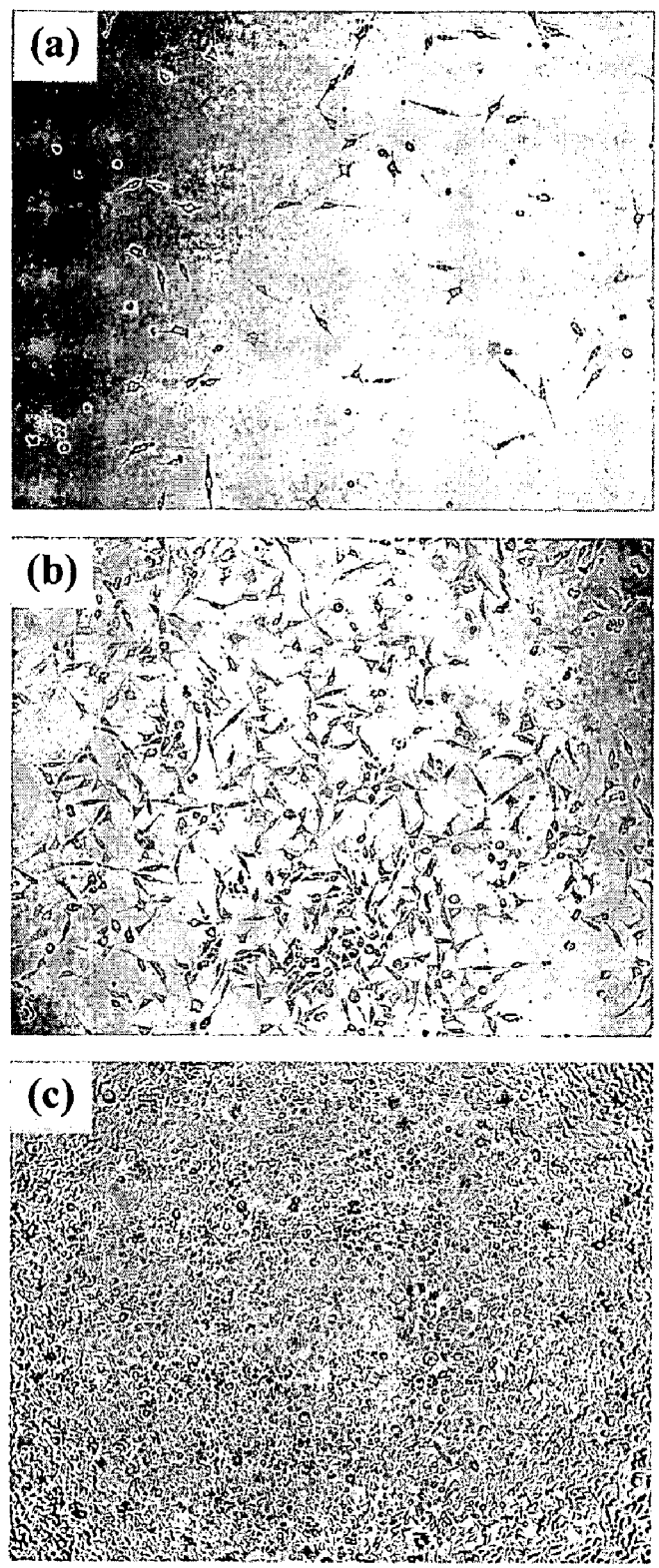
FIG. 24. L-929 cells were detached and dissociated chemically and then inoculated at a density of 15,000 cells/cm$^2$ into 25 cm$^2$ Nunc tissue culture flasks containing 5 mL of fresh medium (DMEM with 10% FBS) to determine if they retained the ability to attach to a surface and divide. The cells which had undergone chemical dissociation are shown after (a) 3 days (b) 7 days and (c) 9.5 days after inoculation into fresh medium. It is very evident that subsequent to chemical dissociation, the cells retained the ability to attach and proliferate until confluence was reached.

It was decided to investigate if the chemical dissociation method was effective for anchorage dependent cell types other than CHO cells. Thus, chemical dissociation was evaluated for its ability to detach L-929 murine lung fibroblast cells from a monolayer culture. L-929 cells were inoculated at 5000 cells/cm$^2$ into 25 cm$^2$ Nunc tissue culture flasks containing DMEM and fetal bovine serum (FBS) and allowed to divide until a confluent monolayer was reached. The spent medium was removed, and the cells were gently rinsed twice (2.0 mL per rinse) with PBS. A volume of 2 mL (per flask) of chemical dissociation solution (described above) was added to the cells. The flasks were intermittently rocked. The progression of the experiment can be seen in FIG. 22. The cells started to detach from the surface in clumps within 2 minutes of the start of the procedure. After 4 minutes it was found that gentle pipetting with a 2 mL pipette resulted into a mixture of single cells and clumps containing 2-8 cells, and eventually this procedure led to the formation of a single cell suspension. Trypan blue staining revealed that the cell population had a very high viability (see FIG. 23), and remarkably retained a very high viability after being exposed to the chemical dissociation solution for 6.5 hours. The single cells were isolated following centrifugation and subsequently inoculated at 5000 cells/cm$^2$ into 25 cm$^2$ Nunc tissue culture flasks containing DMEM with 10% FBS (total inoculum was 375,000 cells per tissue culture flask). The cells appeared healthy, retained the ability to attach to a substrate, and were able to mitotically divide and regenerate a confluent monolayer (see FIG. 24). The average total number of cells obtained at confluence was over 6×10$^6$ cells, indicating that the inoculated cells had undergone more than five doublings. This demonstrates that altering the environmental pH (chemical dissociation) is a viable alternative to mechanical and enzymatic methods that are currently employed to detach anchorage dependent cells and generate a single cell suspension.

Example 14

Detachment of Murine Embryonic Stem Cells (ES)

Figure 25:
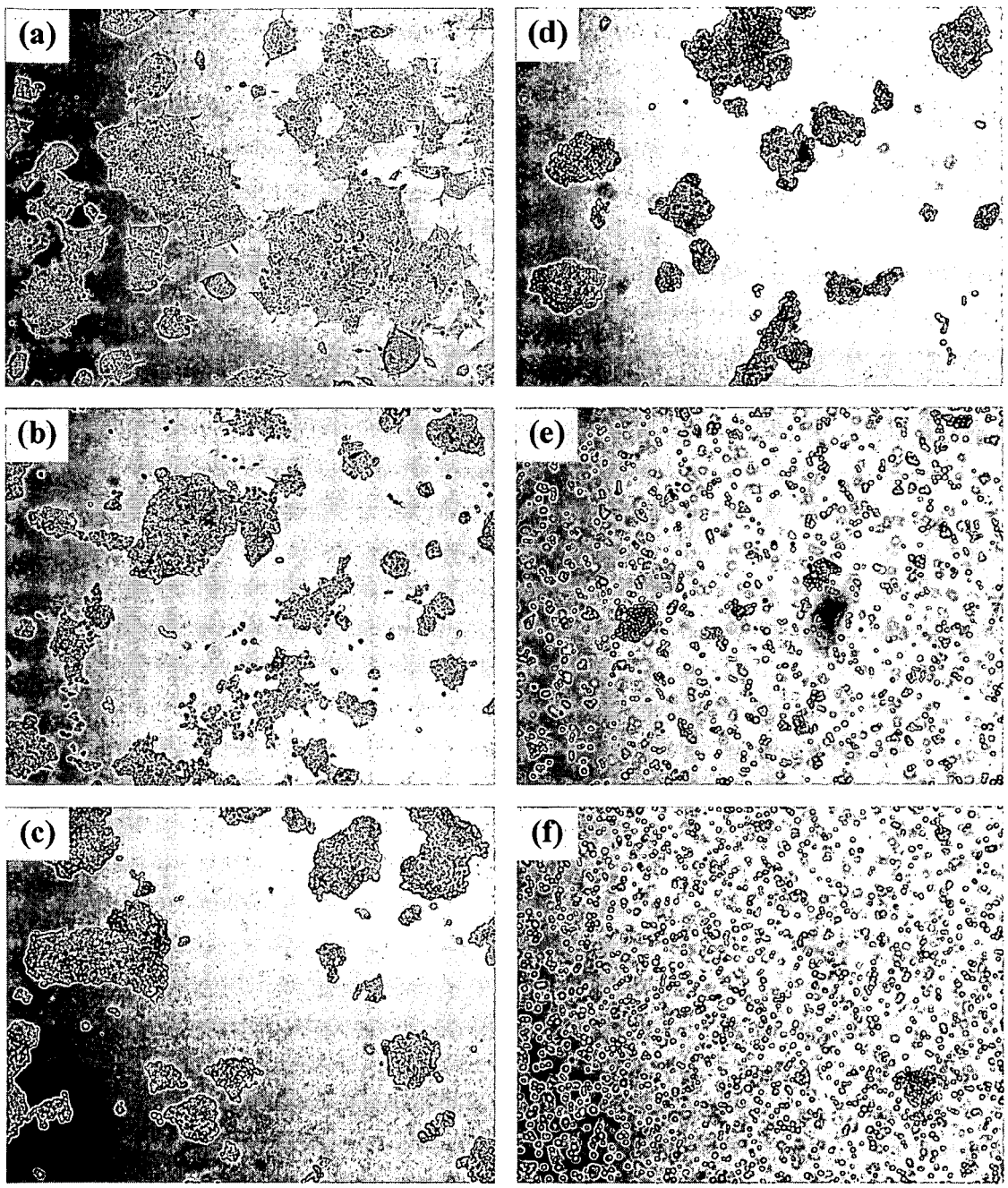
FIG. 25 shows mouse embryonic stem (ES) cells subjected to chemical dissociation. FIG. (a) shows the cells prior to dissociation. The cells are shown at (b) 2 minutes and (c) 5 minutes, (d) 10 minutes (e) 19 minutes and (f) 22 minutes after the initiation of the dissociation protocol. In each case, the tissue culture flasks were rocked periodically. The cells in FIGS. (e) and (f) were gently gently pipetted 10 times with a 1.0 mL pipette prior to being photographed.
Figure 26:
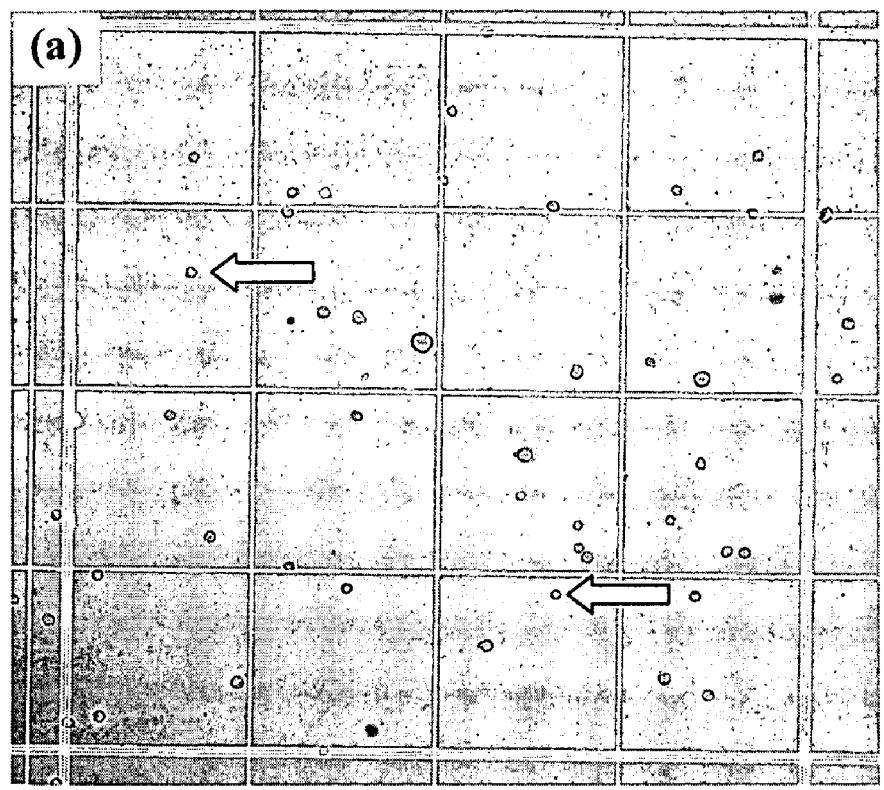
FIG. 26. Following chemical dissociation, the suspension of mouse embryonic stem cells described in FIG. 25(*f*) were stained with 0.1% trypan blue in PBS, placed on a hemacytometer, and viewed under a microscope to determine if the cells remained viable. Shown are cells which remained in the chemical dissociation solution for (a) 32 minutes and (b) 6.5 hours. Typical viable cells are shown with a white arrow whereas typical dead cells are identified with a black arrow. It is evident that the cell population retained a relatively high viability even after remaining in the chemical dissociation solution for 10 hours.
Figure 26:
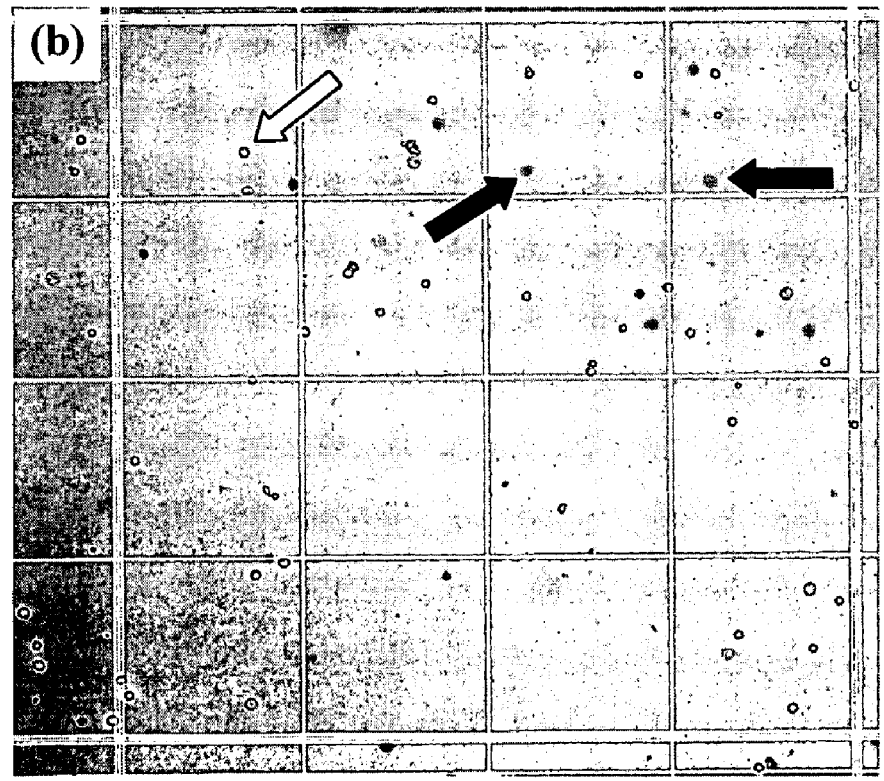
Figure 27:
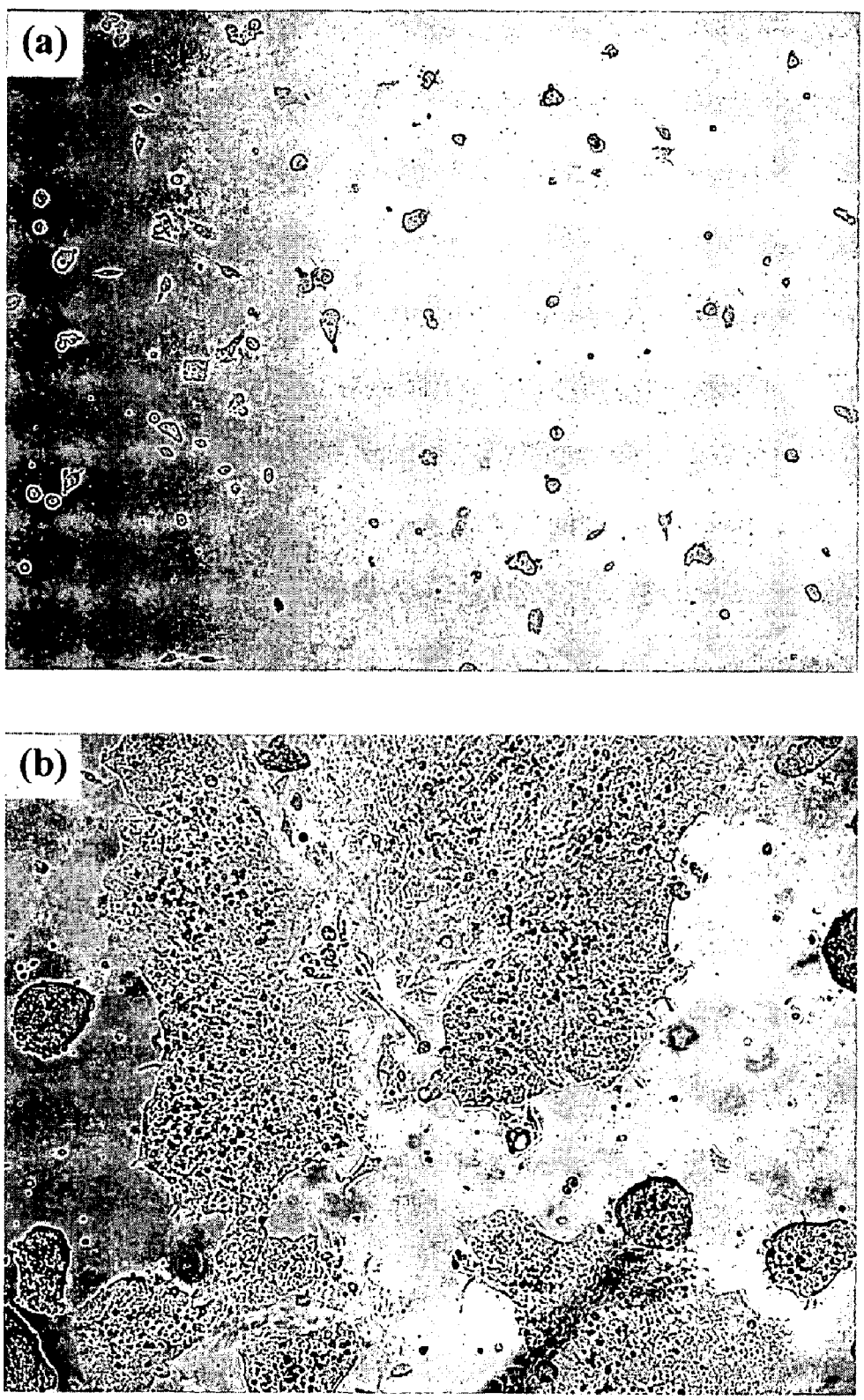
FIG. 27 Mouse embryonic stem cells were chemically detached and dissociated and then inoculated at a density of 10,000 cells/cm$^2$ into 25 cm$^2$ Nunc tissue culture flasks containing 5 mL of a DMEM based medium with 10% FBS to determine if they retained the ability to attach to a surface and divide. The chemically dissociated cells are shown (a) 1 day and (b) 5 days after inoculation into fresh medium. It is very evident following chemical dissociation, the cells retained the ability to attach and proliferate.
Figure 28:
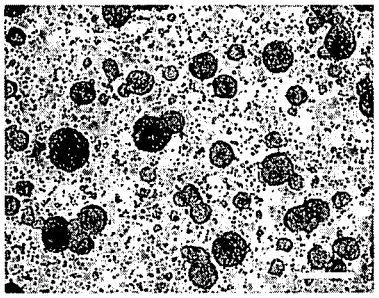
FIG. 28. Photomicrographs showing the effect of serially subculturing (4 passages) cells from mouse neuropsheres dissociated with a sodium hydroxide based dissociation solution. At each passage, photomicrographs show the cells prior to dissociation and immediately after dissociation. The cells were passaged in 25 cm$^2$ tissue culture flasks containing 5 mL of PPRF-m4 medium. The flasks were incubated in a humidified 37° C. environment containing 5% $CO_2$. Scale bars=100 μm.
Figure 28:
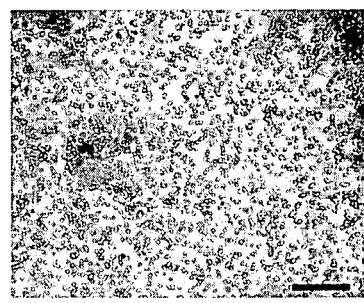
Figure 28:
Figure 28:
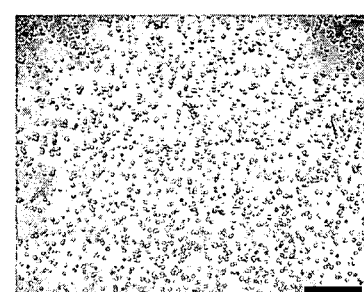
Figure 28:
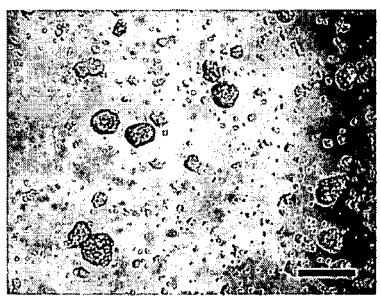
Figure 28:
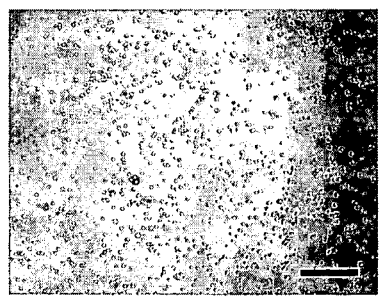
Figure 28:
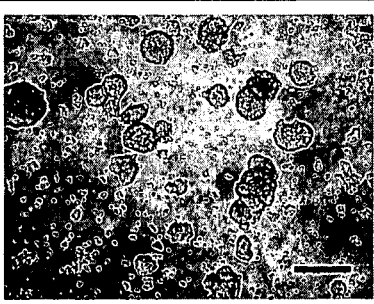
Figure 28:
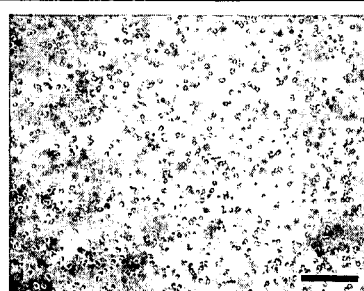

Chemical dissociation was evaluated for its ability to detach murine embryonic stem cells from the inner bottom surface of a tissue culture flask. The cells were inoculated into 25 cm$^2$ tissue culture flasks at an appropriate density and allowed to attach and divide for 48 hours. The spent medium was removed, and the cells were gently rinsed twice (2.0 mL per rinse) with PBS. The cells were treated with 2 mL (per flask) of chemical dissociation solution (described above). The flasks were intermittently rocked. The progression of the experiment can be seen in FIG. 25. It was observed that a majority of the cells detached from the surface in clumps within 5 minutes of the start of the procedure. After 15 minutes the size of the clumps had dramatically decreased, and after 22 minutes, it was found that any remaining clumps could be easily dissociated into a relatively uniform single cell suspension using mild pipetting (10 times with a 1 mL pipette). Trypan blue staining revealed that the cell population in both the control and test cultures had very high viabilities (see FIG. 26). It should also be noted that the majority of cells remained viable even after being exposed to the dissociation solution for 10 hours. The single cells generated after 22 minutes were isolated following centrifugation and subsequently inoculated at 10,000 cells/cm$^2$ into 25 cm$^2$ Nunc tissue culture flasks containing a DMEM based medium with 15% FBS (total inoculum was 250,000 cells per tissue culture flask). The cells appeared healthy, retained the ability to attach to a substrate, and were mitotically active (See FIG. 27). Five days post-inoculation, the cultures appeared very similar to those in which the embryonic stem cells were originally tested for their susceptibility to chemical dissociation (i.e. the pre-experimental cultures). The average total number of cells obtained five days after inoculation was over 4×10⁶ cells, indicating that the inoculated cells had undergone more than four doublings. This demonstrates that chemical dissociation is a viable alternative to the undesirable enzymatic method currently employed to detach embryonic stem cells.

Example 15

Dissociation of Mouse Neurospheres using Different Alkaline Solutions

Figure 29:
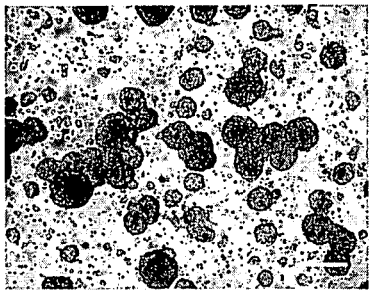
FIG. 29. Photomicrographs showing the effect of serially subculturing (4 passages) cells from mouse neurospheres dissociated with a potassium hydroxide based dissociation solution. At each passage, photomicrographs show the cells prior to dissociation and immediately after dissociation. The cells were passaged in 25 cm$^2$ tissue culture flasks containing 5 mL of PPRF-m4 medium. The flasks were placed in a 37° C. humidified incubator containing 5% $CO_2$. Scale bars=100 μm.
Figure 29:
Figure 29:
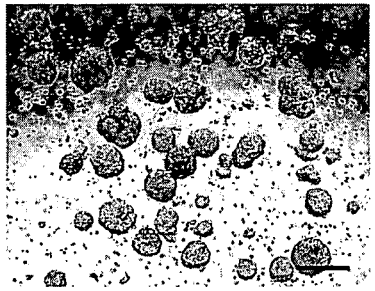
Figure 29:
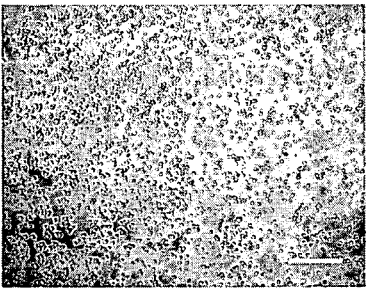
Figure 29:
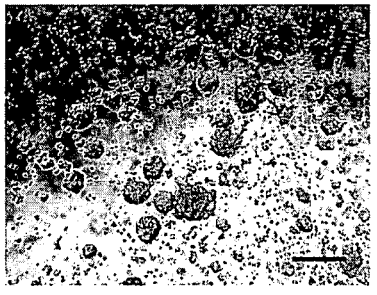
Figure 29:
Figure 29:
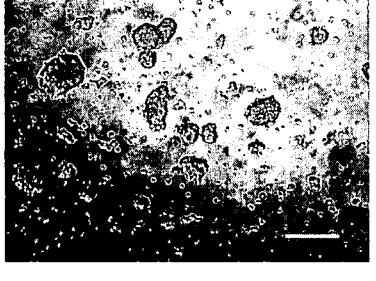
Figure 29:
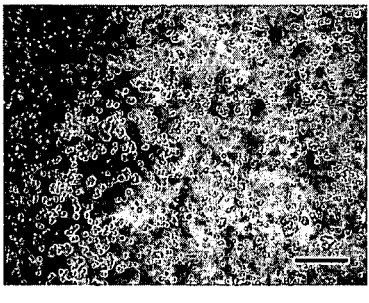
Figure 30:
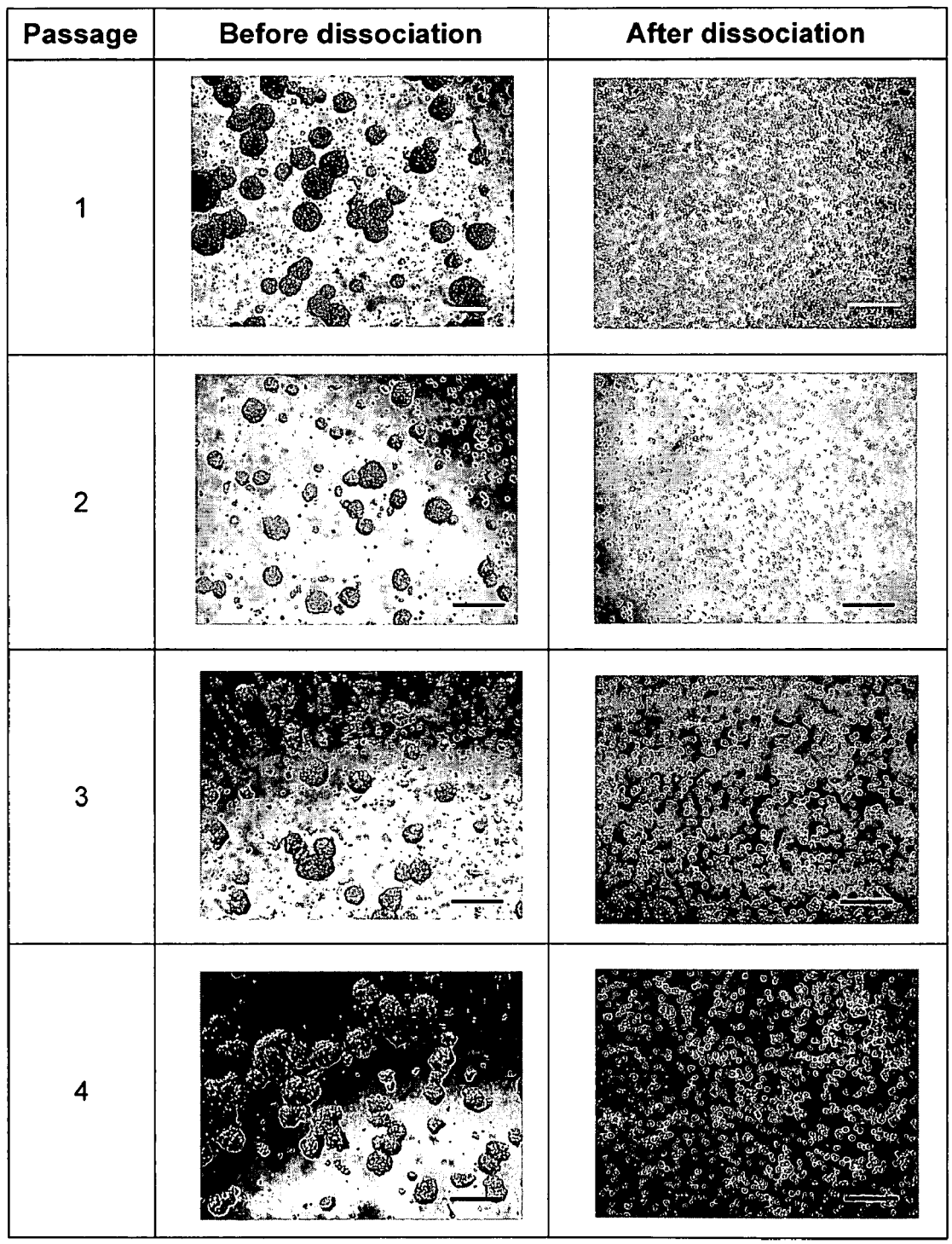
FIG. 30 Photomicrographs showing the effect of serially subculturing (4 passages) cells from mouse neuropsheres dissociated with a sodium phosphate tribasic dodecahydrate based dissociation solution. At each passage, photomicrographs show the cells prior to dissociation and immediately after dissociation. The cells were passaged in 25 cm$^2$ tissue culture flasks containing 5 mL of PPRF-m4 medium. The flasks were placed in a 37° C. humidified incubator containing 5% $CO_2$. Scale bars=100 μm.
Figure 31:
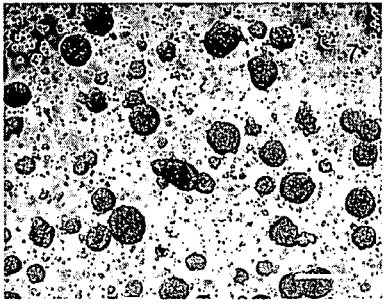
FIG. 31 Photomicrographs showing the effect of serially subculturing (4 passages) of cells from mouse neurospheres dissociated with a sodium carbonate based dissociation solution. At each passage, photomicrographs show the cells prior to dissociation and immediately after dissociation. The cells were passaged in 25 cm$^2$ tissue culture flasks containing 5 mL of PPRF-m4 medium. The flasks were placed in a 37° C. humidified incubator containing 5% $CO_2$. Scale bars=100 μm.
Figure 31:
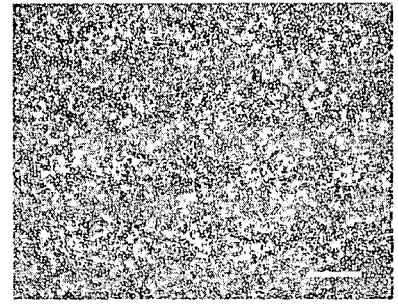
Figure 31:
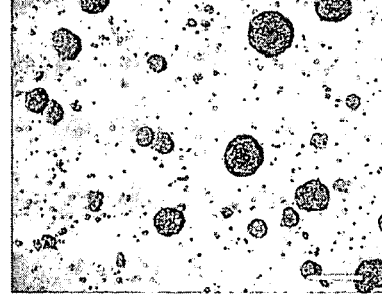
Figure 31:
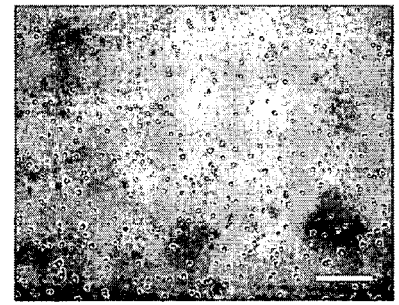
Figure 31:
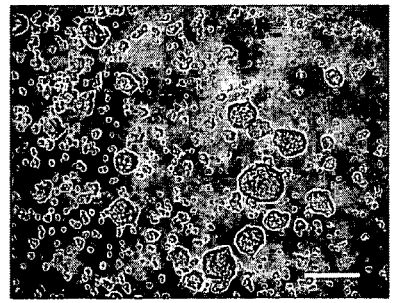
Figure 31:
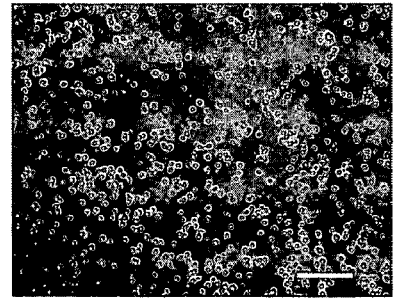
Figure 31:
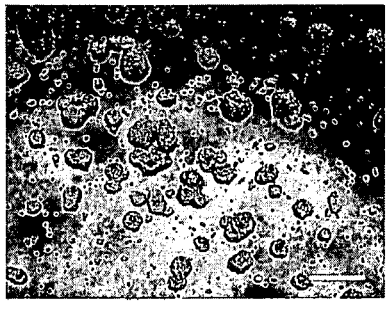
Figure 31:
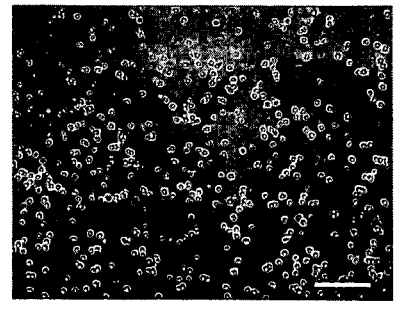
Figure 32:
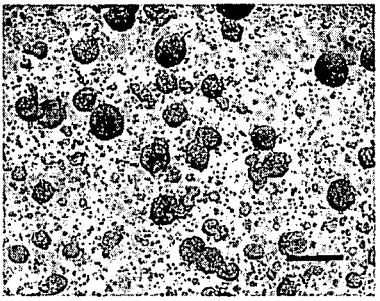
FIG. 32 Photomicrographs showing the effect of serially subculturing (4 passages) cells from mouse neuropsheres dissociated with an ammonium hydroxide based dissociation solution. At each passage, photomicrographs show the cells prior to dissociation and immediately after dissociation. The cells were passaged in 25 cm$^2$ tissue culture flasks containing 5 mL of PPRF-m4 medium. The flasks were placed in a 37° C. humidified incubator containing 5% $CO_2$. Scale bars=100 μm.
Figure 32:
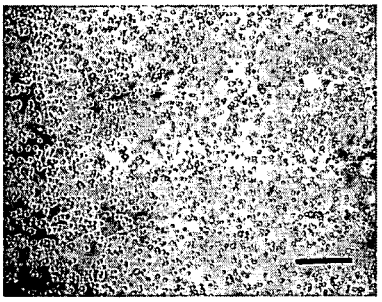
Figure 32:
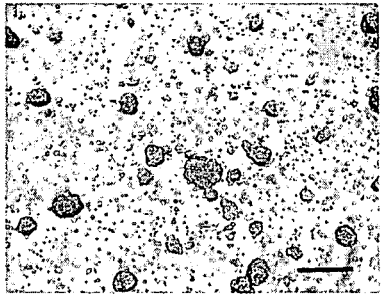
Figure 32:
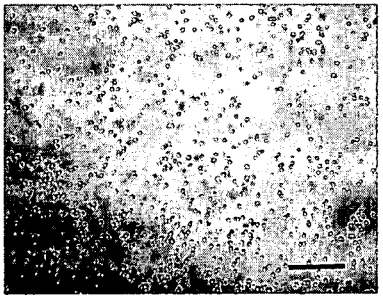
Figure 32:
Figure 32:
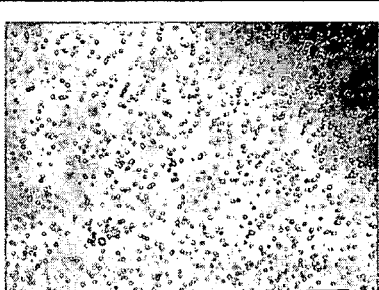
Figure 32:
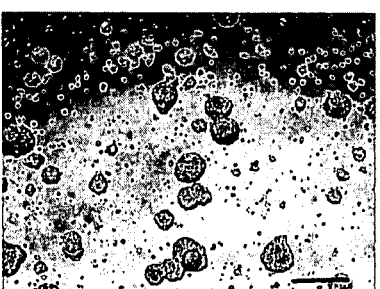
Figure 32:
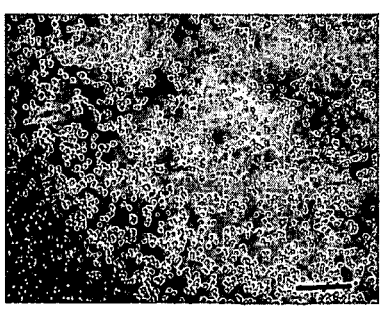

It has been shown that an alkaline dissociation solution containing NaOH is efficient at dissociating mouse neurospheres or cell aggregates. To determine if this result was specific to NaOH, or related to the general alkaline nature of the dissociation solution, a series of other bases were examined for their ability to produce a solution capable of dissociating mouse neurospheres. These included potassium hydroxide (FIG. 29), sodium carbonate (FIG. 31), ammonium hydroxide (FIG. 32), and sodium phosphate tribasic dodecahydrate (FIG. 30). If the dissociation observed using the NaOH solution was the result of pH manipulation, therefore any base could be used to generate an effective alkaline dissociation solution.

Five bases were used to generate dissociation solutions as per the following procedures:
(i) 50 µL of 1.0 M sodium hydroxide was added for every 1 mL of PPRF-m4 medium to generate a sodium hydroxide dissociation solution.
(ii) 60 µL of 0.5 M potassium hydroxide was added for every 1 mL of PPRF-m4 medium to generate a potassium hydroxide dissociation solution.
(iii) 85 µL of 0.5 M sodium phosphate tribasic dodecahydrate was added for every 1 mL of PPRF-m4 medium to generate a sodium phosphate tribasic dodecahydrate dissociation solution.
(iv) 100 µL of 1.0 M sodium carbonate was added for every 1 mL of PPRF-m4 medium to generate a sodium carbonate solution.
(v) 50 µL of 1.0 M ammonium hydroxide was added for every 1 mL of PPRF-m4 medium to generate a weak ammonium hydroxide solution In order to counteract the pH effect of the alkaline dissociation solutions on the cells, an appropriate quantity of acidic medium was added. The acidic medium was generated by adding 50 µL of 1.0 M hydrochloric acid to every 2 mL of PPRF-m4 medium.

Passage 3 mouse neurospheres originally procured from the striata of 14 day old embryonic mice were thawed and passaged twice (passage 5) in PPRF-m4 medium. Cells from these samples were previously dissociated by mechanical dissociation prior to being used for the experiments described here. Passage 5 mouse neurospheres were isolated and centrifuged (10 minutes, 140 g) to form a cell pellet in a 15 mL centrifuge tube. The supernatant was completely removed. The neuropshere aggregates were then resuspended in 200 µL of fresh PPRF-m4 medium at room temperature by pipetting the cell pellet 5 times. 200 µL of a specific alkaline dissociation solution listed above was then added to the tube, and a stopwatch was used to time the procedure for 7 minutes. After 2 minutes and 5 minutes had elapsed, the cells were gently pipetted 5 times. After 7 minutes had elapsed, the acidic medium was added to the mixture to decrease the pH. A volume of 200 µL was added to those samples dissociated with sodium hydroxide, potassium hydroxide or sodium phosphate tribasic dodecahydrate. A volume of 300 µL was added to those samples dissociated using ammonium hydroxide. A volume of 1200 µL was added to those samples dissociated using sodium carbonate. Following the addition of the acidic medium, the cell sample was gently pipetted 5 more times. Photomicrographs were taken prior to the addition of the alkaline dissociation solution and after the addition of the acidic medium (FIG. 28-FIG. 31). The cell concentration and viability of the resulting cell suspension was determined using trypan blue exclusion, and the single cells were inoculated at a cell concentration of 0.75×10⁵ cells/mL, into 25 cm² tissue culture flasks to determine if the alkaline dissociation inhibited the cells from proliferating (Table 2). The cells were subsequently serially subcultured using the same dissociation protocol to which they had previously been exposed. This demonstrates that altering the environmental pH (chemical dissociation) with a series of bases (alkaline solutions), is a viable alternative to mechanical and enzymatic methods that are currently employed to dissociated cell aggregates and generate a single cell suspension.

Example 16

Evaluation of Different Acids for the Generation of a pH Neutralizing Solution

Figure 33:
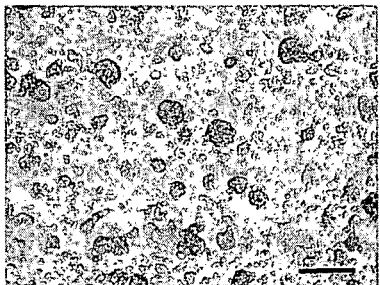
FIG. 33. Photomicrographs showing the effect of serially subculturing (4 passages) cells from mouse neuropsheres dissociated with an NaOH based dissociation solution. The effects of the dissociation solution were counteracted by adding an appropriate quantity of a hydrochloric acid based neutralizing solution. At each passage, photomicrographs show the cells prior to dissociation and immediately after dissociation. The cells were passaged in 25 cm$^2$ tissue culture flasks containing 5 mL of PPRF-m4 medium. The flasks were incubated in a humidified 37° C. environment containing 5% $CO_2$. Scale bars=100 μm.
Figure 33:
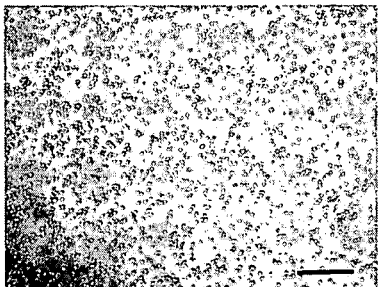
Figure 33:
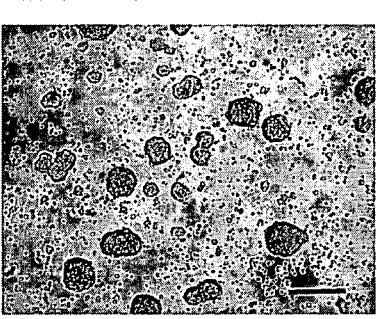
Figure 33:
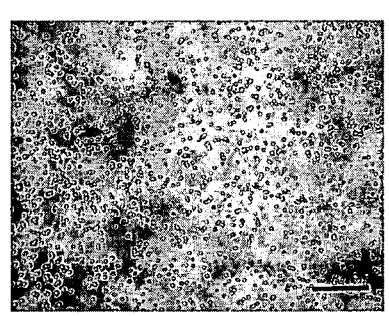
Figure 33:
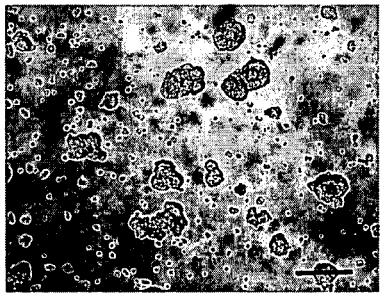
Figure 33:
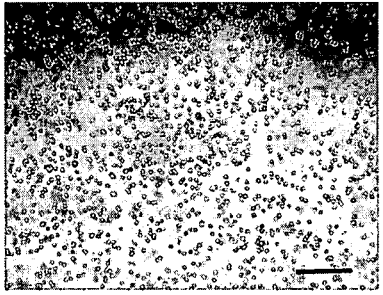
Figure 33:
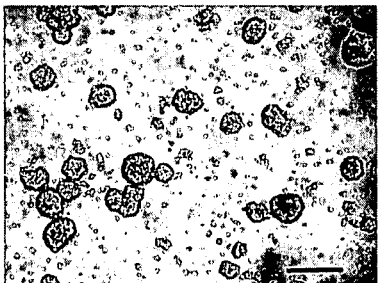
Figure 33:
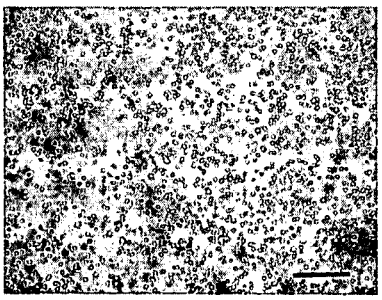
Figure 34:
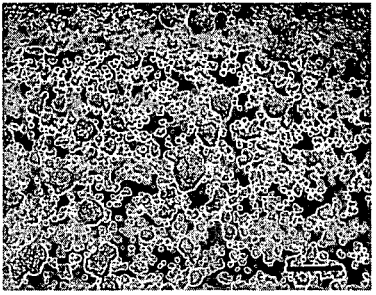
FIG. 34. Photomicrographs showing the effect of serially subculturing (4 passages) cells from mouse neuropsheres dissociated with an NaOH based dissociation solution. The effects of the dissociation solution were counteracted by adding an appropriate quantity of an acetic acid based neutralizing solution. At each passage, photomicrographs show the cells prior to dissociation and immediately after dissociation. The cells were passaged in 25 cm$^2$ tissue culture flasks containing 5 mL of PPRF-m4 medium. The flasks were incubated in a humidified 37° C. environment containing 5% $CO_2$. Scale bars=100 μm FIG. 35. Photomicrographs showing the effect of serially subculturing (4 passages) cells from mouse neuropsheres dissociated with an NaOH based dissociation solution. The effects of the dissociation solution were counteracted by adding an appropriate quantity of a sulfuric acid based neutralizing solution. At each passage, photomicrographs show the cells prior to dissociation and immediately after dissociation. The cells were passaged in 25 cm$^2$ tissue culture flasks containing 5 mL of PPRF-m4 medium. The flasks were incubated in a humidified 37° C. environment containing 5% $CO_2$. Scale bars=100 μm.
Figure 34:
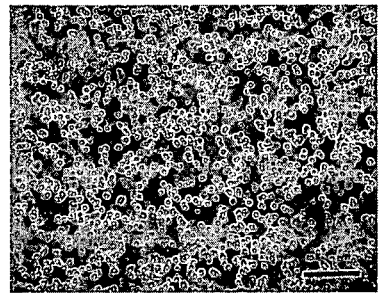
Figure 34:
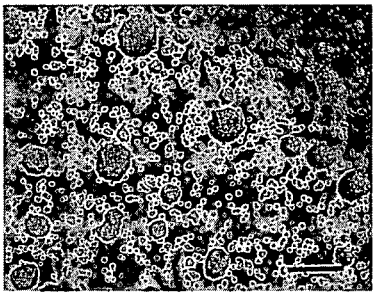
Figure 34:
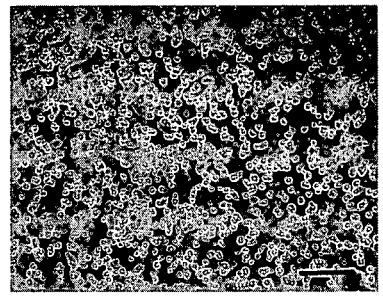
Figure 34:
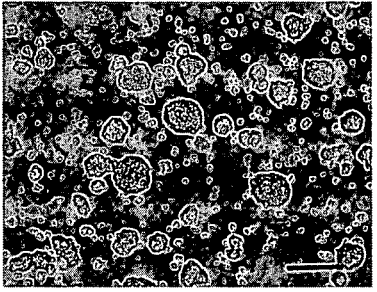
Figure 34:
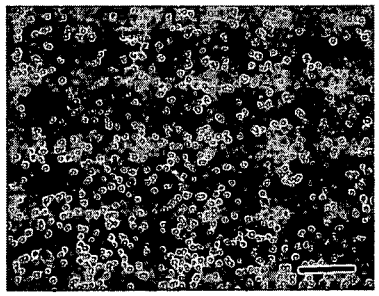
Figure 34:
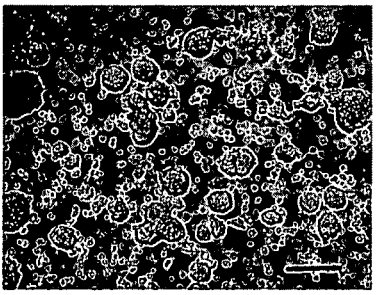
Figure 34:
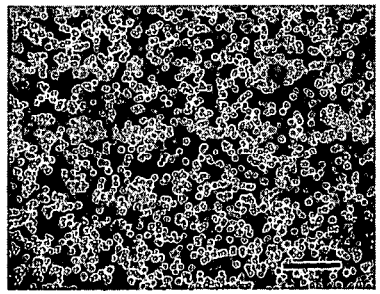
Figure 35:
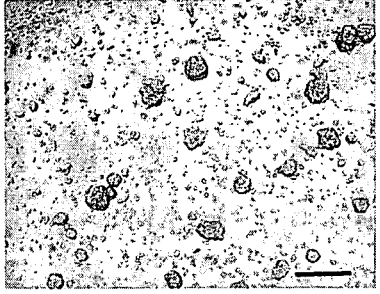
Figure 35:
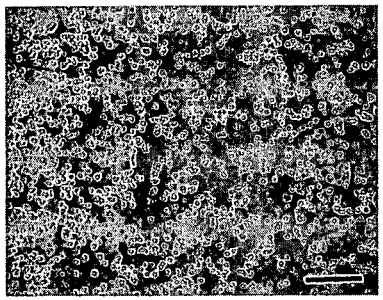
Figure 35:
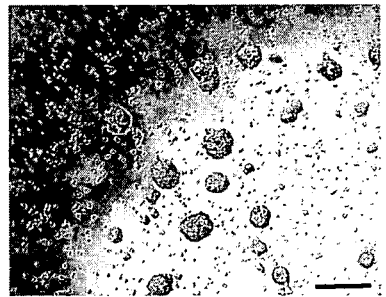
Figure 35:
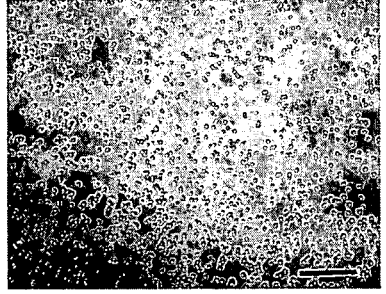
Figure 35:
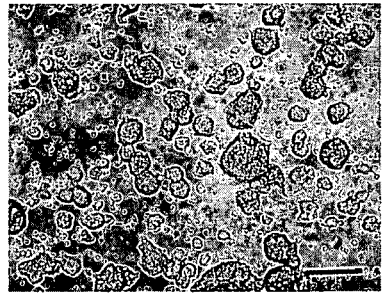
Figure 35:
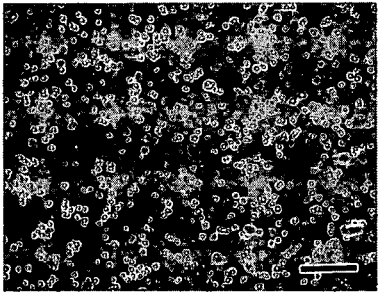
Figure 35:
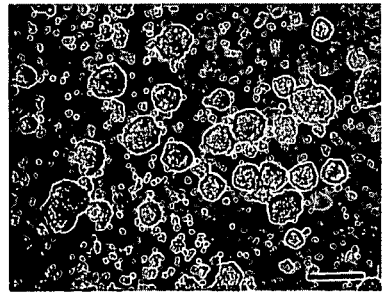
Figure 35:
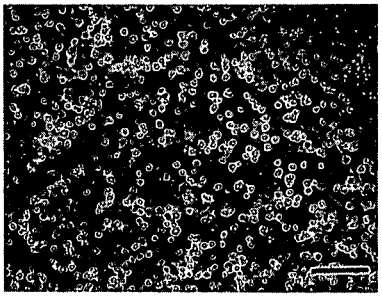
Figure 36:
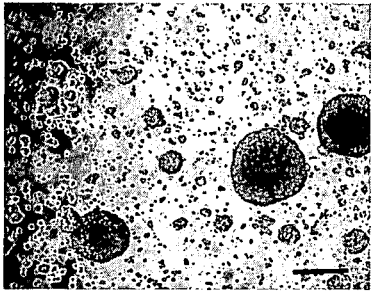
FIG. 36. Photomicrographs showing the effect of serially subculturing (4 passage) cells from mouse neuropsheres dissociated with an NaOH based dissociation solution. The effects of the dissociation solution were counteracted by adding an appropriate quantity of a phosphoric acid based neutralizing solution. At each passage, photomicrographs show the cells prior to dissociation and immediately after dissociation. The cells were passaged in 25 $cm^2$ tissue culture flasks containing 5 mL of PPRF-m4 medium. The flasks were incubated in a humidified 37° C. environment containing 5% $CO_2$. Scale bars=100 μm.
Figure 36:
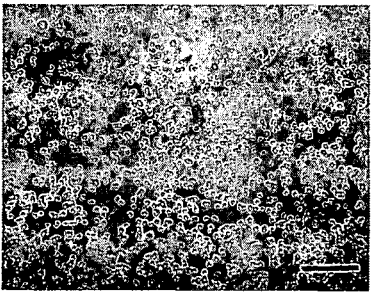
Figure 36:
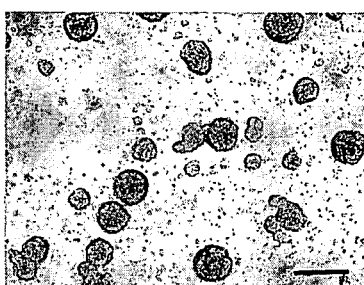
Figure 36:
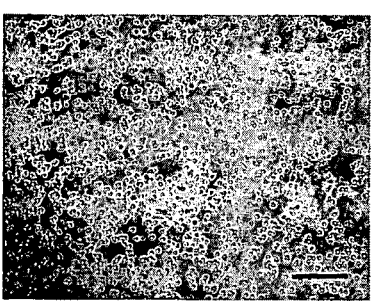
Figure 36:
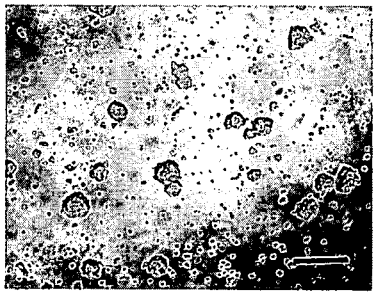
Figure 36:
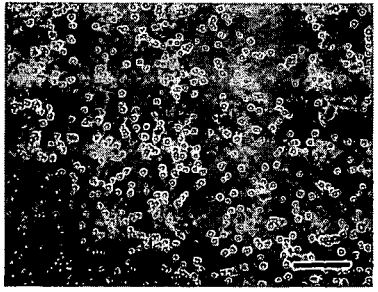
Figure 36:
Figure 36:
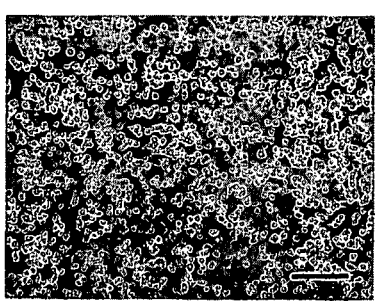

It has been shown that an alkaline dissociation solution containing NaOH is efficient at dissociating mouse neurosphere aggregates. Following dissociation, an acidic pH neutralizing solution generated using HCl is added to decrease the pH of the cell suspension, thereby limiting the time that the cells are exposed to high pH conditions. It has been shown that this combination of dissociation medium and neutralizing solution does not have an adverse effect on subsequent cell proliferation in PPRF-m4 medium. To determine if this pH neutralizing effect is specific to HCl, or related to the general acidic nature of a neutralizing solution, a series of acids were examined for their ability to neutralize the high pH conditions following dissociation. These included hydrochloric acid (FIG. 33), acetic acid (FIG. 34), sulfuric acid (FIG. 35), and phosphoric acid (FIG. 36). If the neutralizing effect of the HCl was simply the result of pH, therefore any acid could be used to generate an effective neutralizing solution.

Five acids were used to generate neutralizing solutions as per the following procedures:
(i) 50 µL of 1.0 M hydrochloric acid was added for every 1 mL of PPRF-m4 medium to generate a hydrochloric acid neutralizing solution.
(ii) 125 µL of 0.5 M acetic acid was added for every 1 mL of PPRF-m4 medium to generate an acetic acid neutralizing solution.
(iii) 50 µL of 0.5 M sulfuric acid was added for every 1 mL of PPRF-m4 medium to generate a sulfuric acid neutralizing solution.
(iv) 75 µL of 0.5 M phosphoric acid was added for every 1 mL of PPRF-m4 medium to generate a phosphoric acid neutralizing solution.

All of the experiments conducted to test the effect of different neutralizing solutions employed an NaOH based dissociation medium to dissociate the cells. This sodium hydroxide dissociation solution was generated by adding 50 µL of 1.0 M sodium hydroxide for every 1 mL of PPRF-m4 medium.

Passage 3 mouse neurospheres originally procured from the striata of 14 day old embryonic mice were thawed and passaged twice (passage 5) in PPRF-m4 medium. These neuropsheres samples were previously dissociated by mechanical dissociation at each passage prior to being used for the experiments described here. Passage 5 mouse neurospheres were isolated and centrifuged (10 minutes, 140 g) to form a cell pellet in a 15 mL centrifuge tube. The supernatant was completely removed. The aggregates were then resuspended in 200 µL of fresh PPRF-m4 medium at room temperature by pipetting the cell pellet 5 times. 200 µL of an NaOH based alkaline dissociation medium was then added to the tube, and a stopwatch was used to time the procedure for 7 minutes. After 2 minutes and 5 minutes had elapsed, the cells were gently pipetted 5 times. After 7 minutes had elapsed, 200 µL of an acidic neutralizing medium was added to the mixture to decrease the pH, and the sample was gently pipetted 5 more times. Photomicrographs were taken prior to the addition of the alkaline dissociation solution and after the addition of the acidic medium (ammonium hydroxide, FIG. 32 and sodium hydroxide, FIG. 33). The cell concentration and viability of the resulting cell suspension was determined using trypan blue exclusion, and the single cells were inoculated at $7.5 \times 10^5$ cells/mL into 25 cm$^2$ tissue culture flasks to determine if the neutralizing solution inhibited the cells from proliferating (Table 3). The cells were subsequently serially subcultured using the same neutralizing solution to which they had previously been exposed. This demonstrates that altering the environmental pH (chemical dissociation) with an alkaline solution, and neutralizing the alkaline pH with a series of acidic solution is a viable alternative to mechanical and enzymatic methods that are currently employed to dissociated cell aggregates and generate a single cell suspension. This demonstrates that the chemical dissociation procedure can be used for dissociating cell aggregates and the pH of the alkaline solution can be increased with a series of bases (alkaline solutions), and neutralized with a series of acidic solutions.

Example 17

Use of the Invention to detach Colonies derived from Primary Human Endothelial Progenitor Cells attached to a Surface It was decided to investigate if the chemical dissociation method was effective for anchorage dependent primary cell types other than cell lines such as CHO cells L-929 murine lung fibroblast cells. Thus, chemical dissociation was evaluated for its ability to detach colonies and adherent cells derived from endothelial progenitor cells (EPCs) in the blood. Mononuclear cells were isolated by Ficoll® density gradient centrifugation and plated on fibronectin-coated 6-well plates at a concentration of $5 \times 10^6$ cells/well in Endothelial Liquid Medium, a M199-based Basal medium supplement with 1% FBS (StemCell Technologies Inc., Vancouver, Canada; www.stemcell.com), for two days to remove mature endothelial cells and monocytes. After two days, the non-adherent cells (which contain EPCs) were then harvested and plated at a concentration of $1 \times 10^6$ cells/mL on fibronectin-coated 24-well plates. Colonies were evaluated 3 days later at day 5. A colony is defined as a central core of "round" cells with more elongated "spindle" shaped cells at the periphery and are classified as early outgrowth CFU-EC.

Figure 37:
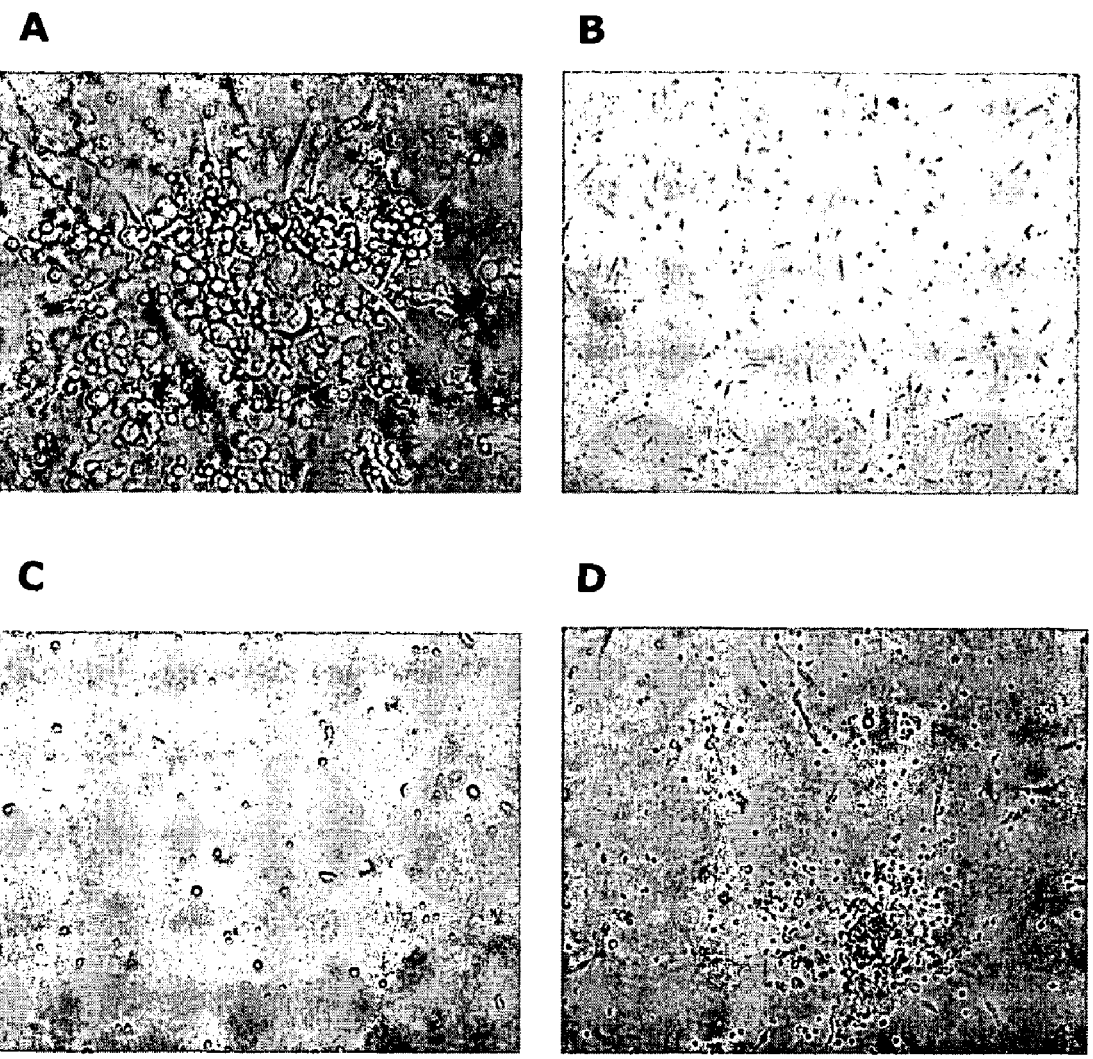
FIG. 37 shows chemical dissociation of primary human endothelial-derived progenitor cells. FIG. (a) shows a typical EPC-derived colony containing round and spindle-shaped cells prior to treatment. EPC-derived colony that were subjected to chemical dissociation solution are shown (b) 5 minutes and (c) 10 minutes after the start of the dissociation procedure. FIG. (d) shows in an area of the culture wells where a EPC-derived colony treated with the chemical dissociation procedure without the addition of EDTA did not dissociate after 10 minutes.

After the 5 day incubation, the spent medium was removed, and the cells were gently rinsed twice (1.0 mL per rinse) with PBS. A volume of 0.5 mL (per well) of chemical dissociation solution (described above) was added to the cells. The progression of the experiment can be seen in FIG. 37. The cells did not detach from the surface after 2 minutes of the start of the procedure. After 5 minutes it was found that gentle pipetting with a 1 mL pipette resulted into a mixture of single cells and cells which were still adherent, and eventually after 10 minutes, this procedure led to the formation of a single cell suspension. Trypan blue staining revealed that the cell population had a cell viability of 97%. The single cells were isolated following centrifugation and subsequently inoculated at $2 \times 10^4$ cells per 24-wells containing Endothelial Liquid Medium, a M199-based Basal medium supplement with 1% FBS. The cells appeared healthy, retained the ability to attach to a substrate and form the sprouting cells but not EPC-derived colonies. The chemical dissociation alkaline solution without EDTA did not completely dissociate all the adherent endothelial cells (FIG. 37). This demonstrates that altering the environmental pH (chemical dissociation) and the addition of a chelating agent such as EDTA, is a viable alternative to mechanical and enzymatic methods that are currently employed to detach anchorage dependent cells and generate a single cell suspension.

Example 18

Use of the Invention to detach Primary Human Mesenchymal Cells from a Surface

The chemical dissociation procedure was also evaluated for its ability to detach another primary cell type, which was human mesenchymal cells obtained from bone marrow. Mesenchymal stem cell (MSC) is distinct from other hematopoietic stem cells. In addition to supporting hematopoietic cells, these cells can differentiate into bone, cartilage, muscle, fat and tendon. Human bone marrow cells were plated oil 24-well plates at a density of $5 \times 10^4$ cells/well in MesenCult® Liquid Medium which consists of a Basal Medium supplemented with a Mesenchymal stem cell stimulatory supplement (MesenCult® MSC Basal Medium (Human) Catalog #05401 and Mesenchymal Stem Cell Stimulatory Supplements (Human) Catalog #05402; StemCell Technologies Inc.; www.stemcell.com), for 14 days. After 10 days, a confluent adherent layer of cells with a fibroblast-like morphology was observed.

Figure 38:
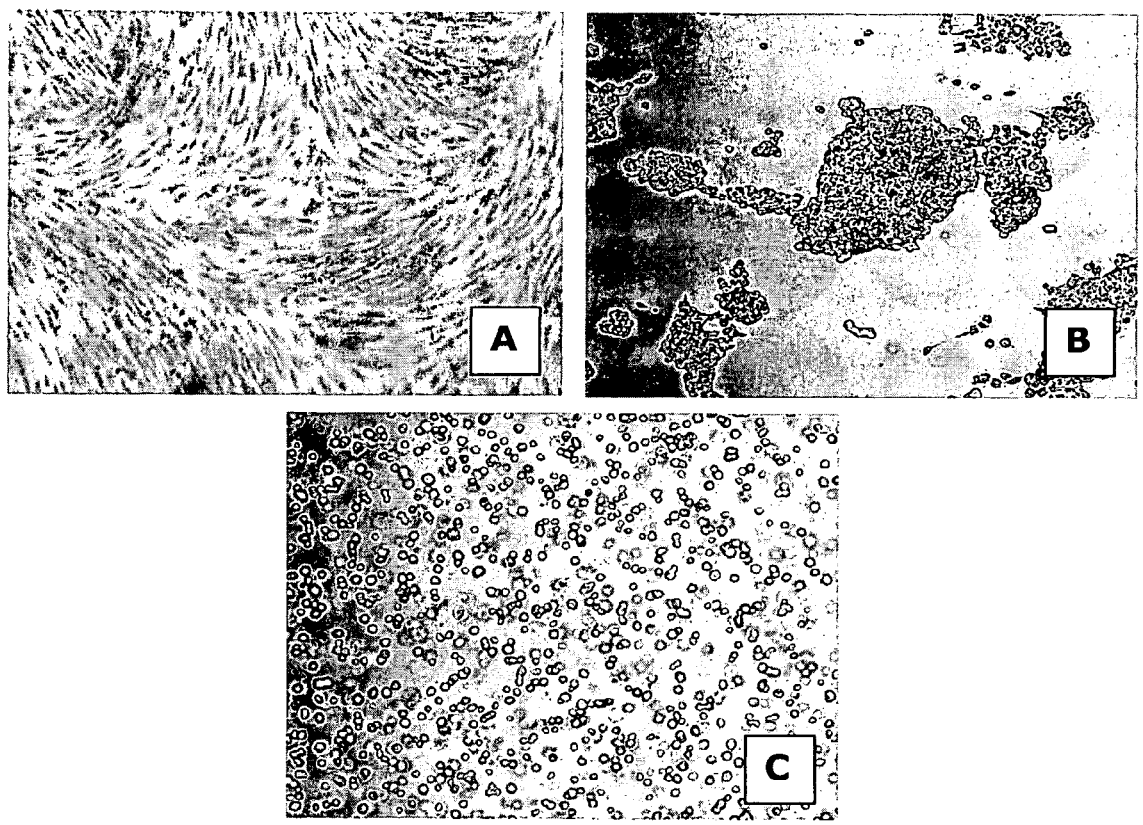
FIG. 38 shows chemical dissociation of primary human mesenchymal cells. FIG. (a) shows a typical confluent layer of mesenchymal cells prior to treatment. Mesenchymal cells were subjected to chemical dissociation solution are shown (b) 5 minutes and (c) 10 minutes after the start of the dissociation procedure.

After the 10-day incubation, the spent medium was removed, and the cells were gently rinsed twice (1.0 mL per rinse) with PBS. A volume of 0.5 mL (per well) of chemical dissociation solution containing EDTA (described above) was added to the cells. The results of the experiment can be seen in FIG. 38. The cells detached from the surface after 2 minutes of the start of the procedure as a sheet of cells. After 5 minutes it was found that gentle pipetting with a 1 mL pipette resulted into a mixture of single cells and cells which were still adherent, and eventually after 10 minutes, this procedure led to the formation of a single cell suspension. Trypan blue staining revealed that the cell population had a very high viability (>85%). The single cells were isolated following centrifugation and subsequently inoculated at $5 \times 10^4$ cells per 24-wells containing MesenCult® Liquid Medium which consists of a Basal Medium supplemented with a Mesenchymal stem cell stimulatory supplement (MesenCult® MSC Basal Medium (Human) Catalog #05401 and Mesenchymal Stem Cell Stimulatory Supplements (Human) Catalog #05402; StemCell Technologies Inc.; www.stemcell.com). The cells appeared healthy, retained the ability to attach to a substrate and form the classic mesenchymal "fibroblast-like" adherent cells. This demonstrates that altering the environmental pH (chemical dissociation) and the addition of EDTA can be used to detach anchorage dependent cells and generate a single cell suspension.

Example 19

Use of Different Alkaline Solutions in the Invention to Detach Mouse Embryonic Stem Cells (ES)

It has been shown that a dissociation solution containing NaOH is efficient at detaching and dissociating murine embryonic stem cells. To determine if this result was specific to NaOH, a series of other bases were examined for their ability to produce a solution capable of detaching and dissociating mouse embryonic stem cells. These included potassium hydroxide, sodium carbonate, ammonium hydroxide, and sodium phosphate tribasic dodecahydrate.

A total of five different dissociation solutions were tested for their ability to detach and dissociate mouse embryonic stem cells. Each solution was made by adding a different base to a basal solution (1×PBS solution containing 10 mM EDTA). The solutions were made as per the following procedures:

(vi) 12.5 μL of 1.0 M sodium hydroxide was added for every 1 mL of basal solution to generate a sodium hydroxide dissociation solution.

(vii) 25 μL of 0.5 M potassium hydroxide was added for every 1 mL of basal solution to generate a potassium hydroxide dissociation solution.

(viii) 18 μL of 0.5 M sodium phosphate tribasic dodecahydrate was added for every 1 mL of basal solution to generate a sodium phosphate tribasic dodecahydrate dissociation solution.

(ix) 7.5 μL of 1.0 M sodium carbonate was added for every 1 mL of basal solution to generate a sodium carbonate solution.

Figure 39:
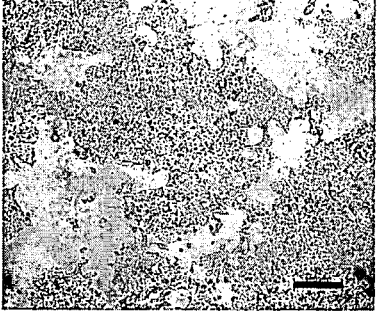
FIG. 39. Photomicrographs showing the effect of using dissociation solutions generated by adding various bases (specified in the figure) to 1×PBS containing 10 mM EDTA on mouse ES cells. Also shown is the result of using a trypsin/EDTA solution (the method currently accepted as a standard protocol in this area). Photomicrographs show the cells prior to and after detachment and dissociation. The cells were passaged in 25 $cm^2$ tissue culture flasks that were incubated in a humidified 37° C. environment containing 5% $CO_2$. Scale bars=100 μm.
Figure 39:
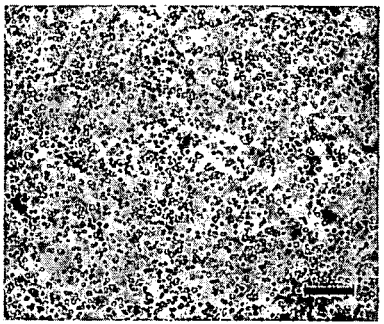
Figure 39:
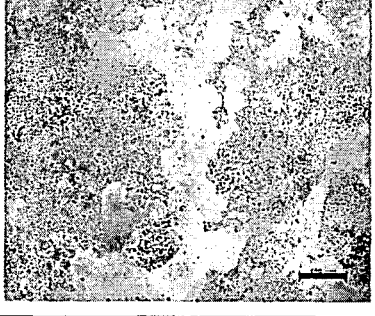
Figure 39:
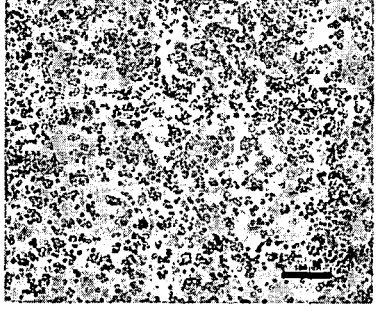
Figure 39:
Figure 39:
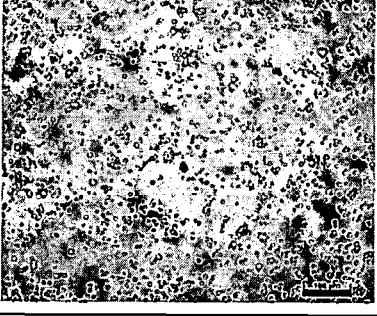
Figure 40:
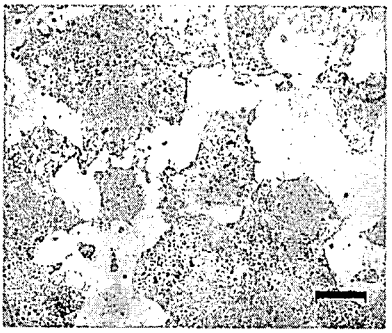
FIG. 40. Photomicrographs showing the effect of using dissociation solutions generated by adding various bases (specified in the figure) to 1×PBS containing 10 mM EDTA on mouse ES cells. Photomicrographs show the cells prior to and after detachment and dissociation. The cells were passaged in 25 $cm^2$ tissue culture flasks that were incubated in a humidified 37° C. environment containing 5% $CO_2$. Scale bars=100 μm.
Figure 40:
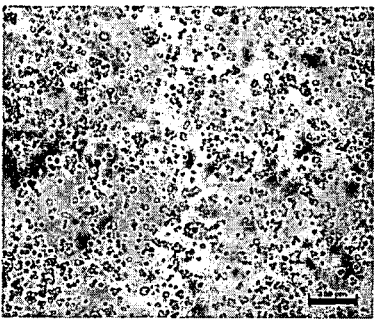
Figure 40:
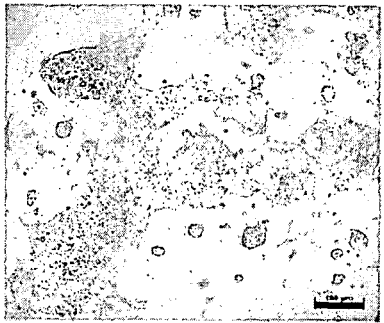
Figure 40:
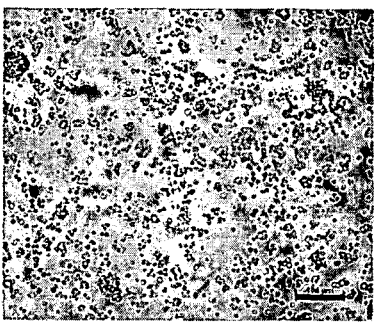
Figure 40:
Figure 40:
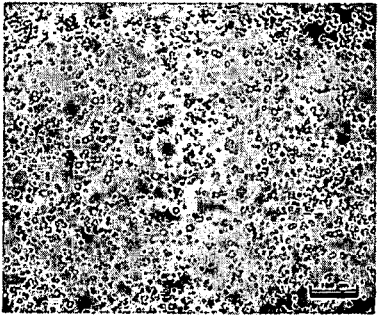

(x) 10 μL of 1.0 M ammonium hydroxide was added for every 1 mL of basal solution to generate a weak ammonium hydroxide solution Mouse embryonic stem (ES) at passage 8 were dissociated using enzymatic dissociation (0.25% trypsin with EDTA) and sub-cultured twice in standard ES cell culture medium prior to being used for the experiments described here. Hence, the passage 10 ES cells were cultured in 25 cm$^2$ culture flasks until they reached 80% confluency, at which time the spent medium was removed and the cells were gently rinsed twice with 5.0 mL of 1×PBS. A volume of 2.0 mL of the appropriate dissociation solution was then added to each 25 cm$^2$ tissue culture flask, and the flasks were placed in an incubator at 37° C. The flasks were rocked intermittently over a period of 22 minutes after which gentle pipetting was used to break up any remaining clumps of cells. The cell suspension was collected and added to a sterile 15 mL tube containing 5.0 mL of medium and then centrifuged for 5 minutes at 1000 rpm. Photomicrographs were taken prior to the addition of the dissociation solution and after the cell suspension was added to the medium (FIG. 39 and FIG. 40). After centrifugation, the supernatant was discarded and the pellet was resuspended in 1.0 mL of medium. The cell concentration and viability of the resulting cell suspension was determined using trypan blue exclusion and the single cells were inoculated at a cell concentration of 3.13×10$^4$ cells/mL into 25 cm$^2$ tissue culture flasks to determine if the dissociation inhibited the cells from proliferating. The cells were subsequently serially subcultured using the same dissociation protocol to which they had previously been exposed.

Example 20

Dissociation of Adherent Cell Lines (L929 cell) using Alkaline Chelating Solutions It has previously been shown that an alkaline dissociation solution containing the chelating agent EDTA together with NaOH is efficient at detaching adherent cells attached to a surface, and then dissociating them into a single cell suspension. To determine if this result was specific to EDTA, or related to the general chelating nature of EDTA, the chelating agents EGTA and NTA (in conjunction with NaOH) were examined for their ability to produce a solution capable of dissociating adherent cell lines. In this case the cell lines tested were L929 cells and CHO cells (described below).

Three different chelating agents were used in conjunction with NaOH to generate three cell dissociation solutions as per the following procedures:

(xi) A 0.01M EDTA solution was generated by dissolving 37.2 mg of EDTA in 10 mL of 1×PBS. The pH of the EDTA solution was raised to 9.5 by adding 20 μL of 1.0 N NaOH for every 1.0 mL of EDTA solution. The solution was then filtered through a 0.2 μm filter. This solution was referred to as the NaOH-EDTA dissociation solution.

(xii) A 0.01M EGTA solution was generated by dissolving 38.0 mg of EGTA in 1.0 mL of 1.0 N NaOH. The EGTA solution was added to 1.0 mL of 10×PBS and 8.0 mL of double-distilled H$_2$O. The pH of this solution was adjusted to 9.5 by adding glacial acetic acid. The solution was then filtered through a 0.2 μm filter. This solution was referred to as the NaOH-EGTA dissociation solution.

(xiii) A 0.01M NTA solution was generated by dissolving 19.1 mg of NTA in 1.0 mL of 1.0N NaOH. A volume of 1.0 mL of this solution was then added to 1.0 mL of 10×PBS and 8.0 mL of double-distilled H$_2$O. The pH of this solution was then adjusted to 9.5 by adding glacial acetic acid. The solution was then filtered through a 0.2 μm filter. This solution was referred to as the NaOH-NTA dissociation solution.

In order to counteract the pH effect of the alkaline dissociation solutions on the cells, an appropriate quantity of an acidic medium was added. The NaOH-EDTA solution and NaOH-EGTA solutions were counteracted using an acidic medium comprised of 20 μL of 1.0 M hydrochloric acid for every 1.0 mL of 1×PBS. The NaOH-NTA solution was counteracted using an acidic medium comprised of 10 μL of 1.0 M hydrochloric acid for every 1.0 mL of 1×PBS.

Figure 41:
FIG. 41. Photomicrographs showing the effect of serially subculturing (4 passages) L-929 cells using an NaOH-EDTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.
Figure 41:
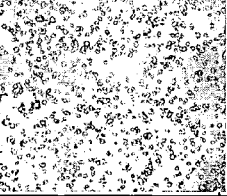
Figure 41:
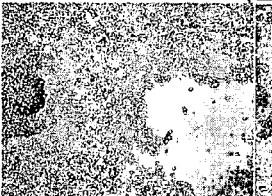
Figure 41:
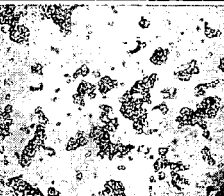
Figure 41:
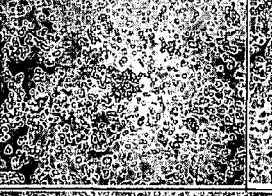
Figure 41:
Figure 41:
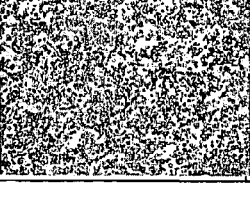
Figure 41:
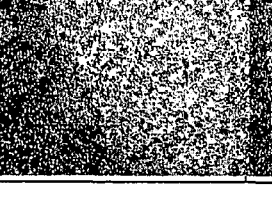
Figure 41:
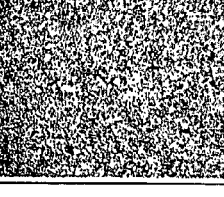
Figure 47:
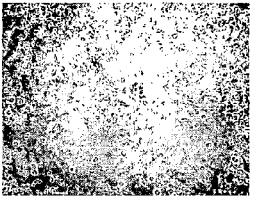
FIG. 47. Photomicrographs showing the effect of serially subculturing (4 passages) L-929 cells after dissociation using an NaOH-NTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.
Figure 47:
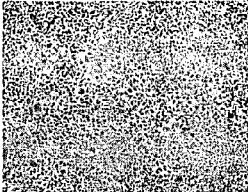
Figure 47:
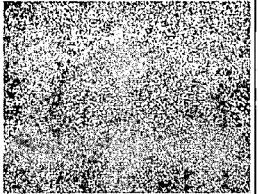
Figure 47:
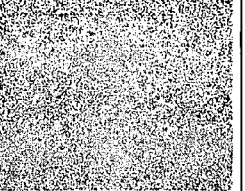
Figure 47:
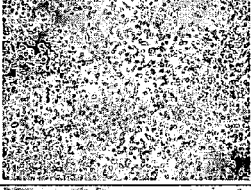
Figure 47:
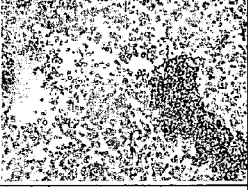
Figure 47:
Figure 47:
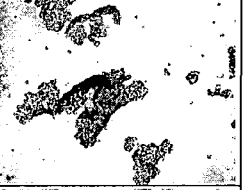
Figure 47:
Figure 47:
Figure 47:
Figure 47:
Figure 47:
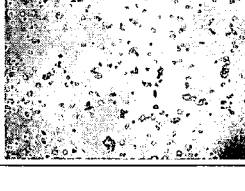
Figure 47:
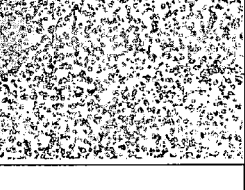
Figure 47:
Figure 47:
Figure 47:

The protocols used to detach and dissociate L-929 cells are provided below. L929 cells were thawed and passaged twice in 1×DMEM containing 7.5% sodium bicarbonate, 10% FBS and 1% penicillin/streptomycin (adherent cell medium). Trypsin/EDTA was used to dissociate the cells for the passages prior to the experiments described here. L929 cells (passage 2) in 25 cm$^2$ tissue culture flasks were detached and dissociated by drawing off the supernatant, rinsing twice with 1×PBS solution and adding 2.0 mL of the appropriate dissociation solution to the tissue culture flask. The flask was then intermittently rocked and the solution was gently pipetted after 5 minutes and 10 minutes had elapsed. The acidic neutralizing medium was then added to decrease the pH. Photomicrographs were taken prior to the addition of the dissociation solution, during the dissociation process and after the addition of the neutralizing medium (FIG. 41). The cell suspension was then withdrawn and centrifuged (5 minutes, 140 g) to form a cell pellet in a 15 mL centrifuge tube. The supernatant was completely removed. The cells were then resuspended in 10 mL of fresh medium at room temperature by pipetting the cell pellet 5 times. The cell concentration and viability of the cell suspension was determined using trypan blue exclusion, and the single cells were inoculated at a density of 5000 cells/cm$^2$ into 25 cm$^2$ tissue culture flasks to determine if the dissociation method inhibited the cells from proliferating. The cells were subsequently serially subcultured using the same dissociation solution to which they had been previously exposed (Table 5). The results show that the various chelating agents (FIG. 45, NaOH-EDTA; FIG. 46 NaOH-EGTA; FIG. 47, NaOH-NTA) can be used in combination with the alkaline solution (NaOH) to dissociate adherent cells such as L929 from the surface that is attached to during growth.

Example 21

Figure 42:
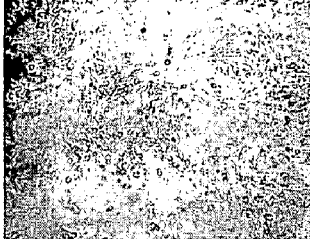
FIG. 42. Photomicrographs showing the effect of serially subculturing (4 passages) CHO cells using an NaOH-EDTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.
Figure 42:
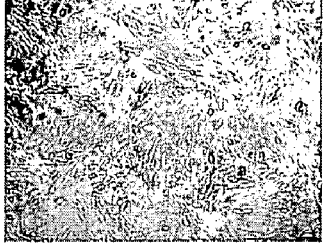
Figure 42:
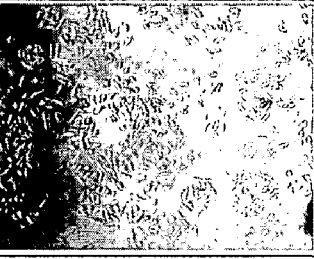
Figure 42:
Figure 42:
Figure 42:
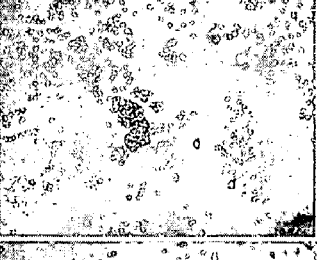
Figure 42:
Figure 42:
Figure 42:
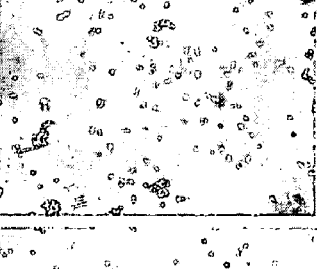
Figure 42:
Figure 42:
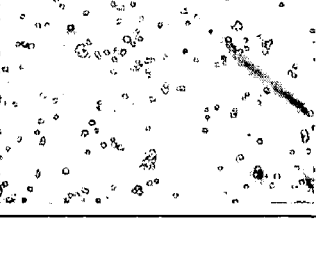
Figure 42:
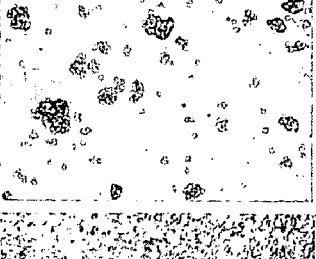
Figure 42:
Figure 42:
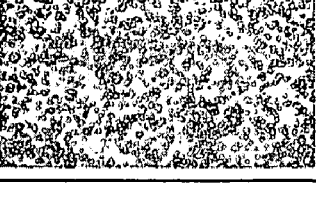
Figure 43:
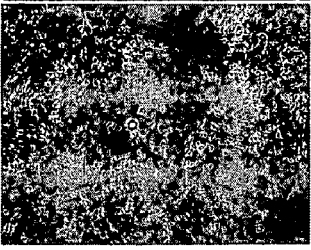
FIG. 43. Photomicrographs showing the effect of serially subculturing (4 passages) CHO cells using an NaOH-EGTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.
Figure 43:
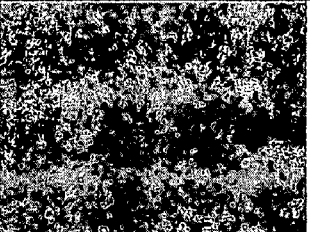
Figure 43:
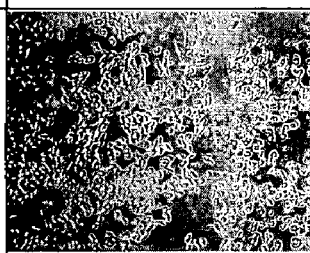
Figure 43:
Figure 43:
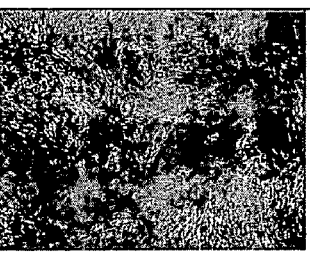
Figure 43:
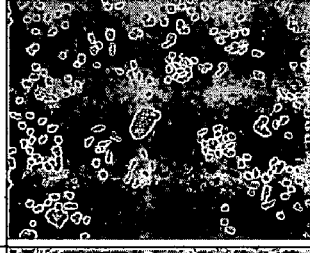
Figure 43:
Figure 43:
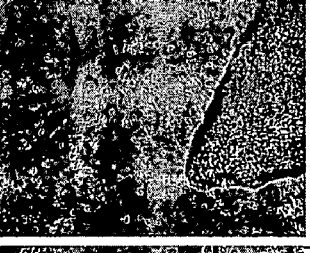
Figure 43:
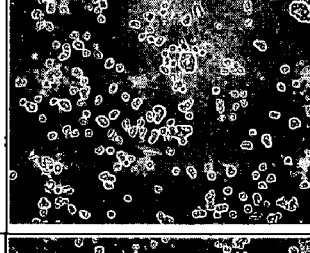
Figure 43:
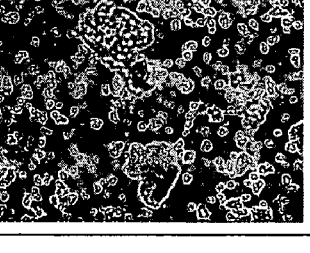
Figure 43:
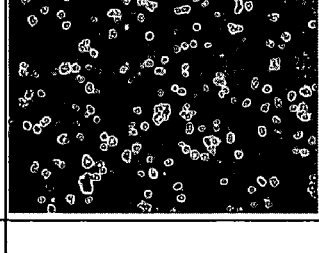
Figure 43:
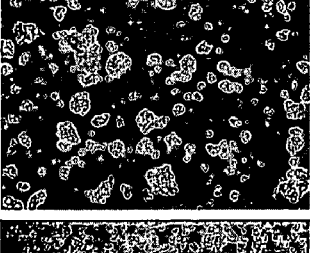
Figure 43:
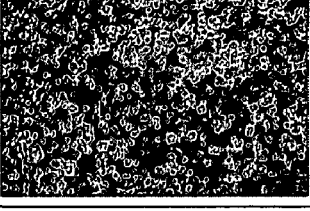
Figure 44:
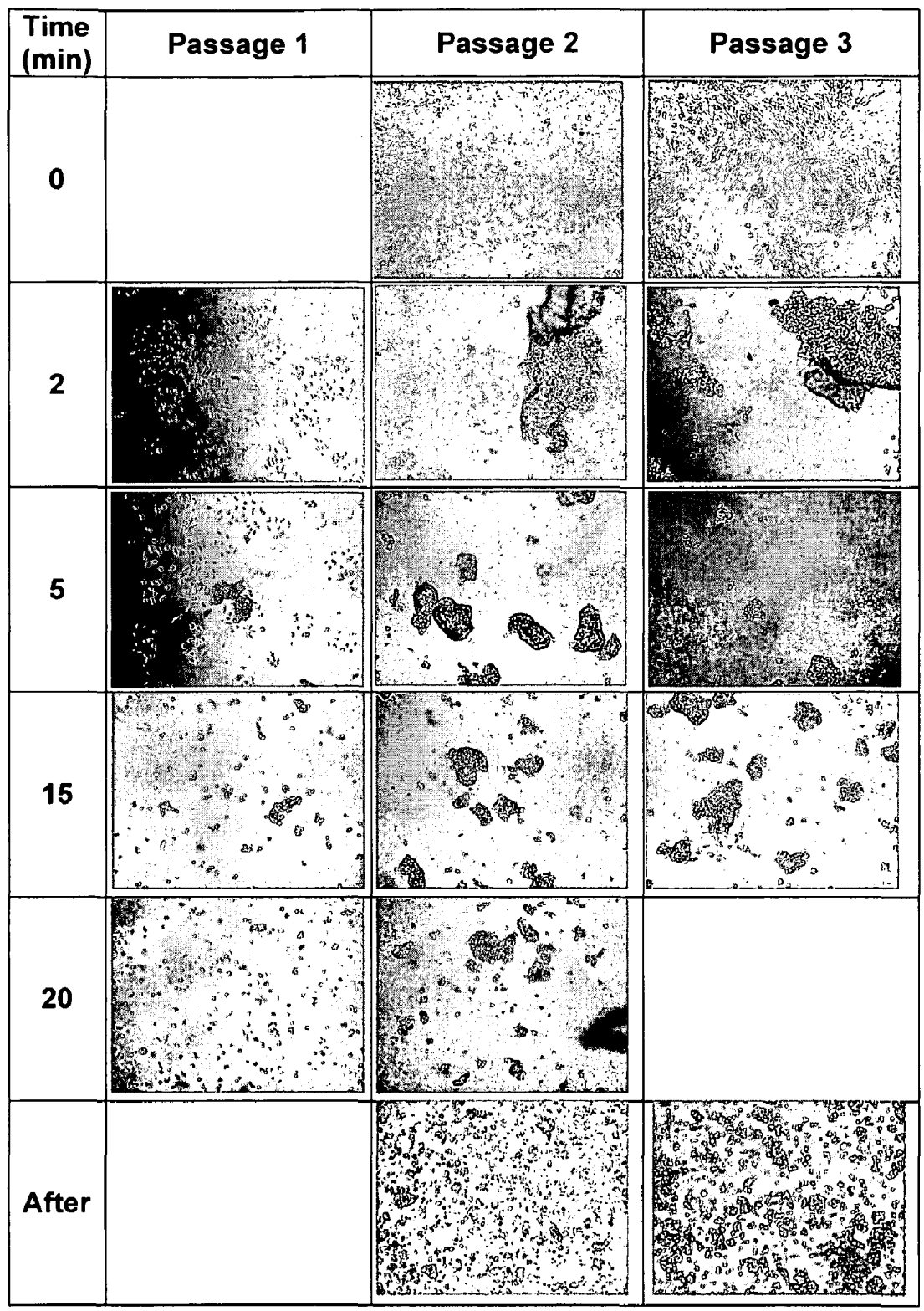
FIG. 44. Photomicrographs showing the effect of serially subculturing (4 passages) CHO cells using an NaOH-NTA dissociation solution. At each passage, photomicrographs show the cells detaching from the surface and dissociating over time in suspension. The cells were passaged in 25 $cm^2$ tissue culture flasks containing an adherent cell medium. The flasks were incubated in a humidified 37° C. environment containing 5% $CO_2$.

Dissociation of Adherent Cell Lines (CHO Cells) Using Alkaline Chelating Solutions The dissociation solutions used to dissociate CHO cells were made up as in Example 20. CHO cells were thawed and passaged twice in 1×DMEM containing 7.5% sodium bicarbonate, 10% FBS and 1% penicillin/streptomycin (adherent cell medium). Trypsin/EDTA was used to dissociate the cells for the passages prior to the experiments described here. CHO cells (passage 2) in 25 cm$^2$ tissue culture flasks were detached and dissociated by drawing off the supernatant, rinsing twice with 1×PBS solution and adding 2.0 mL of the appropriate dissociation solution to the tissue culture flask. The flask was then intermittently rocked and the solution was gently pipetted after 5, 10, and 15 minutes had elapsed. The acidic neutralizing medium was then added to decrease the pH. Photomicrographs were taken prior to the addition of the dissociation solution, during the dissociation process and after the addition of the neutralizing medium (FIG. 42-44). The cell suspension was then withdrawn and centrifuged (5 minutes, 140 g) to form a cell pellet in a 15 mL centrifuge tube. The supernatant was completely removed. The cells were then resuspended in 5 mL of fresh medium at room temperature by pipetting the cell pellet 5 times. The cell concentration and viability of the cell suspension was determined using trypan blue exclusion, and the single cells were inoculated at a density of 15000 cells/cm$^2$ into 25 cm$^2$ tissue culture flasks to determine if the dissociation method inhibited the cells from proliferating. The cells were subsequently serially subcultured using the same dissociation solution to which they had been previously exposed (Table 6). The results show that the various chelating agents EDTA (FIG. 42), EGTA (FIG. 43) and NTA (FIG. 44) can be used in combination with the alkaline solution (NaOH) to dissociate the adherent cell line CHO from the surface which it is attached to during growth. These cells can be subsequently passaged to generate further cell lines.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Dissociation Method | Condition | % of total analyzed particle with a given range of FS values | | | |
|---|---|---|---|---|---|
| | | 0-200 | 200-300 | 300-600 | 600-800 |
| Mechanical | % of total analyzed particles | 71.8 | 2.9 | 24.5 | 0.8 |
| | % of intact cells | 4.9 | 9.8 | 82.3 | 2.7 |
| Chemical | % of total analyzed particles | 59.5 | 2.1 | 36.9 | 1.5 |
| | % of intact cells | 3.7 | 5.0 | 87.7 | 3.4 |

TABLE 2

| Base used in Dissociation Solution | Passage | Average Viable Cell Conc. (10$^5$ cells/mL) | Average Cell Viability (%) | Fold Increase in number of viable cells |
|---|---|---|---|---|
| NaOH | 1 | 8.7 | 84 | 12 |
| | 2 | 12.9 | 90 | 17 |
| | 3 | 8.8 | 91 | 12 |
| | 4 | 13.9 | 90 | 18 |
| KOH | 1 | 7.1 | 81 | 9.4 |
| | 2 | 8.7 | 85 | 12 |
| | 3 | 13.9 | 9 | 18 |
| | 4 | 19.0 | 93 | 25 |
| Sodium Phosphate | 1 | 11.5 | 87 | 15 |
| | 2 | 7.3 | 89 | 10 |
| | 3 | 13.9 | 89 | 18 |
| | 4 | 10.2 | 93 | 14 |
| Sodium Carbonate | 1 | 7.7 | 84 | 10 |
| | 2 | 11.4 | 88 | 15 |
| | 3 | 11.1 | 86 | 15 |
| | 4 | 8.7 | 89 | 12 |
| Ammonium Hydroxide | 1 | 6.2 | 91 | 8 |
| | 2 | 8.4 | 89 | 11 |
| | 3 | 10.5 | 86 | 14 |
| | 4 | 9.1 | 90 | 12 |

TABLE 3

| Acid used in Neutralizing Solution | Passage | Average Viable Cell Conc. (10$^5$ cells/mL) | Average Cell Viability (%) | Fold Increase in number of viable cells |
|---|---|---|---|---|
| HCl | 1 | 10.9 | 91 | 14 |
| | 2 | 12.7 | 92 | 17 |
| | 3 | 9.0 | 92 | 12 |
| | 4 | 10.2 | 89 | 14 |
| Acetic Acid | 1 | 9.6 | 91 | 13 |
| | 2 | 14.3 | 90 | 20 |
| | 3 | 7.2 | 91 | 10 |
| | 4 | 12.8 | 92 | 17 |
| Sulfuric Acid | 1 | 10.5 | 89 | 14 |
| | 2 | 13.1 | 95 | 18 |
| | 3 | 6.1 | 92 | 8 |
| | 4 | 11.3 | 92 | 15 |
| Phosphoric Acid | 1 | 11.5 | 91 | 15 |
| | 2 | 17.3 | 91 | 23 |
| | 3 | 4.2 | 94 | 6 |
| | 4 | 11.8 | 90 | 16 |

TABLE 4

| Base used in Dissociation Solution | Passage | Average Viable Cell Conc. ($10^5$ cells/mL) | Average Cell Viability (%) | Fold Increase in number of viable cells |
|---|---|---|---|---|
| Sodium Hydroxide | 1 | 3.6 | 90 | 12 |
| | 2 | 6.2 | 87 | 20 |
| | 3 | 7.5 | 87 | 24 |
| | 4 | 5.7 | 94 | 18 |
| Potassium Hydroxide | 1 | 4.3 | 89 | 14 |
| | 2 | 1.8 | 86 | 6 |
| | 3 | 3.2 | 81 | 10 |
| | 4 | 4.4 | 81 | 14 |
| Sodium Phosphate | 1 | 4.2 | 88 | 14 |
| | 2 | 2.0 | 91 | 6 |
| | 3 | 4.1 | 87 | 13 |
| | 4 | 6.7 | 84 | 21 |
| Sodium Carbonate | 1 | 3.7 | 88 | 12 |
| | 2 | 3.6 | 90 | 11 |
| | 3 | 7.7 | 88 | 25 |
| | 4 | 6.8 | 90 | 22 |
| Ammonium Hydroxide | 1 | 4.1 | 84 | 13 |
| | 2 | 1.4 | 86 | 4 |
| | 3 | 2.7 | 84 | 8 |
| | 4 | 5.1 | 82 | 16 |

TABLE 5

| Dissociation Solution | Passage | Average Viable Cell Conc. ($10^4$ cells/cm$^2$) | Average Cell Viability (%) |
|---|---|---|---|
| NaOH-EDTA | 1 | 12.1 | 96 |
| | 2 | 15.9 | 97 |
| | 3 | 18.7 | 96 |
| | 4 | 31.6 | 96 |
| NaOH-EGTA | 1 | 11.7 | 99 |
| | 2 | 17.2 | 96 |
| | 3 | 24.9 | 96 |
| | 4 | 34.5 | 94 |
| NaOH-NTA | 1 | 13.2 | 98 |
| | 2 | 20.6 | 97 |
| | 3 | 23.8 | 95 |
| | 4 | 32.1 | 96 |

TABLE 6

| Dissociation Solution | Passage | Average Viable Cell Conc. ($10^4$ cells/cm$^2$) | Average Cell Viability (%) |
|---|---|---|---|
| NaOH-EDTA | 1 | 29.1 | 97 |
| | 2 | 11.4 | 93 |
| | 3 | 7.2 | 93 |
| NaOH-EGTA | 1 | 26.9 | 94 |
| | 2 | 5.0 | 78 |
| | 3 | 16.2 | 77 |
| NaOH-NTA | 1 | 18.6 | 94 |
| | 2 | 5.3 | 86 |
| | 3 | 3.8 | 83 |

REFERENCES

1. Alam, S. (2003) Cell Cycle Kinetics of Expanding Populations of Mammalian Neural Stem Cells. M. Sc. Thesis, University of Calgary, Alberta, Canada
2. Alberts, B., Johnson, A., Lewis, J., Raff, M., Roberts, K., Walter, P. (2002) *Molecular Biology of the Cell—Fourth Edition*; Garland Science, New York
3. Allen, C. N., Brady, R., Swann, J., Hori, N., Carpenter, D. O. (1988) N-methyl-D-aspartate (NMDA) receptors are inactivated by trypsin. *Brain Res.* 458:147-150
4. Kallos, M. S. (1999) The development of bioreactor protocols for the large scale expansion of mammalian neural stem cells. *Ph.D. Thesis*. The University of Calgary, Calgary, Alberta.
5. Lee, S. H., Lumelsky, N., Auerbach, J. M., McKay, R. D. (2000) Efficient generation of midbrain and hindbrain neurons from mouse embryonic stem cells. *Nat. Biotechnol.* 18:675-679
6. Martin, F. C., Wiley, C. A. (1994) An alternative method for obtaining high-viability cell suspensions from neonatal mouse brain. *J. Neurosci. Methods* 55(1):99-104
7. Moran, L. A., Scrimgeour, K. G., Horton, H. R., Ochs, R. S., Rawn, J. D. (1994) Biochemistry, $2^{nd}$ Ed. L Patterson Publishers, Prentice Hall, Toronto. Pp. (4-1)-(5-59)
8. Murayama, A., Matsuzaki, Y., Kawaguchi, A., Shimazaki, T., Okano, H. (2002) Flow cytometric analysis of neural stem cells in the developing and adult mouse brain. *J. Neurosci. Res.* 69(6):837-47
9. O'Connor, T. J., Vescovi, A. L. and Reynolds, B. A. Isolation and Propagation of Stem Cells from Various Regions of the Embryonic Mammalian Central Nervous System. In Cell Biology: A laboratory Handbook. ed. Julio E. Celis. 1998. Volume 1, pp 149-153.
10. Reynolds, B. A., Weiss, S. (1992). Generation of neurons and astrocytes from isolated cells of the adult mammalian central nervous system. *Science* 255:1707-1710
11. Reynolds, B. A., Weiss, S. (1996). Clonal and Population Analyses Demonstrate that an EGF-Responsive Mammalian Embryonic CNS Precursor is a Stem Cell. *Dev. Biol.* 175:1-13
12. Sen, A. (2003) Bioreactor Protocols for the Long-Term Expansion of Mammalian Neural Stem Cells in Suspension Culture. *Ph.D. Thesis*. University of Calgary, Calgary, Alberta.

The invention claimed is:

1. A method for chemically detaching mammalian cells from a physical surface comprising the steps of:
    a) increasing the pH of the medium to a pH of about 9.0 to about 11.5 in the presence of an chelating agent;
    b) generating a single cell suspension; and
    c) decreasing the pH of the medium to a pH of less than 8.5.

2. The method of claim 1, wherein the chelating agent is EDTA.

3. The method of claim 1, wherein the cells are rocked in a culture vessel after the increase in pH.

4. The method of claim 1, wherein generating a single cell suspension comprises pipetting the medium over the physical surface.

5. The method of claim 4, wherein the pipetting is repeated 5 to 10 times.

6. The method of claim 1, further comprising (d) centrifuging the single cell suspension prior to decreasing the pH of the medium.

7. The method of claim 1, wherein the increase in pH is provided by alkaline medium.

8. The method of claim 7, wherein the alkaline medium comprises medium and a base.

9. The method of claim 8, wherein the base is selected from the group consisting of sodium hydroxide, potassium hydroxide, calcium hydroxide, ammonium hydroxide, zinc hydroxide, sodium phosphate tribasic dodecahydrate and sodium carbonate.

10. The method of claim 7, wherein the alkaline medium comprises phosphate buffered saline and a base.

11. The method of claim 10, wherein the base is sodium hydroxide.

12. The method of claim 1, wherein the pH is increased to about 10.

13. The method of claim 1, wherein the pH is decreased by placing the cells in fresh medium which is at neutral pH.

14. The method of claim 1, wherein the decrease in pH is provided by acidic medium.

15. The method of claim 14, wherein the acidic medium comprises medium and an acid.

16. The method of claim 15, wherein the acid is selected from the group consisting of hydrochloric acid, sulphuric acid, acetic acid, citric acid, phosphoric acid, and carbonic acid.

17. The method of claim 14, wherein the acidic medium comprises phosphate buffered saline and an acid.

18. The method of claim 17, wherein the acid is hydrochloric acid.

19. The method of claim 1 wherein the pH is decreased to a pH ranging from pH 7.0 to pH 8.5.

20. The method of claim 19, wherein the pH is decreased to about 8.1.

21. The method of claim 1, wherein the step of generating the single cell suspension is for a period of time of at least 7 minutes.

22. The method of claim 21, wherein the period of time is between 15 to 25 minutes.

23. The method of claim 21, further comprising rocking the cells gently for 2 to 5 minutes to detach the cells.

24. The method of claim 22, further comprising pipetting the cells after 15 to 25 minutes to dissociate cells into single cell suspension.

25. The method of claim 1, wherein the mammalian cells are selected from the group consisting of two cells, single cells, clusters of cells, monolayers and multiple layers.

26. The method of claim 1, wherein the mammalian cells are in in vitro cell culture.

27. The method of claim 1, wherein the mammalian cells are selected from the group consisting of Chinese Hamster Ovary cells, L-929 murine lung fibroblast cells, murine mammary epithelial cells MRC-5, He La, Vero, and MDCK.

28. The method of claim 1 wherein the mammalian cells are selected from the group consisting of stem cells, progenitor cells or mesenchymal cells.

29. The method of claim 28 wherein the stem cells are embryonic stem cells or pluripotent stem cells.

30. The method of claim 28 wherein the progenitor cells are endothelial progenitor cells.

* * * * *